United States Patent
Gunawan et al.

(10) Patent No.: US 10,788,494 B2
(45) Date of Patent: Sep. 29, 2020

(54) COMPOSITIONS AND METHODS FOR DETECTING AND QUANTIFYING HOST CELL PROTEIN IN CELL LINES AND RECOMBINANT POLYPEPTIDE PRODUCTS

(71) Applicant: Genentech, Inc., South San Francisco, CA (US)

(72) Inventors: Feny Gunawan, San Francisco, CA (US); Yi-Chun Hsiao, San Mateo, CA (US); Denise C. Krawitz, San Anselmo, CA (US); Margaret S. Lin, Danville, CA (US); Martin Vanderlaan, San Francisco, CA (US); Rajesh Vij, San Mateo, CA (US); Inn H. Yuk, Berkeley, CA (US); Judith Zhu-Shimoni, Kensington, CA (US)

(73) Assignee: Genentech, Inc., South San Francisco, CA (US)

(*) Notice: Subject to any disclaimer, the term of this patent is extended or adjusted under 35 U.S.C. 154(b) by 252 days.

(21) Appl. No.: 15/914,094

(22) Filed: Mar. 7, 2018

(65) Prior Publication Data
US 2018/0364235 A1  Dec. 20, 2018

Related U.S. Application Data

(60) Division of application No. 15/065,615, filed on Mar. 9, 2016, now Pat. No. 9,945,858, which is a continuation of application No. PCT/US2014/055382, filed on Sep. 12, 2014.

(60) Provisional application No. 61/991,228, filed on May 9, 2014, provisional application No. 61/877,503, filed on Sep. 13, 2013.

(51) Int. Cl.
*C07K 16/40* (2006.01)
*G01N 33/573* (2006.01)
*G01N 33/577* (2006.01)

(52) U.S. Cl.
CPC .......... *G01N 33/573* (2013.01); *C07K 16/40* (2013.01); *G01N 33/577* (2013.01); *C07K 2317/33* (2013.01); *C07K 2317/565* (2013.01); *G01N 2333/918* (2013.01); *G01N 2333/92* (2013.01); *G01N 2500/10* (2013.01)

(58) Field of Classification Search
CPC .............. G01N 33/573; G01N 33/577; G01N 2333/92; G01N 2333/918; G01N 2500/10; C07K 16/40; C07K 2317/565; C07K 2317/33
See application file for complete search history.

(56) References Cited

U.S. PATENT DOCUMENTS

| | | |
|---|---|---|
| 3,645,090 A | 2/1972 | Mochizuki et al. |
| 3,691,016 A | 9/1972 | Patel |
| 3,940,475 A | 2/1976 | Gross |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,376,110 A | 3/1983 | David et al. |
| 4,737,456 A | 4/1988 | Weng et al. |
| 4,816,567 A | 3/1989 | Cabilly et al. |
| 5,011,778 A | 4/1991 | Newman et al. |
| 5,229,275 A | 7/1993 | Goroff |
| 5,359,037 A | 10/1994 | Wallach et al. |
| 5,534,615 A | 7/1996 | Baker et al. |
| 5,545,807 A | 8/1996 | Surani et al. |
| 5,550,045 A | 8/1996 | Musters et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,596,072 A | 1/1997 | Culpepper et al. |
| 5,641,870 A | 6/1997 | Rinderknecht et al. |
| 5,652,123 A | 7/1997 | Caput et al. |
| 5,677,165 A | 10/1997 | De Boer et al. |
| 5,693,780 A | 12/1997 | Newman et al. |
| 5,705,154 A | 1/1998 | Dalie et al. |
| 5,710,023 A | 1/1998 | Collins et al. |
| 5,717,072 A | 2/1998 | Mosley et al. |

(Continued)

FOREIGN PATENT DOCUMENTS

| | | |
|---|---|---|
| CN | 101472947 | 7/2009 |
| CN | 101979404 A | 2/2011 |

(Continued)

OTHER PUBLICATIONS

Vanderlaan et al., "Experience with Host Cell Protein Impurities in Biopharmaceuticals" Biotechnol. Prog. 34(4):827-837 (2018).
Fischer et al., "Specific Immune Response to Phospholipase B-Like 2 Protein, a Host Cell Impurity in Lebrikizumab Clinical Material", The AAPS Journal, 19(1):254-263 (Jan. 2017).
"Monoclonal Anti-Human IL 13 Antibody," R&D Systems, Inc. Catalog [On-line], Oct. 2002 [retrieved on Oct. 14, 2002], Retrieved from the Internet: <URL: http://www.rndsystems.com/asp/c_search.asp?ucategory=3&factors=IL%2D13>.

(Continued)

*Primary Examiner* — Carmencita M Belei
(74) *Attorney, Agent, or Firm* — McNeill Baur PLLC

(57) ABSTRACT

Monoclonal and polyclonal antibodies that bind hamster phospholipase B-like 2 are provided. Also provided are methods for detecting and quantifying hamster phospholipase B-like 2, for example, in recombinant polypeptide preparations, as well as kits for carrying out such methods. Methods of screening or selecting host cell lines or recombinant polypeptide-expressing cell lines that express low levels of hamster phospholipase B-like 2 are also provided.

21 Claims, 13 Drawing Sheets

Specification includes a Sequence Listing.

(56) References Cited

U.S. PATENT DOCUMENTS

| | | |
|---|---|---|
| 5,747,037 A | 5/1998 | Noelle et al. |
| 5,783,181 A | 7/1998 | Browne et al. |
| 5,928,915 A | 7/1999 | Warner et al. |
| 5,965,709 A | 10/1999 | Presta et al. |
| 5,994,514 A | 11/1999 | Jardieu et al. |
| 6,037,453 A | 3/2000 | Jardieu et al. |
| 6,127,526 A | 10/2000 | Blank |
| 6,143,871 A | 11/2000 | Bonnefoy et al. |
| 6,156,321 A | 12/2000 | Thorpe et al. |
| 6,299,875 B1 | 10/2001 | Caplan et al. |
| 6,329,509 B1 | 12/2001 | Jardieu et al. |
| 6,333,398 B1 | 12/2001 | Blank |
| 6,468,528 B1 | 10/2002 | Mak et al. |
| 6,518,061 B1 | 2/2003 | Puri et al. |
| 6,576,232 B1 | 6/2003 | Debinski et al. |
| 6,664,227 B1 | 12/2003 | Wynn et al. |
| 6,743,604 B1 | 6/2004 | Bonnefoy et al. |
| 6,870,034 B2 | 3/2005 | Breece et al. |
| 6,911,530 B1 | 6/2005 | Willson et al. |
| 7,026,139 B2 | 4/2006 | Yang |
| 7,078,494 B1 | 7/2006 | Collins et al. |
| 7,078,496 B2 | 7/2006 | Roberts et al. |
| 7,157,276 B2 | 1/2007 | Pham |
| 7,312,024 B2 | 12/2007 | Mak et al. |
| 7,323,553 B2 | 1/2008 | Fahrner et al. |
| 7,501,121 B2 | 3/2009 | Tchistiakova et al. |
| 7,553,487 B2 | 6/2009 | Collins et al. |
| 7,615,213 B2 | 11/2009 | Kasaian et al. |
| 7,674,459 B2 | 3/2010 | Fung et al. |
| 7,759,117 B2 | 7/2010 | Pham |
| 7,863,426 B2 | 1/2011 | Wan et al. |
| 8,067,182 B2 | 11/2011 | Kelley et al. |
| 8,067,199 B2 | 11/2011 | Fung et al. |
| 8,088,618 B2 | 1/2012 | Fung et al. |
| 8,137,561 B2 | 3/2012 | Kozlov et al. |
| 8,318,160 B2 | 11/2012 | Fung et al. |
| 8,383,350 B1 | 2/2013 | Kolz et al. |
| 8,435,406 B2 | 5/2013 | Kozlov et al. |
| 8,449,885 B2 | 5/2013 | Meng et al. |
| 8,491,904 B2 | 7/2013 | Hickman |
| 8,715,669 B2 | 5/2014 | Masternak et al. |
| 9,605,065 B2 | 3/2017 | Fung et al. |
| 2003/0049257 A1 | 3/2003 | Mak et al. |
| 2003/0235555 A1 | 12/2003 | Shealey et al. |
| 2004/0242851 A1 | 12/2004 | Zhu |
| 2005/0032175 A1 | 2/2005 | Stahl et al. |
| 2005/0037333 A1 | 2/2005 | Pham |
| 2005/0226883 A1 | 10/2005 | Averback et al. |
| 2005/0277126 A1 | 12/2005 | Collins et al. |
| 2006/0073148 A1 | 4/2006 | Tchistiakova et al. |
| 2006/0194280 A1 | 8/2006 | Dillon et al. |
| 2006/0292643 A1 | 12/2006 | Goletz et al. |
| 2007/0037966 A1 | 2/2007 | Rasmussen et al. |
| 2007/0218516 A1 | 9/2007 | Palys et al. |
| 2007/0292442 A1 | 12/2007 | Wan et al. |
| 2008/0008648 A1 | 1/2008 | Fung et al. |
| 2008/0207497 A1 | 8/2008 | Ramakrishna et al. |
| 2008/0261249 A1 | 10/2008 | Wang et al. |
| 2009/0214523 A1 | 8/2009 | Fung et al. |
| 2009/0324604 A1 | 12/2009 | Liu et al. |
| 2010/0041039 A1 | 2/2010 | Harvey |
| 2010/0055103 A1 | 3/2010 | Chen et al. |
| 2010/0135987 A1 | 6/2010 | Hickman et al. |
| 2010/0150864 A1 | 6/2010 | Hickman et al. |
| 2010/0266494 A1 | 10/2010 | Fung et al. |
| 2011/0014199 A1 | 1/2011 | Fung et al. |
| 2011/0038877 A1 | 2/2011 | Way et al. |
| 2011/0093965 A1 | 4/2011 | O'Donoghue et al. |
| 2011/0123530 A1 | 5/2011 | Arron et al. |
| 2011/0256144 A1 | 10/2011 | Okano et al. |
| 2012/0027773 A1 | 2/2012 | Whalen et al. |
| 2012/0156194 A1 | 6/2012 | Arron et al. |
| 2012/0156203 A1 | 6/2012 | Fung et al. |
| 2012/0189639 A1 | 7/2012 | Schebye et al. |
| 2012/0210467 A1 | 8/2012 | Barton et al. |
| 2012/0214971 A1 | 8/2012 | Fung et al. |
| 2012/0294796 A1 | 11/2012 | Johnson et al. |
| 2012/0328624 A1 | 12/2012 | Yoshida et al. |
| 2013/0030159 A1 | 1/2013 | Han et al. |
| 2013/0089872 A1 | 4/2013 | Nakamura et al. |
| 2013/0142786 A1 | 6/2013 | Liu et al. |
| 2013/0224210 A1 | 8/2013 | Adamkewicz et al. |
| 2014/0105897 A1 | 4/2014 | Fung et al. |

FOREIGN PATENT DOCUMENTS

| | | |
|---|---|---|
| EP | 0 404 097 B1 | 6/1990 |
| EP | 0404097 * | 6/1990 |
| EP | 0 164 656 B1 | 9/1990 |
| EP | 1 270 595 B1 | 1/2003 |
| EP | 0 876 482 B1 | 3/2003 |
| EP | 1 327 681 A1 | 7/2003 |
| EP | 1 141 286 B1 | 10/2006 |
| JP | H0799971 | 4/1995 |
| WO | 89/04838 A1 | 6/1989 |
| WO | 91/09059 A1 | 6/1991 |
| WO | 93/11161 A1 | 6/1993 |
| WO | 93/15766 | 8/1993 |
| WO | 93/16185 A2 | 8/1993 |
| WO | 93/16185 A3 | 8/1993 |
| WO | 94/04680 A1 | 3/1994 |
| WO | 94/11026 A2 | 5/1994 |
| WO | 94/14975 A1 | 7/1994 |
| WO | 95/14780 A2 | 6/1995 |
| WO | 95/22389 | 8/1995 |
| WO | 97/15663 A1 | 5/1997 |
| WO | 97/20926 | 6/1997 |
| WO | 97/29131 | 8/1997 |
| WO | 97/31946 | 9/1997 |
| WO | 97/47742 | 12/1997 |
| WO | 98/10638 A1 | 3/1998 |
| WO | 98/30240 | 7/1998 |
| WO | 00/156663 | 3/2000 |
| WO | 00/23410 | 4/2000 |
| WO | 00/29004 A1 | 5/2000 |
| WO | 00/36103 | 6/2000 |
| WO | 0/44407 A2 | 8/2000 |
| WO | 01/34645 A2 | 5/2001 |
| WO | 01/92514 A1 | 6/2001 |
| WO | 2001/062801 | 8/2001 |
| WO | 02/051870 A2 | 7/2002 |
| WO | 02/051870 A3 | 7/2002 |
| WO | WO 02/055100 A2 | 7/2002 |
| WO | 03/035694 A2 | 5/2003 |
| WO | 03/035694 A3 | 5/2003 |
| WO | 03/035847 A2 | 5/2003 |
| WO | 03/040164 A2 | 5/2003 |
| WO | 03/018635 A1 | 6/2003 |
| WO | 03/086451 A1 | 10/2003 |
| WO | 2004/001655 A1 | 12/2003 |
| WO | 2004/019974 A2 | 3/2004 |
| WO | 2004/019975 A2 | 3/2004 |
| WO | 2004/019979 A2 | 3/2004 |
| WO | 2004/071408 | 8/2004 |
| WO | 2005/007699 A2 | 1/2005 |
| WO | 2005/007699 A3 | 1/2005 |
| WO | 2005/007699 A8 | 1/2005 |
| WO | 2005/035572 A2 | 4/2005 |
| WO | 2005/035572 A3 | 4/2005 |
| WO | 2005/062967 A2 | 7/2005 |
| WO | 2005/062967 A3 | 7/2005 |
| WO | 2005/062972 A2 | 7/2005 |
| WO | 2005/121177 A2 | 12/2005 |
| WO | 2005/123126 A2 | 12/2005 |
| WO | 2006/003407 A2 | 1/2006 |
| WO | 2006/085938 A2 | 7/2006 |
| WO | 2006/085938 A3 | 7/2006 |
| WO | WO 2006/099308 A2 | 9/2006 |
| WO | 2006/110277 | 10/2006 |
| WO | 2007/036745 A2 | 4/2007 |
| WO | 2007/036745 A3 | 4/2007 |
| WO | 2007/045477 A2 | 4/2007 |
| WO | 2007/045477 A3 | 4/2007 |
| WO | 2007/045477 A8 | 4/2007 |

(56) References Cited

FOREIGN PATENT DOCUMENTS

| WO | 2007/064972 | | 6/2007 |
|---|---|---|---|
| WO | 2007/068412 | | 6/2007 |
| WO | 2007/068429 | A1 | 6/2007 |
| WO | 2007/124143 | | 11/2007 |
| WO | 2008/011348 | A2 | 1/2008 |
| WO | 2008/011348 | A3 | 1/2008 |
| WO | 2008/060364 | | 5/2008 |
| WO | 2008/086395 | A2 | 7/2008 |
| WO | 2008/086395 | A3 | 7/2008 |
| WO | 2008-140455 | A1 | 11/2008 |
| WO | 2008/156621 | | 12/2008 |
| WO | 2008/156622 | | 12/2008 |
| WO | 2009/048537 | | 4/2009 |
| WO | 2009/048538 | | 4/2009 |
| WO | 2009/048539 | | 4/2009 |
| WO | 2009/124090 | A1 | 10/2009 |
| WO | 2009/131643 | A1 | 10/2009 |
| WO | 2009/136286 | | 11/2009 |
| WO | 2010/041037 | A2 | 4/2010 |
| WO | 2010/048190 | | 4/2010 |
| WO | 2010/048192 | | 4/2010 |
| WO | 2010/073119 | A1 | 7/2010 |
| WO | 2011/031397 | A1 | 3/2011 |
| WO | WO 2011/050071 | A2 | 4/2011 |
| WO | 2011109400 | | 9/2011 |
| WO | 2011/150110 | | 12/2011 |
| WO | 2012/016173 | | 2/2012 |
| WO | 2012/047732 | A2 | 4/2012 |
| WO | 2012/075037 | A1 | 6/2012 |
| WO | WO 2012/083132 | A2 | 6/2012 |
| WO | 2012/145493 | A1 | 10/2012 |
| WO | 2013/66707 | A1 | 5/2013 |
| WO | 2013/066866 | A1 | 5/2013 |
| WO | 2015/038884 | A2 | 3/2015 |

OTHER PUBLICATIONS

Abbas et al., Cell Molec Immunol (W.B. Saunders Co., Philadelphia, PA, p. 54), ( 1991).

Ahlers et al., "A push-pull approach to maximize vaccine efficacy: Abrogating suppression with an IL-13 inhibitor while augmenting help with granulocyte/macrophage colony-stimulating factor and CD40L" Proc Nat Acad Sci USA 99(20): 13020-13025 (Oct. 1, 2002).

Akbari et al., "Essential role of NKT cells producing IL-4 and IL-13 in the development of allergen-induced airway hyperreactivity" Nature Medicine 9(5):582-588 ( 2003).

Alberts et al. Molec Biol Cell "The Immune System" 3rd edition, New York & London:Garland Publishing, Inc.,( Suppl Ch 23):1208-1209 ( 1994).

Amrad Corporation, Ltd, , "Project: IL-13 receptor antibody" Aug. 17, 2005.

Andrews et al., "Kinetic analysis of the interleukin-13 receptor complex" J Biol Chem 277(48):46073-46078 (Nov. 29, 2002).

Anicetti et al., "Immunoassay for the detection of E. coli proteins in recombinant DNA derived human growth hormone" J Immunol Methods 91(2):213-224 ( 1986).

Arima et al., "Characterization of the interaction between interleukin-13 and interleukin-13 receptors" J Biol Chem 280(26):24915-24922 (Jul. 1, 2005).

Arima et al., "Upregulation of IL-13 concentration in vivo by the IL13 valiant associated with bronchial asthma" J Allergy Clin Immunol 109(6):980-987 (2002).

Asthma and Allergy Foundation of America and The national Pharmaceutical Council, "A closer look at asthma" pp. 1-6.

Becker et al., "Unraveling the chinese hamster ovary cell line transcriptome by next-generation sequencing" J Biotechnol 156:227-235 (2011).

Bellanti, JA, "Cytokines and allergic diseases: clinical aspects" Allergy Asthma Proc ((Abstract only)), 19(6):337-341 ( 1998).

Blanchard et al., "Inhibition of human interleukin-13-induced respiratory and oesophageal inflammation by anti-human-interleukin-13 antibody (CAT-354)" Clin Exp Allergy 35:1096-1103 ( 2005).

Blattner et al., "The complete genome sequence of Escherichia coli K-12." Science 277:1453-1462 (Sep. 1997).

Blease et al., "Therapeutic effect of IL-13 immunoneutralization during chronic experimental fungal asthma" J Immuinol 165:5219-5224 ( 2001).

Bomans et al., "Identification and monitoring of host cell proteins by mass spectrometry combined with high performance immunochemistry testing" PLoS ONE 8(11):e81639 ( 2013).

Bosmann et al., "Detection of serum free light chains: the problem with antigen excess" Clin Chem Lab Med 48(10):1419-1422 ( 2010).

Bost et al., "In vivo treatment with anti-interleukin-13 antibodies significantly reduces the humoral immune response against an oral immunogen in mice" Immunology 87(4):633-641 ( 1996).

Bree et al., "IL-13 blockade reduces lung inflammation after Ascaris suum challenge in cynomolgus monkeys" J Allergy Clin Immunol 119:1251-1257 ( 2007).

Brennan et al., "Preparation of bispecific antibodies by chemical recombination of monoclonal immunoglobulin $G_1$ fragments" Science 229(4708):81-83 (Jul 5, 1985).

Brewer et al., "Inhibition of key cytokines by tetrathiomolybdate in the bleomycin model of pulmonary fibrosis" J Inorg Biochem 98:2160-2167 ( 2004).

Brinkmann et al., "TCR-stimulated naive human $CD4^{+}$ $45RO^{-}$ T cells develop into effector cells that secrete IL-13, IL-5, and IFN-y, but no IL-4, and help efficient IgR production by B cells" J Immunol 154(7):3078-3087 ( 1995).

Brinks et al., "Immunogenicity of therapeutic proteins: the use of animal models" Pharm Res 28:2379-2385 ( 2011).

Brodeur et al., "Mouse-human myeloma partners for the production of heterohybridomas" Monoclonal Antibody Production Techniques and Applications, (New York: Marcel Dekker, Inc.),:51-63 ( 1987).

Brodsky et al., "Caprylic acid precipitation method for impurity reduction: An alternative to conventional chromatography for monoclonal antibody purification" Biotechnol Bioeng 109(10):2589-2598 (Oct. 2012).

Brown et al., "A family of small inducible proteins secreted by leukocytes are members of a new superfamily that includes leukocyte and fibroblast-derived inflammatory agents, growth factors, and indicators of various activation processes" J Immunol 142(2):679-687 (Jan. 15, 1989).

Bruggermann et al., "Designer mice: The production of human antibody repertoires in transgenic animals" Year Immun 7:33-40 ( 1993).

Caldas et al., "Humanization of the anti-CD18 antibody 6.7 : an unexpected effect of a framework residue in binding to antigen" Mol Immunol 39:941-952 ( 2003).

Campbell et al., "Allergic humans are hyporesponsive to a CXCR3 ligand-mediated Th1 immunity-promoting loop" FASEB J 18(2):329-331 ( 2003).

Caput et al., "Clining and characterization of a specific interleukin (IL)-13 binding protein structurally related to the IL-5 receptor $\alpha$ chain" J Biol Chem 271(28):16921-16926 (Jul. 12, 1996).

Carbadillo et al., "IL-4 induces human B cell maturation and IgE synthesis in SCID-hu mice" J Immunol 155(9):4162-4170 ( 1995).

Carrington, "BIAcore analysis of hIL-13Ra2 binding/blocking to hIL-13 pre-bound to antibody JES10-5A2 or antibody 213" UCB Celltech:1-3 (Jun. 7, 2007).

Carter et al., "High level Escherichia coli expression and production of a bivalent humanized antibody fragment" Bio/Technol 10:163-167 (Feb. 1992).

Carter et al., "Humanization of an anti-p185 $HER2$ antibody for human cancer therapy" P Natl Acad Sci USA 89:4285-4289 (May 1992).

Casolaro et al., "Biology and genetics of atopic disease" Curr Opin Immunol 8:796-803 ( 1996).

Casset et al., "A peptide mimetic of an anti-CD4 monoclonal antibody by rational design" Biochem Bioph Res Co 307(1):198-205 (Jul. 18, 2003).

(56) References Cited

OTHER PUBLICATIONS

Champion et al., "The challenges of monitoring host cell protein impurities", CMC Strategy Forum, Jul. 19-20, 2004.

Champion at al., "Defining your product profile and maintaining control over it, Part 2, Challenges of monitoring host cell protein impurities" Bioproc Int:52-57 (Sep. 2005).

Champion at al., "Similarity of the *Escherichia coli* proteome upon completion of different biopharmaceutical fermentation processes" Proteomics 1:1133-1148 ( 2001).

Chen et al., "Quantitation of *E. coli* protein impurities in recombinant human interferon-y" Applied Biochem Biotechnol 36:137-152 ( 1992).

Chen, A., "Development and validation of immunoassays for host cell proteins in recombinant DNA-derived protein pharmaceuticals" J Biotechnology Healthcare 3(1):70-80 ( 1996).

Chien et al., "Significant structural and functional change of an antigen-binding site by a distant amino acid substitution: Proposal of a structural mechanism" P Natl Acad Sci USA 86:5532-5536 (Jul. 1989).

Chothia et al., "Canonical structures for the hypervariable regions of immunoglobulins" J Mol Biol 196:901-917 ( 1987).

Clackson et al., "Making antibody fragments using phage display libraries" Nature 352(6336):624-628 (Aug. 15, 1991).

Cohn et al. et al., "Induction of Airway Mucus Production by T Helper 2 (Th2) Cells: A Critical Role for Interleukin 4 in Cell Recruitment but not Mucus Production" J Exp Med 186(10):1737-1747 (Nov. 17, 1997).

Cohn et al., "Cutting Edge: IL-4-independent induction of airway hyperresponsiveness by Th2, but not Th1, cells" J Immunol 161:3813-3816 ( 1998).

Corren et al., "Lebrikizumab treatment in adults with asthma" N Engl J Med 365(12):1088-1098 (Sep. 22, 2011).

Coutinho et al., "Mannose-6-phosphate pathway: a review on its role in lysosomal function and dysfunction" Molec Genetics Metabolism 105:542-550 (2012).

Cunningham and Wells, "High-resolution epitope mapping of hGH-receptor interactions by alanine-scanning mutagenesis" Science 24:1081-1085 (Jun. 2, 1989).

Daniels et al., "Imatinib mesylate inhibits the profibrogenic activity of TGF-β and prevents bleomycin-mediated lung fibrosis" J Clin Invest 114(9):1308-1316 ( 2004).

Daval et al., "Risk of antigen excess in serum free light chain measurements" Clin Chem 53:1985-1986 ( 2007).

David and Reisfeld, "Protein Iodination with Solid State Lactoperoxidase" Biochemistry—US 13(5):1014-1021 (Feb. 26, 1974).

Davies and Riechmann, "'Camelising' human antibody fragments: NMR studies on VH domains" FEBS Lett 339:285-290 ( 1994).

De Pascalis et al., "Grafting of 'abbreviated' complementarity-determining regions containing specificity-determining residues essential for ligand contact to engineer a less immunogenic humanized monoclonal antibody" J Immunol 169:3076-3084 (2002).

de Swart et al., "Immunization of Macaques with formalin-inactivated respiratory syncytial virus (RSV) induces interleukin-13-associated hypersensitivity to subsequent RSV infection" J Virol 76(22): 11561-11569 ( 2002).

de Vries et al., "Modulation of the human IgE response" Eur Respir J (Suppl. 9( Suppl 22):58s-62s ( 2002).

de Vries, J. E., "Novel fundamental approaches to intervening in IgE-mediated allergic diseases" J Invest Dermatol 102:141-144 ( 1994).

Debinski et al., "A novel chimeric protein composed of interleukin 13 and pseudomonas exotoxin is highly cytotoxic to human carcinoma cells expressing receptors for interleukin 13 and interleukin 4" J Biol Chem 270(28): 16775-16780 ( 1995).

Debinski et al., "Human glioma cells overexpress receptors for interleukin 13 and are extremely sensitive to a novel chimeric protein composed of interleukin 13 and pseudomonas exotoxin" Clin Cancer Res 1:1253-1258 ( 1995).

Deuschl et al., "Molecular characterization of the hypothetical 66.3-kDa protein in mouse: lysosomal targeting, glycosylation, processing and tissue distribution" FEBS Lett 580:5747-5752 ( 2006).

Donaldson et al., "The murine IL-13 receptor α2: Molecular cloning, characterization, and comparison with murine IL-13 receptor α1" J Immunol 161:2317-2324 ( 1998).

Doneaunu et al., "Analysis of host-cell proteins in biotherapeutic proteins by comprehensive online two-dimensional liquid chromatography/mass spectrometry" mAbs (10.4161/mabs.4.1.18748), 4:1, 24-44 (2012).

Dooley and Flajnik, "Antibody repertoire development in cartilaginous fish" Developmental and Comparative Immunol 30:43-56 ( 2006).

Dorland's Illustrated Medical Dictionary 28th edition, Philadelphia:W. B. Saundres,:151 ( 1994).

Doucet et al., "Interleukin (IL)4 and IL-13 act on human lung fibroblasts, Implication in Asthma" J Clin Invest 101:2129-2139 ( 1998).

Eaton, L., "Host cell contaminant protein assay development for recombinant biopharmaceuticals" J Chromatogr A 705(1):105-114 (Jun. 23, 1995).

Economides et al., "Designer cytokines: Targeting actions to cells of choice" Science 270:1351-1353 ( 1995).

Encyclopedia Britannica's Guide to the Nobel Prizes, "Immune system disorders" [on-line], Jun. 27, 2007 [retrieved on Jun. 27, 2007], pp. 1-4, Retrieved from the Internet:<URL: http://www.britannica.com/nobelprize/article-215507>.

Enomoto et al., "High-throughput miniaturized immunoassay for human interleukin-13 secreted from NK3.3 cells using homogenous time-resolved fluorescence" J Pharm Biomed Analysis 28:73-79 (2002).

European Supplemental Search Report EP 14 84 4121, dated Feb. 20, 2017, 5 pages.

Fauci et al. Harrison's Principles of Internal Medicine "Asthma" 14th edition, McGraW-Hill,:1419-1420, 1760-1761 ( 1998).

Fichtner-Feigl et al., "IL-13 signaling through the IL-12α\\\subscript:2\\\ receptor is involved in induction of TGF-B\\\subscript:1\\\ production and fibrosis" Nat Med 12(1):99-106 (Jan. 2006).

Flatman et al., "Process analytics for purification of monoclonal antibodies" J Chromatography 848:79-7 ( 2007).

Gabrielsson et al., "Increased frequencies of allergen-induced interleukin-13-producing cells in atopic individuals during the pollen season" Scand J Immunol 48:429-435 ( 1998).

Gagnon, "Monoclonal antibody purification with hydroxyapatite" New Biotechnol (XP002610667), 25(5):287-293 (Jun. 2009).

Gao et al., "Fragmentation of a highly purified monoclonal antibody attributed to residual CHO cell protease activity" Biotechnol Bioeng 108(4):977-982 (Apr. 2011).

Gauvreau et al., "Effects of interleukin-13 blockade on allergen-induced airway responses in mild atopic asthma" Am J Respir Crit Care Med 83:1007-1014 ( 2011).

GE Healthcare Life Sciences, Data file 11-0011-65 AC, "MabSelect SuRe".

Genebank Accession No. NP_002179 (Apr. 7, 2003) Interleukin 13 Precursor (*Homo sapiens*) http://www.ncbi.nlm.nih.gov/protein/26787978?sat=24&satkey=4532247.

George et al., "Differential effects of anti-β\\\subscript:2\\\-glycoprotein I antibodies on endothelial cells and on the manifestations of experimental antiphospholipid syndrome" Circulation 97:900-906 ( 1998).

Ghaderi et al., "Implications of the presence of N-glycolylneuraminic acid in recombinant therapeutic glycoproteins" Nature Biotechnol 28(8):863-869 (Aug. 2010).

Ghaffar et al., "IL-13 mRNA and Immunoreactivity in Allergen-induced rhinitis: Comparison with IL-4 expression and modulation by topical glucocorticoid therapy" Am J Respir Cell Mol Biol 17:17-324 ( 1997).

Ghamdi et al., "IL-4 and IL-13 expression in chronic sinusitis: relationship with cellular infiltrate and effect of topical corticosteroid treatment" J Otolaryngology 26(3):160-166 ( 1997).

(56) References Cited

OTHER PUBLICATIONS

Ghose et al., "Purification of monoclonal antibodies by hydrophobic interaction chromatography under no-salt conditions" mAbs 5(5):795-800 (Sep. 2013).
Giusti et al., "Somatic Diversification of S107 from an Antiphosphocholine to an anti-DNA Autoantibody is Due to a Single Base Change in its Heavy Chain Variable Region" P Natl Acad Sci USA 84:2926-2930 (May 1987).
Goding, Monoclonal Antibodies: Principles and Practice "Production and Application of Monoclonal Antibodies in Cell Biology, Biochemistry and Immunology"Academic Press,:56-103 ( 1986).
Grampp et al., "Managing unexpected events in the manufacturing of biologic medicines," Biodrugs DOI 10.1007/s40259-013-0018-5 Published online on Mar. 26, 2013.
Griffiths et al., "Human anti-self antibodies with high specificity from phage display libraries" Embo J 12(2):725-734 ( 1993).
Grunig et al., "Requirement of IL-13 independently of IL-4 in experimental asthma" Science 282:2261-2263 (Dec. 18, 1998).
Gussow et al., "Humanization of Monoclonal Antibodies" Meth Enzymol 203:99-121 ( 1991).
Hamid et al., "In Vivo expression of IL-12 and IL-13 in atopic dermatitis" J Allergy Clin Immunol 98:225-231 ( 1996).
Hamster putative phospholipase B-like 2 (PLBDZ) ELISA kit, Cusabio, Catalog No. CSB-EL018125HA (For the quantitative determination of hamster putative phospholipase B-like 2 (PLBS2) concentrations in serum, plasma, tissue homogenates and cell lysates).
Hanania et al., "Lebrikizumab in moderate-to-severe asthma: pooled data from two randomised placebo-controlled studies" Thorax 70:748-756 (2015).
Hasegawa et al., "Serum levels of tumor necrosis factor and interleukin-13 are elevated in patients with localized scleroderma" Dermatology 207:141-147 ( 2003).
Helen G. Haggerty, PhD, "Hamster MCP-1: Potential Culprit of Clinical Adverse Events" Slides CRL Biotechnology Symposium, pp. 26 ( Sep. 8-10, 2014).
Heller et al., "Interleukin-13 is the key effector Th2 cytokine in ulcerative colitis that affects epithelial tight junctions, apoptosis, and cell restitution" Gastroenterology 129:550-564 ( 2005).
Heller et al., "Oxazolone colitis, a Th2 colitis model resembling ulcerative colitis, is mediated by IL-13-producing NK-T cells" Immunity 17:629-638 ( 2002).
Hershey et al., "IL-13 receptors and signaling pathways: an evolving web" J Allergy Clin Immunol 111(4):677-690 (Apr. 2003).
Hoffman, "Strategies for Host Cell Protein Analysis" Biopharm 13:38-45 ( 2000).
Hogwood et al., "Host cell protein dynamics in recombinant CHO cells" Bioengineered 4(5):288-291 (2013).
Hollinger et al., "Diabodies: Small Bivalent and Bispecific Antibody Fragments" P Natl Acad Sci USA 90:6444-6448 (Jul. 1993).
Holm et al., "Functional mapping and single chain construction of the anti-cytokeratin 8 monoclonal antibody TS1" Mol Immunol 44:1075-1084 ( 2007).
Holt et al., "Domain antibodies: proteins for therapy" Trends Biotechnol 21(11):484-490 (Nov. 2003).
http://www.cusabio.com/ELISA-kit/Hamster-Putative-phospholipase-B-like-2PLBD2-ELISA-kit-118621.html.
Huang et al., "IL-13 expression at the sites of allergen challenge in patients with asthma" J Immunol 155:2688-2694 ( 1995).
Humbert et al., "Elevated expression of messenger ribonucleic acid encoding IL-13 in the bronchial mucosa of atopic and nonatopic subjects with asthma" J Allergy Clin Immunol 99:657-665 ( 1997).
Hunter et al., "Preparation of Iodine-131 Labelled Human Growth Hormone of High Specific Activity" Nature 194(4827):495-496 (May 5, 1962).
Iba et al., "Changes in the specificity of antibodies against steroid antigens by introduction of mutatations into complementarity-determining regions of the VH domain" Protein Eng (Abstract only), 11(5):361-370 ( 1998).

Ingram et al., "IL-13 in asthma and allergic disease: Asthma phenotypes and targeted therapies" J Allergy Clin Immunol 130:829-842 ( 2012).
Inspiration Biopharmaceuticals announces clinical hold of clinical trials evaluating IB1001 for the treatment and prevention of bleeding in hemophilia B, Cambridge, MA (2012).
International Search Report on patentability for International Patent Application No. PCT/US2014/055387.
International Search Report on Patentability for International Patent Application No. PCT/US14/55382.
Ipsen and Inspiration Biopharmaceuticals announce closing of the IB1001 sale to Cangene Corporation Paris, France (2013).
Jakobovits et al., "Analysis of homozygous mutant chimeric mice: Deletion of the immunoglobulin heavy-chain joining region blocks B-cell development and antibody production" P Natl Acad Sci USA 90:2551-2555 (Mar. 1993).
Jakobovits et al., "Germ-line transmission and expression of a human-delived yeast artificial chromosome" Nature 362:255-258 (Mar. 18, 1993).
Jakubzick et al., "Therapeutic attenuation of pulmonary fibrosis via targeting of IL-4- and IL-13-responsive cells" J Immunol 171:2684-2693 (2003).
Janeway and Travers Immunobiology: The Immune System in Health and Disease "Allergy and Hypersensitivity" 3rd edition, New York and London:Garland Publishing Inc.,:11:1-11.25.
Janeway and Travers Immunobiology: The Immune System in Health and Disease "Adaptive immunity to infection" 3rd edition, New York and London:Garland Publishing Inc.,:9:31-9:33.
Jawa et al., "Evaluating Immunogencity Risk Due to Host Cell Protein Impurities in Antibody-Based Biotherapeautics" The AAPS Journal 18(6):14 (Nov. 2016).
Jenner et al., "Serum free light chain immunoassays: a guide to antigen excess detection" Clin Chim Acta 413:949 ( 2012).
Jensen et al., "Biochemical characterization and lysosomal localization of the mannose-6-phosphate protein p76 (hypothetical protein LOC196463)" Biochem J 402:449-463 ( 2007).
Jiang et al., "A novel peptide isolated from a phage display peptide library with trastuzumab can mimic antigen epitope of HER-2*" J Biol Chem 280(6):4656-4662 ( 2005).
Johnson et al., "Human Antibody Engineering" Curr Opin Struc Biol 3:564-571 (1993).
Jones et al., "Replacing the complementarity-determining regions in a human antibody with those from a mouse" Nature 321:522-525 (May 29, 1986).
Jones The Impact of Chemistry on Biotechnology "Sensitive detection and quantitation of protein contaminants in rDNA products" Phillips M.,American chemical Society,: 193-201 ( 1988).
Judy Shimoni, "Host Cell Protein ELISAs and the Use of Orthogonal Methods" Slides Washington, DC, pp. 25 (Jan. 30, 2013).
Kabat et al. Sequences of Proteins of Immunological Interest 5th edition,NIH,:2 pages ( 1991).
Kapp et al., "Interleukin 13 is secreted by and stimulates the growth of Hodgkin and Reed-Sternberg cells" J Exp Med 189(12):1939-1945 (Jun. 21, 1999).
Kasaian et al., "Efficacy of IL-13 neutralization in a sheep model of experimental asthma" Am J Respir Cell Mol Biol 36:368-376 ( 2007).
Kawakami et al., "Interleukin-13 receptor-targeted cancer therapy in an immunodeficient animal model of human head and neck cancer" Cancer Res 61:6194-6200 ( 2001).
Kawakami et al., "Intratumor administration of interleukin 13 receptor-targeted cytotoxin induces apoptotic cell death in human malignant glioma tumor xeno grafts" Mol Cancer Ther 1:999-1007 (Oct. 2002).
Keane et al., "IFN-γ-inducible protein-10 attenuates bleomycin-induced pulmonary fibrosis via inhibition of angiogenesis" J Immunol 163:5686-5692 ( 1999).
Keane et al., "Neutralization of the CXC chemokine, macrophage inflammatory protein-2, attenuates bleomycin-induced pulmonary fibrosis" J Immunol 162:5511-5518 ( 1999).
Kettleborough et al. et al., "Humanization of a Mouse Monoclonal Antibody by CDR-grafting: the Importance of Framework Residues on Loop Conformation" Protein Eng 4(7):773-783 ( 1991).

(56) References Cited

OTHER PUBLICATIONS

Kim et al., "IL-13-induced Clara cell secretory protein expression in airway epithelium: role of EGFR signaling pathway" Am J Physiol Lung Cell Mol Physiol 283:L67-L75 ( 2002).

Kimata et al., "Involvement of interleukin (IL)-13, but not IL-4, in spontaneous IgE and IgG4 production in nephrotic syndrome" Eur J Immunol (Abstract only), 25(6):1497-1501 ( 1995).

Kindt et al. Kuby Immunology "Antigens and Antibodies Chapter 4" 6th ed edition, N.Y.:W.H. Freeman and Co,:p. 91 ( 2007).

Kita et al., "Biochemical properties and and pathophysiological roles of cytosolic phospholipase A $_2$S" Biochim Biophys Acta 1761:1317-1322 ( 2006).

Kohler and Milstein, "Continuous cultures of fused cells secreting antibody of predefined specificity" Nature 256:495-497 (Aug. 7, 1975).

Kotsimbos et al., "Interleukin-13 and interleukin-4 are coexpressed in atopic asthma" Proc Assoc Am Physicians 108(5):368-373 ( 1996).

Kozbor et al., "A Human Hybrid Myeloma for Production of Human Monoclonal Antibodies" J Immunol 133(6):3001-3005 (Dec. 1, 1984).

Krawitz et al., "Proteomic studies support the use of multi-product immunoassays to monitor host cell protein impurities" Proteomics 6:94-100 (2006).

Kroegel et al., "Endobronchial secretion of interleukin-13 following local allergen challenge in atopic asthma: relationship to interleukin-4 and eosinophil counts" Eur Respir J 9:899-904 ( 1996).

Kuperman et al., "Direct effects of interleukin-13 on epithelial cells cause airway hyperreactivity and mucus overproduction in asthma" Nat Med 8(8):885-889 (2002).

Lakomek et al., "Initial insight into the function of the lysosomal 66.3 kDa protein from mouse by means of X-ray crystallography" BMC Structural Biol 9:56 ( 2009).

Laporte et al., "Molecular and structural basis of cytokine receptor pleiotropy in the interleukin-4/13 system" Cell 132(2):259-272 ( 2008).

Lee et al., "Interleukin-13 induces tissue fibrosis by selectively stimulating nad activating transforming growth factor B\\\subscript:1\\\" J Exp Med 194(4):809-821 (Sep. 17, 2001).

Lee et al., "Serum levels of interleukins (IL)-4, IL-5, IL-13, and interferon-γ in acute asthma" J Asthma 38(8):665-671 ( 2001).

Leister, "Identification and control of process impurities and product related variants in the development and manufacture of a glycoprotein" IBC Life Sciences Product and Process Variants and Impurities Conference, Washington, D.C. ( 2013).

Levy et al., "Role of IL-13 in CD4 T cell-dependent IgE production in atopy" Int Arch Allergy Immunol 112:49-58 ( 1997).

Lewis et al., "Genomic landscapes of Chinese hamster ovary cell lines as revealed by the Cricetulus griseus draft genome" Nat Biotechnol 31(8):759-765 (Aug. 2013).

Liu et al., "Recovery and purification process development for monoclonal antibody production" mAbs 2(5):480-499 (Sep. 2010).

Liu et al., "Regulation of found in inflammatory zone 1 expression in bleomycin-induced lung fibrosis: Role of IL-4/IL-13 and mediation via STAT-6" J Immunol 173:3425-3431 (2004).

Lucas et al., "Enzyme-linked immunosorbent assays (ELISAs) for the determination of contaminants resulting from the immunoaffinity purification of recombinant proteins" J Immunol Meth 113:113-122 (1988).

Luhrs et al., "Evicting hitchhiker antigens from purified antibodies" J Chromatograph B:1543-1552 ( 2009).

Lukacs et al., "Respiratory syncytial virus predisposes mice to augmented allergic airway responses via IL-13-mediated mechanisms" J Immunol 167:1060-1065 ( 2001).

MacCallum et al., "Antibody-antigen interactions: contact analysis and binding site topography" J Mol Biol 262(5):732-745 (Oct. 11, 1996).

Madhankumar et al., "Alanine-scanning mutagenesis of α-helix D segment of interleukin-13 reveals new functionally important residues of the cytokine" J Biol Chem 277(45):43194-43205 (Nov. 8, 2002).

Maini et al., "Interleukin-13 receptors on human prostate carcinoma cell lines represent a novel target for a chimeric protein composed of IL-13 and a mutated form of pseudomonas exotoxin" J Urology 158:945-953 ( 1997).

Mariuzza et al., "The Structure Basis of Antigen-Antibody Recognition" Ann Rev Biophys Biophys Chem 16:139-159 ( 1987).

Marks et al., "By-passing immunization, human antibodies from V-gene libraries displayed on phage" J Mol Biol 222:581-597 ( 1991).

Marks et al., "By-passing immunization: building high affinity human antibodies by chain shuffling" Bio/Technology 10:779-783 (Jul. 1992).

Marsh et al., "Linkage analysis of IL4 and other chromosome 5q31.1 markers and total serum immunoglobulin E concentrations" Science 264:1152-1156 (May 20, 1994).

Mashushita et al., "Upregulation of interleukin-13 and its receptor in a murine model of bleomycin-induced scleroderma" Int Arch Allergy Immunol 135:348-356 ( 2004).

McCafferty et al., "Phage Antibodies: Filamentous Phage Displaying Antibody Variable Domains" Nature 348:552-554 (Dec. 1990).

McKenzie et al., "Impaired development of Th2 cells in Il-13-deficient mice" Immunity 9:423-432 (Sep. 1998).

McKenzie et al., "Interleukin 13, a T-cell-derived cytokine that regulates human monocyte and B-cell function" Proc Natl Acad Sci USA 90:3735-3739 (Apr. 1993).

McKenzie et al., "Measurement of interleukin-13" Curr Protocols Immunol (Unit 6.18, Suppl. 10:6.18.1-6.18.5, Coligan et al., eds., John Wiley & Sons, New York).

Mechetner et al., "The effects of hitchhiker antigens co-eluting with affinity-purified research antibodies" J Chromatograph B 879:2583-2594 ( 2011).

Mehta et al., "Purifying therapeutic monoclonal antibodies" SBE Special Section/Bioprocessing:S14-S20.

Mentink-Kane et al., "Opposing roles for IL-13 and IL-13 receptor α2 in health and disease" Immunological Rev 202:191-202 ( 2004).

Merck Manual—Online Medical Dictionary, "Hyperimmunoglobulinemia E Syndrome," [on-line], Jul. 7, 2007 [Retrieved on Jul. 7, 2007], Retried from the Internet: <URl: http://www.merck.com/mmhe/sec16/ch184k.html>, pp. 1-2., pp. 1-2 (Jul. 7, 2007).

Merrifield, "Solid phase peptide synthesis: The synthesis of a tetrapeptide" J Am Chem Soc 85:2149-2154 ( 1963).

Mihara et al., "Host Cell Proteins: The Hidden Side of Biosimilarity Assessment" Journal of Pharmaceutical Sciences 104:3991-3996 (2015).

Millipore Technical Bulletin, Lit. No. 1026EN00, Jul. 2006 (available at www.Millipore.com).

Miloux et al., "Cloning of the human IL-13Rα1 chain and reconstitution with the IL-4Rα of a functional IL-4/IL-13 receptor complex" FEBS Lett 401:163-166 ( 1997).

Morimoto and Inouye, "Single-step purification of F(ab') 2 fragments of mouse monoclonal antibodies (immunoglobulins G1) by hydrophobic interaction high performance liquid chromatography using TSKgel phenyl-5PW" J Biochem Biophys Meth 24:107-117 ( 1992).

Morrison et al., "Chimeric human antibody molecules: Mouse antigen-binding domains with human constant region domains" P Natl Acad Sci USA 81:6851-6855 (Nov. 1984).

Mueller et al., "Structure, binding, and antagonists in the IL-4/IL-13 receptor system" Biochim Biophys Acta 1592:237-250 ( 2002).

Munson and Rodbard, "LIGAND: A Versatile Computerized Approach for Characterization of Ligand-Binding Systems" Anal Biochem 107(1):220-239 (Sep. 1, 1980).

Muyldermans et al., "Recognition of antigens by single-domain antibody fragments: the superfluous luxury of paired domains" Trends Biochem Sci 26(4):230-235 (Apr. 2001).

Naseer et al., "Expression of IL-12 and IL-13 mRNA in asthma and their modulation in response to steroid therapy" Am Respir Crit Care Med 155:845-857 ( 1997).

(56) References Cited

OTHER PUBLICATIONS

Noonan et al., "Dose-ranging study of lebrikizumab in asthmatic patients not receiving inhaled steroids" J Allergy Clin Immunol 132:567-574 ( 2013).
Noverr et al., "Production of eicosanoids and other oxylipins by pathogenic eukaryotic microbes" Clin Microbiol Rev 16(3):517-533 (Jul. 2003).
Noverr et al., "Role of PLB1 in pulmonary inflammation and cryptococcal eicosanoid production" Infect Immun 71(3):1538-1547 (Mar. 2003).
Nygren, H., "Conjugation of Horseradish Peroxidase to Fab Fragments with Different Homobifunctional and Heterobifunctional Cross-Linking Reagents" J Histochem Cytochem 30(5):407-412 (May 1982).
Ohno et al., "Antigen binding specificities of antibodies are primarily determined by seven residues of VH" Proc. Natl. Acad Sci. USA 82(9):2945-2949 ( 1985).
Okuma et al., "C-C chemokine receptor 2 (CCR2) deficiency improves bleomycin-induced pulmonary fibrosis by attenuation of both macrophage infiltration and production of macrophage-derived matrix metalloproteinases" J Pathol 204:594-604 ( 2004).
Omnitrope: EPAR-Scientific Discussion, European Medicines Agency, 2006.
Oshima et al., "Characterization of a powerful high affinity antagonist that inhibits biological activities of human interleukin-13" J Biol Chem 276(18): 15185-15191 (May 4, 2001).
Oxford Concise Medical Dictionary "Atopy" 4th edition, Great Britian:Oxford University Press,:54-55 ( 1994).
Pahl, et al., "Regulation of IL-13 synthesis in human lymphocytes: implications for asthma therapy," British Journal of Pharmacology (2002) 135, 1915-1926.
Pain and Surolia, "Preparation of Protein A—Peroxidase Monoconjugate Using a Heterobifunctional Reagent, and its Use in Enzyme Immunoassays" J Immunol Methods 40(2):219-230 ( 1981).
Pawankar et al., "Nasal mast cells in perennial allergic rhinitics exhibit increased expression of the FcεRI, CD40L, IL-4, and IL-l3, and can induce IgE synthesis in B cells" J Clin Invest 99(7):1492-1499 (Apr. 1997).
Peebles et al., "Immune interaction between respiratory syncytial virus infection and allergen sensitization critically depends on timing of challenges" J Infect Dis 184:1374-1379 ( 2001).
Pluckthun, A. The Pharmacology of Monoclonal Antibodies: Handbook of Pharmacology "Antibodies from *Escherichia coli*" (Chapter 11), Rosenberg and Moore, eds., Berlin:Springer-Verlag, vol. 113:269-315 ( 1994).
Pluckthun, A., "Mono- and bivalent antibody fragments produced in *Escherichia coli:* engineering, folding and antigen binding" Immunol Reviews(130):151-188 ( 1992).
Portolano et al., "Lack of promiscuity in autoantigen-specific H and L chain combinations as revealed by human H and L chain 'roulette'" J Immunol 150(3):880-7 (Feb. 1, 1993).
Postma et al., "Genetic susceptibility to asthma—bronchial hyperresponsiveness coinherited with a major gene for atopy" N Engl J Med 333(14):894-900 ( 1995).
Presta et al., "Humanization of an antibody directed against IgE" J Immunol 151(5):2623-2632 (Sep. 1993).
Presta, "Antibody engineering" Curr Opin Struct Biol 2:593-596 ( 1992).
Punnonen et al. Allergy and Allergic Diseases: The New Mechanisms and Therpeutics "Cytokines and IgE regulation" J.A. Denburg, Totowa, NJ:Humana Press Inc.,:13-40 ( 1998).
Quarmby et al., "Immunogenicity: A critical issue in biotherapeutic development" AAPS Newsmagazine, May 12.
Rader et al., "A Phage Display Approach for Rapid Antibody Humanization: Designed Combinatorial V Gene Libraries" P Natl Acad Sci USA 95:8910-8915 (Jul. 1998).
Rasmussen et al., "Manufacture of recombinant polyclonal antibodies" Biotechnol Lett 29:845-852 ( 2007).
Reeck et al., "Homology in Proteins and Nucleic Acids: A Terminology Muddle and a Way out of it" Cell 50(5):667 ( 1987).

Repo et al., "Is the bovine lysosomal phospholipase B-like protein an amidase?" Proteins 82:300-311 ( 2014).
Rey et al., "Full automation and validation of a flexible ELISA platform for host cell protein and protein A impurity detection in biopharmaceuticals" J Pharmmaceutical and Biomedical Analysis 70:580-586 ( 2012).
Riechmann et al., "Reshaping human antibodies for therapy" Nature 332:323-327 (Mar. 24, 1988).
Riemer et al., "Matching of trastuzumab (Herceptin) epitope mimics onto the surface of Her-2/neu—a new method of epitope definition" Mol Immunol 42:1121-1124 ( 2005).
Roberg et al., "Treatment of uveitis with recombinant human interleukin-13" B F Ophthalmol 82:1195-1198 ( 1998).
Roitt et al. Roitt's Essential Immunology "Chanter 6" (English Translation),:110-111 ( 2000).
Roitt, I.M. Essential Immunology "Hypersensitivity" 6th edition, oXFORD:Blackwell Scientific Publications,:195-196 ( 1988).
Romer et al., "Efficacy and safety of a new ready-to-use recombinant human growth hormone solution" J Endocrinol Invest 30:578-589 ( 2007).
Rudikoff et al., "Single amino acid substitution altering antigen-binding specificity," Proc. Nat. Acad. Sci. USA, vol. 79, pp. 1979-1983, Mar. 1982.
Saenger, "Current status of biosimilar growth hormone" Int J Pediatric Endrocin:370329 (2009).
Saha et al., "Increased sputum and bronchial biopsy IL-13 expression in severe asthma" J Allergy Clin Immunol:685-691 (Mar. 2008).
Sambrook et al. Molecular Cloning: A Laboratory Manual (Table of Contents only, in 32 pages), 2nd edition, Cold Spring Harbor, NY: Cold Spring Harbor Laboratory Press, ( 1989).
Sandberg et al., "Mapping and partial characterization of proteases expressed by a CHO production cell line" Biotechnol Bioeng 95:961-971 ( 2006).
Santangelo et al., "Detection of antibodies to phospholipase B in patients infected with Cryptococcus neoformans by enzyme-linked immunosorbent assay 9ELISA)" medical mycology 43:335-341 (Jun. 2005).
Schacker et al., "Collagen deposition in HIV-1 infected lymphatic tissues and T cell homeostasis" J Clin Invest 110(8):1133-1139 (Oct. 2002).
Scheerens et al., "The effects of lebrikizumab in patients with mild asthma following whole lung allergen challenge" Clin Exper Allergy 44:38-46 ( 2014).
Schenauer et al., "Identification and quantification of host cell protein impurities in biotherapeutics using mass spectrometry" Analyt Biochem 428:150-157 ( 2012).
Schildbach et al., "Modulation of antibody affinity by a non-contact residue" Protein Science 2:206-214 ( 1993).
Sharma, "Immunogenicity of therapeutic proteins, Part 2: Impact of container closures" Biotechnol Advances 25:318-324 ( 2007).
Shukla et al., "Downstream processing of monoclonal antibodies—application of platform approaches" J Chromatograph B 848:28-39 ( 2007).
Shukla et al., "Host cell protein clearance during protein A chromatography: development of an improved column wash step" Biotechnol Prog 24:1115-1121 ( 2008).
Sims et al., "A Humanized CD18 Antibody Can Block Function Without Cell Destruction" J Immunol 151(4):2296-2308 (Aug. 15, 1993).
Singer et al., "Gens and Genoms" Moscow Mir. ((In Russian with English translation)), 1:63 ( 1988).
Sisodiya et al., "Studying host cell protein interactions with monoclonal antibodies using high throughput protein A chromatography" Biotechnol J 7:1233-1241 ( 2012).
Skerra, A., "Bacterial expression of immunoglobulin fragments" Curr Opin Immunol 5:256-262 ( 1993).
Skinnider et al., "Signal transducer and activator of transcription 6 is frequently activated in Hodgkin and Reed-Sternberg cells of Hodgkin lymphoma" Blood 99(2):618-626 (Jan. 15, 2002).
Skinnider et al., "The role of interleukin 13 in classical Hodgkin lymphoma" Leuk Lymphoma 43(6): 1203-1210 ( 2002).

(56) References Cited

OTHER PUBLICATIONS

Stewart et al. Solid-Phase Peptide Synthesis, San Francisco, CA:W. H. Freeman Co. (1969).
Taber's Cyclopedic Medical Dictionary, "Atopy," p. 170 (1997), 18th Ed., F.A. Davis Company, Philadelphia.
Tait et al., "Host cell protein dynamics in the supernatant of a mAb producing CHO cell line" Biotechnol Bioeng 109(4):971-982 (Apr. 2012).
Tekkanat et al., "IL-13-induced airway hyperreactivity during respiratory syncytial virus infection is STAT6 dependent" J Immunol 166:3542-3548 ( 2001).
Teplyakov et al., "Epitope mapping of anti-interleukin-13 neutralizing antibody CNT0607" J Mol Biol 389:115-123 ( 2009).
Teplyakov et al., "On the domain pairing in chimeric antibodies" Mol Immunol 47:2422-2426 ( 2010).
Terabe et al., "NKT cell-mediated repression of tumor immunosurveillance by IL-13 and the IL-4R-STAT6 pathway" Nat Immunol 1(6):515-520 (Dec. 2000).
Terabe et al., "Role of IL-13 in regulation of anti-tumor immunity and tumor growth" Cancer Immunol Immunother 53:79-85 ( 2004).
Thakrar et al., "Assessing the efficacy and safety of Omnitrope" British J Clin Pharmacy 2:298-301 ( 2010).
Thompson et al., "Mutants of interleukin 13 with altered reactivity toward interleukin 13 receptors" J Biol Chem 274(42):29914-29950 (Oct. 15, 1999).
Thomson et al., "Lebrikizumab in the personalized management of asthma" Biologics: Targets and Therapy 6:329-335 ( 2012).
Tran et al., "Investigating interactions between phospholipase B-like 2 and antibodies during prodein A chromatography" J Chromatograph A 1438:31-38 (2016).
Trieu et al., "Inhibition of Hodgkin lymphoma cell line growth using an adenovirus expressing the soluble IL-13 decoy receptor (sIL-13Ralpha2)" Blood (Abstract No. 2272 only), 100.
Trieu et al., "Soluble interleukin-13R$\alpha$2 decoy receptor inhibits Hodgkin's lymphoma growth in vitro and in vivo" Cancer Res 64:3271-3275 ( 2004).
Triggiani et al., "Activation of human inflammatory cells by secreted phospholipases A $_2$" Biochim Biophys Acta 1761:1289-1300 ( 2006).
Tsarbopoulos et al., "Mass spectrometric mapping of disulfide bonds in recombinant human interleukin-13" J Mass Spectrometry 35:446-453 (2000).
Ultsch et al., "Structural basis of signaling blockade by anti-IL-13 antibody lebrikizumab" J Mol Biol 425:1330-1339 (2013).
Vajdos et al. et al., "Comprehensive functional maps of the antigen-binding site of an anti-ErbB2 antibody obtained with shotgun scanning mutagenesis" J Mol Biol 320(2):415-428 (Jul. 5, 2002).
van Cleave et al., "Validation of immunoassays for anti-drug antibodies" Dev Biol (Basel) 112:107-112 ( 2003).
Van Der Pouw Kraan et al., "Human IL-13 production is negatively influenced by CD3 engagement" J Immunol 156:1818-1823 ( 1996).
Van Der Pouw Kraan et al., "The role of IL-13 in IgE synthesis by allergic asthma patients" Clin Exp Immunol 111:129-135 ( 1998).
Vanderlaan et al., "Hamster phospholipase B-like 2 (PLBL2); A host-cell protein impurity in therapeutic monoclonal antibodies derived from Chinese hamster ovary cells" Bioprocess International 13(4):18 (Apr. 2015).
Venkayya et al., "The Th2 lymphocyte products IL-4 and IL-13 rapidly induce airway hyperresponsiveness through direct effects on resident airway cells" Am J Respir Cell Mol Biol 26:202-208 ( 2002).
Verhoeyen et al., "Reshaping human antibodies: Grafting an antilysozyme activity" Science 239:1534-1536 (Mar. 1988).
Vita et al., "Characterization and comparison of the interleukin 13 receptor with the interleukin 4 receptor on several cell types" J Biol Chem 270(8):3512-3517 ( 1995).
Vugmeyster et al., "Preclinical pharmacokinetics, interspecies scaling, and tissue distribution of humanized monoclonal anti-IL-13 antibodies with different IL-13 nontralization mechanisms" Int Immunopharmacology 8:477-483 ( 2008).

Wang et al., "Host cell proteins in biologics development: Identification, quantitation and risk assessment" Biotechnol Bioeng 103(3):446-458 (Jun. 15, 2009).
Wang et al., "Impact of residual impurities and contaminants on protein stability" J Pharm Sci 103:1315-1330 ( 2014).
Wang et al., "Precipitation of process-drived impurities in non-protein A purification schemes for antibodies" Biopharm Int, Downstream Processing 2010:4-10 (Oct. 2009).
Ward et al., "Binding activities of a repertoire of sigle immunoglobulin variable domains" Nature 341:544-546 (Oct. 12, 1989).
Wardemann et al., "Predominant autoantibody production by early human B cell precursors" Science 301:1374-1377 (Sep. 5, 2003).
Warner, J. O., "Bronchial hyperresponsiveness, atopy, airway inflammation, and asthma" Pediatr Allergy Immunol 9:56-60 ( 2003).
Waterhouse et al., "Combinatorial infection and in vivo recombination: a strategy for making large phage antibody repertoires" Nucl Acids Res 21(9):2265-2266 ( 1993).
Webb, S., "Attacks on asthma" Nat Biotechnol 29(10):860-863 ( 2011).
Wensel et al., "High-throughput screening of chromatographic separations: III. Monoclonal antibodies on ceramic hydroxyapatite" Biotechnol Bioeng 100(5):839-854 (Aug. 1, 2008).
Wikipedia entry for "Hypersensitivity" [on-line], [Retrieved on Jul. 2, 2007], pp. 1-4, Retrieved from the Internet: <URL: http://en.wikipedia.org/wiki/Hypersensitivity>, pp. 1-4 (Jul. 2, 2007).
Wills-Karp et al., "Interleukin-13: Central mediator of allergic asthma" Science 282:2258-2261 ( 1998).
Wills-Karp, "Interleukin-13 in asthma pathogenesis" Curr Allergy Asthma Rep 4(2):123-131 ( 2004).
Winkler et al. et al., "Changing the antigen binding specificity by single point mutations of an anti-p24 (HIV-1) antibody" J Immunol 165:4505-4514 ( 2000).
Wood et al., "Enhanced interleukin (IL)-13 responses in mice lacking IL-13 receptor $\alpha$ 2" J Exp Med 197(6):703—(Mar. 17, 2003).
World Health Organization, "International statistical classification of diseases and related health and related health problems," 10th Revision, 1:535-537 (1992).
Wu et al., "Humanization of a murine monoclonal antibody by simultaneous optimization of framework and CDR residues" J Mol Biol 294(1):151-162 ( 1999).
Wynn, T A, "IL-13 effector functions" Annu. Rev Immunol 21:425-456 ( 2003).
Xu et al., "The genomic sequence of the Chinese hamster ovary (CHO)-K1 cell line" Nature Biotechnol 29(8):735-741 (Aug. 2011).
Xue et al., "Prevalence and isotypic complexity of the anti-Chinese hamster ovary host cell protein antibodies in normal human serum" AAPS J 12(1):98-106 (Mar. 2010).
Yang et al., "Anti-IL-13 monoclonal antibody inhibits airway hyper-responsiyeness, inflammation and airway remodeling" Cytokine 28:224-232 (2004).
Yang et al., "Therapeutic dosing with anti-interleukin-13 monoclonal antibody inhibits asthma progression in mice" J Pharmacol Exp Ther 312:8-15 (2005).
Yssel et al., "The Role of IgE in Asthma" Clinical and Experimental Allergy 28(Supplement 5):104-109 (1998).
Zafra et al., "Host cell proteins in biotechnology-derived products: A risk assessment framework" Biotechnol Bioeng 112(11):2284-2291 (Nov. 2015).
Zapata et al., "Engineering linear F(ab') $_2$ fragments for efficient production in *Escherichia coli* and enhanced antiproliferative activity" Protein Eng 8(10):1057-1062 ( 1995).
Zhang et al., "Identification, purification, and characterization of a soluble interleukin (IL)-13-binding protein" J Biol Chem 272(14):9474-9480 (Apr. 4, 1997).
Zhu et al., "A rapid cIEF-ESI-MS/MS method for host cell protein analysis of a recombinant human monoclonal antibody" Talanta 98:253-256 (2012).
Zhu-Shimoni et al., "Host Cell Protein Testing by ELISAs and the Use of Orthogonal Methods" Biotechnol. Bioeng. 111(12):2367-2379 (Dec. 2014).

(56) References Cited

OTHER PUBLICATIONS

Zuegg et al., "Structural model of human IL-13 defines the spatial interactions with the IL-13Rα/IL-4Rα receptor" Immunol Cell Biol 79:332-339 (2001).
Marek et al., "Isolation of monoclonal antibody from a Chinese hamster ovary supernatant. I: Assessment of different separation concepts" Journal of Chromatography A 1305:55-63 (2013).
Adolfsson, O. et al., "An Effector-Reduced Anti-β-Amyloid (Aβ) Antibody with Unique Aβ Binding Properties Promotes Neuroprotection and Glial Engulfment of Aβ", The Journal of Neuroscience, vol. 32, No. 28, Jul. 11, 2012, pp. 9677-9689.
Barghorn, S. et al., "Globular Amyloid β-Peptide$_{1-42}$ Oligomer—A Homogenous and Stable Neuropathological Protein in Alzheimer's Disease", Journal of Neurochemistry, vol. 95, 2005, pp. 834-847.
Hogwood, C. et al., "The Dynamics of the CHO Host Cell Protein Profile During Clarification and Protein A Capture in a Platform Antibody Purification Process", Biotechnology and Bioengineering, vol. 110, No. 1, Jan. 2013, pp. 240-251.

\* cited by examiner

SEQUENCE LISTING

<160> NUMBER OF SEQ ID NOS: 32

<210> SEQ ID NO 1
<211> LENGTH: 1758
<212> TYPE: DNA
<213> ORGANISM: Cricetulus griseus

<400> SEQUENCE: 1

```
atggcggccc ccatggaccg gagccccggc ggccgggcgg tccgggcgct gaggctagcg      60
ctggcgctgg cctcgctgac tgaggtgttg ctgaattgcc ggcgggcgc cctcccacg      120
caggggcccg gcaggcggcg ccaaaacctc gacccgccgg tctcccgcgt ccgctcggtg      180
ctgctggacg ccgcgtcggg tcagctgcgc ctggtggacg gcatccatcc ctacgcggtg      240
gcctgggcca acctcaccaa cgccattcgc gagaccgggt gggcctatct ggacttgggt      300
acaaatggaa gctacaatga cagcctgcag gcctatgcag ctggtgtggt ggaggcttct      360
gtgtctgagg agctcatcta catgcactgg atgaacacaa tggtcaacta ctgtggcccc      420
```

```
ttcgagtatg aagttggcta ctgtgagaag ctcaagagct tcctggagat caacctggag    480
tggatgcaga gggagatgga actcagccag gactctccat attggcacca ggtgcggctg    540
accctcctgc agctgaaagg cctagaggac agctacgaag gccgtttgac cttcccaact    600
gggaggttca ccattaaacc cttggggttc ctcctgctgc agattgccgg agacctggaa    660
gacctagagc aagccctgaa taagaccagc accaagcttt ccctgggctc cggttcctgc    720
tccgctatca tcaagttgct gccaggcgca cgtgacctcc tggtggcaca caacacatgg    780
aactcctacc agaacatgct acgcatcatc aagaagtacc agctgcagtt ccggcagggg    840
cctcaagagg cgtaccccct gattgctggc aacaatttgg tcttttcgtc ttacccgggc    900
accatcttct ctggcgatga cttctacatc ctgggcagtg ggctggtcac cctggagacc    960
accattggca caagaatcc agccctgtgg aagtacgtgc agcccagggg ctgtgtgctg   1020
gagtggattc gaaacatcgt ggccaaccgc ctggccttgg acggggccac ctgggcagac   1080
atcttcaagc agttcaatag tggcacgtat aataaccaat ggatgattgt ggactacaag   1140
gcattcatcc ccaacgggcc cagccctgga agccgagtgc ttaccatcct agaacagatc   1200
ccgggcatgg tggtggtggc cgacaagact gaagatctct acaagacaac ctactgggct   1260
agctacaaca tcccgttctt tgagattgtg ttcaacgcca gtgggctgca ggacttggtg   1320
gcccaatatg gagattggtt ttcctacact aagaaccctc gagctcagat cttccagagg   1380
gaccagtcgc tggtggagga catgaattcc atggtccggc tcataaggta caacaacttc   1440
cttcacgacc ctctgtcact gtgtgaagcc tgtatcccga gcccaatgc agagaatgcc   1500 atctctgccc gctctgacct caatcctgcc aatggctcct acccatttca gccctgtac    1560 cagcgtcccc acggtggcat cgatgtgaag gtgaccagct tttcactggc caagcgcatg   1620
agcatgctgg cagccagtgg cccaacgtgg gatcagttgc ccccattcca gtggagttta   1680
tcgccgttcc gcagcatgct tcacatgggc cagcctgatc tctggacatt ctcacccatc   1740
agtgtcccat gggactga                                                 1758
```

<210> SEQ ID NO 2
<211> LENGTH: 585
<212> TYPE: PRT
<213> ORGANISM: Cricetulus griseus

<400> SEQUENCE: 2

Met Ala Ala Pro Met Asp Arg Ser Pro Gly Gly Arg Ala Val Arg Ala
1               5                   10                  15

Leu Arg Leu Ala Leu Ala Leu Ala Ser Leu Thr Glu Val Leu Leu Asn
            20                  25                  30

Cys Pro Ala Gly Ala Leu Pro Thr Gln Gly Pro Gly Arg Arg Arg Gln
        35                  40                  45

Asn Leu Asp Pro Pro Val Ser Arg Val Arg Ser Val Leu Leu Asp Ala
    50                  55                  60

Ala Ser Gly Gln Leu Arg Leu Val Asp Gly Ile His Pro Tyr Ala Val
65                  70                  75                  80

Ala Trp Ala Asn Leu Thr Asn Ala Ile Arg Glu Thr Gly Trp Ala Tyr
                85                  90                  95

Leu Asp Leu Gly Thr Asn Gly Ser Tyr Asn Asp Ser Leu Gln Ala Tyr
            100                 105                 110

Ala Ala Gly Val Val Glu Ala Ser Val Ser Glu Glu Leu Ile Tyr Met
        115                 120                 125

His Trp Met Asn Thr Met Val Asn Tyr Cys Gly Pro Phe Glu Tyr Glu

```
            130                 135                 140
Val Gly Tyr Cys Glu Lys Leu Lys Ser Phe Leu Glu Ile Asn Leu Glu
145                 150                 155                 160

Trp Met Gln Arg Glu Met Glu Leu Ser Gln Asp Ser Pro Tyr Trp His
                165                 170                 175

Gln Val Arg Leu Thr Leu Leu Gln Leu Lys Gly Leu Glu Asp Ser Tyr
                180                 185                 190

Glu Gly Arg Leu Thr Phe Pro Thr Gly Arg Phe Thr Ile Lys Pro Leu
                195                 200                 205

Gly Phe Leu Leu Leu Gln Ile Ala Gly Asp Leu Glu Asp Leu Glu Gln
210                 215                 220

Ala Leu Asn Lys Thr Ser Thr Lys Leu Ser Leu Gly Ser Gly Ser Cys
225                 230                 235                 240

Ser Ala Ile Ile Lys Leu Leu Pro Gly Ala Arg Asp Leu Leu Val Ala
                245                 250                 255

His Asn Thr Trp Asn Ser Tyr Gln Asn Met Leu Arg Ile Ile Lys Lys
                260                 265                 270

Tyr Gln Leu Gln Phe Arg Gln Gly Pro Gln Glu Ala Tyr Pro Leu Ile
                275                 280                 285

Ala Gly Asn Asn Leu Val Phe Ser Ser Tyr Pro Gly Thr Ile Phe Ser
                290                 295                 300

Gly Asp Asp Phe Tyr Ile Leu Gly Ser Gly Leu Val Thr Leu Glu Thr
305                 310                 315                 320

Thr Ile Gly Asn Lys Asn Pro Ala Leu Trp Lys Tyr Val Gln Pro Gln
                325                 330                 335

Gly Cys Val Leu Glu Trp Ile Arg Asn Ile Val Ala Asn Arg Leu Ala
                340                 345                 350

Leu Asp Gly Ala Thr Trp Ala Asp Ile Phe Lys Gln Phe Asn Ser Gly
                355                 360                 365

Thr Tyr Asn Asn Gln Trp Met Ile Val Asp Tyr Lys Ala Phe Ile Pro
                370                 375                 380

Asn Gly Pro Ser Pro Gly Ser Arg Val Leu Thr Ile Leu Glu Gln Ile
385                 390                 395                 400

Pro Gly Met Val Val Ala Asp Lys Thr Glu Asp Leu Tyr Lys Thr
                405                 410                 415

Thr Tyr Trp Ala Ser Tyr Asn Ile Pro Phe Phe Glu Ile Val Phe Asn
                420                 425                 430

Ala Ser Gly Leu Gln Asp Leu Val Ala Gln Tyr Gly Asp Trp Phe Ser
                435                 440                 445

Tyr Thr Lys Asn Pro Arg Ala Gln Ile Phe Gln Arg Asp Gln Ser Leu
                450                 455                 460

Val Glu Asp Met Asn Ser Met Val Arg Leu Ile Arg Tyr Asn Asn Phe
465                 470                 475                 480

Leu His Asp Pro Leu Ser Leu Cys Glu Ala Cys Ile Pro Lys Pro Asn
                485                 490                 495

Ala Glu Asn Ala Ile Ser Ala Arg Ser Asp Leu Asn Pro Ala Asn Gly
                500                 505                 510

Ser Tyr Pro Phe Gln Ala Leu Tyr Gln Arg Pro His Gly Gly Ile Asp
                515                 520                 525

Val Lys Val Thr Ser Phe Ser Leu Ala Lys Arg Met Ser Met Leu Ala
                530                 535                 540

Ala Ser Gly Pro Thr Trp Asp Gln Leu Pro Pro Phe Gln Trp Ser Leu
545                 550                 555                 560
```

```
Ser Pro Phe Arg Ser Met Leu His Met Gly Gln Pro Asp Leu Trp Thr
            565                 570                 575

Phe Ser Pro Ile Ser Val Pro Trp Asp
            580                 585

<210> SEQ ID NO 3
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Lys Leu Glu Glu Ser Gly Gly Gly Leu Val Gln Pro Gly Gly
1               5                   10                  15

Ser Thr Lys Leu Ser Cys Ala Ala Ser Gly Phe Thr Phe Ser Asp Ala
            20                  25                  30

Trp Met Asp Trp Val Arg Gln Cys Pro Glu Lys Gly Leu Glu Trp Val
        35                  40                  45

Ala Glu Ile Ser Ser Lys Ala Asn Asn Arg Ala Thr Tyr Tyr Ala Glu
50                  55                  60

Ser Val Lys Gly Arg Phe Thr Ile Ser Arg Asp Asp Ser Lys Ser Cys
65                  70                  75                  80

Val Tyr Leu Gln Met Asn Ser Leu Arg Ala Glu Asp Thr Gly Ile Tyr
                85                  90                  95

Tyr Cys Thr Arg Arg Gly Tyr Thr Met Asp Tyr Trp Gly Gln Gly Thr
            100                 105                 110

Ser Val Thr Val Ser Ser Ala Ser Thr Lys Gly Pro Ser Val Tyr Pro
        115                 120                 125

Leu Ala Pro Gly Ser Ala Ala Gln Thr Asn Ser Met Val Thr Leu Gly
130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
```

```
                    325                 330                 335
Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
            370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
            435                 440

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Lys Leu Glu Glu Ser Gly Gly Gly Leu Val Gln Pro Gly Gly
1               5                   10                  15

Ser Thr Lys Leu Ser Cys Ala Ala Ser Gly Phe Thr Phe Ser Asp Ala
            20                  25                  30

Trp Met Asp Trp Val Arg Gln Cys Pro Glu Lys Gly Leu Glu Trp Val
        35                  40                  45

Ala Glu Ile Ser Ser Lys Ala Asn Asn Arg Ala Thr Tyr Tyr Ala Glu
    50                  55                  60

Ser Val Lys Gly Arg Phe Thr Ile Ser Arg Asp Asp Ser Lys Ser Cys
65                  70                  75                  80

Val Tyr Leu Gln Met Asn Ser Leu Arg Ala Glu Asp Thr Gly Ile Tyr
                85                  90                  95

Tyr Cys Thr Arg Arg Gly Tyr Thr Met Asp Tyr Trp Gly Gln Gly Thr
            100                 105                 110

Ser Val Thr Val Ser Ser
        115

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Thr Phe Ser Asp Ala Trp Met Asp
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 6

Glu Ile Ser Ser Lys Ala Asn Asn Arg Ala Thr Tyr Tyr Ala Glu Ser
1               5                   10                  15

Val Lys Gly

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Arg Arg Gly Tyr Thr Met Asp Tyr
1               5

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
                20                  25                  30

Val Ala Trp Tyr Gln Gln Lys Pro Gly Gln Ser Pro Lys Ala Leu Ile
            35                  40                  45

Phe Ser Ala Ser Tyr Arg Phe Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Phe Pro Phe
                85                  90                  95

Thr Phe Gly Ser Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 9
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Phe Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Phe Pro Phe
                85                  90                  95

Thr Phe Gly Ser Gly Thr Lys Leu Glu Leu Lys
            100                 105

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ala Ser Gln Asn Val Asp Thr Asn Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ala Ser Tyr Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Tyr Asn Asn Phe Pro Phe Thr
1               5

<210> SEQ ID NO 13
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 13

```
Glu Val Gln Leu Gln Glu Ser Gly Pro Cys Leu Val Lys Pro Ser Gln
 1               5                  10                  15
Thr Leu Ser Leu Thr Cys Ser Val Thr Gly Asp Ser Ile Thr Ser Gly
            20                  25                  30
Tyr Trp Asn Trp Ile Arg Lys Phe Pro Gly Asn Lys Leu Glu Ser Met
        35                  40                  45
Gly Tyr Ile Ser Tyr Ser Gly Ser Thr Tyr Tyr Asn Pro Ser Leu Lys
 50                  55                  60
Ser Arg Ile Ser Ile Thr Arg Asp Thr Ser Lys Asn Gln Tyr Tyr Leu
 65                  70                  75                  80
Gln Leu Asn Ser Val Thr Thr Glu Asp Thr Ala Thr Tyr Tyr Cys Ala
                85                  90                  95
Arg Ile Ala Ser Trp Ile Thr Thr Tyr Phe Asp Tyr Trp Gly Gln Gly
            100                 105                 110
Thr Thr Leu Thr Val Ser Ser Ala Ser Thr Lys Gly Pro Ser Val Tyr
        115                 120                 125
Pro Leu Ala Pro Gly Ser Ala Ala Gln Thr Asn Ser Met Val Thr Leu
130                 135                 140
Gly Cys Leu Val Lys Gly Tyr Phe Pro Glu Pro Val Thr Val Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Ser Val Thr Val Pro Ser Ser
            180                 185                 190
Thr Trp Pro Ser Glu Thr Val Thr Cys Asn Val Ala His Pro Ala Ser
        195                 200                 205
Ser Thr Lys Val Asp Lys Lys Ile Val Pro Arg Asp Cys Gly Cys Lys
210                 215                 220
Pro Cys Ile Cys Thr Val Pro Glu Val Ser Ser Val Phe Ile Phe Pro
225                 230                 235                 240
Pro Lys Pro Lys Asp Val Leu Thr Ile Thr Leu Thr Pro Lys Val Thr
                245                 250                 255
Cys Val Val Val Asp Ile Ser Lys Asp Asp Pro Glu Val Gln Phe Ser
            260                 265                 270
Trp Phe Val Asp Asp Val Glu Val His Thr Ala Gln Thr Gln Pro Arg
        275                 280                 285
Glu Glu Gln Phe Asn Ser Thr Phe Arg Ser Val Ser Glu Leu Pro Ile
290                 295                 300
Met His Gln Asp Trp Leu Asn Gly Lys Glu Phe Lys Cys Arg Val Asn
305                 310                 315                 320
Ser Ala Ala Phe Pro Ala Pro Ile Glu Lys Thr Ile Ser Lys Thr Lys
                325                 330                 335
Gly Arg Pro Lys Ala Pro Gln Val Tyr Thr Ile Pro Pro Lys Glu
            340                 345                 350
Gln Met Ala Lys Asp Lys Val Ser Leu Thr Cys Met Ile Thr Asp Phe
        355                 360                 365
Phe Pro Glu Asp Ile Thr Val Glu Trp Gln Trp Asn Gly Gln Pro Ala
370                 375                 380
Glu Asn Tyr Lys Asn Thr Gln Pro Ile Met Asp Thr Asp Gly Ser Tyr
385                 390                 395                 400
Phe Val Tyr Ser Lys Leu Asn Val Gln Lys Ser Asn Trp Glu Ala Gly
```

```
                    405                 410                 415
Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Gln Glu Ser Gly Pro Cys Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Ser Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Ile Ala Ser Trp Ile Thr Thr Tyr Phe Asp Tyr Trp Gly Gln Gly
            100                 105                 110

Thr Thr Leu Thr Val Ser Ser
        115

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Asp Ser Ile Thr Ser Gly Tyr Trp Asn
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Ile Ser Tyr Ser Gly Ser Thr Tyr Tyr Asn Pro Ser Leu Lys Ser
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 17

Ala Arg Ile Ala Ser Trp Ile Thr Thr Tyr Phe Asp Tyr
1               5                   10

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Met Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Arg Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Ile Leu Ser Ile Asn Ser Val Glu Ser
65                  70                  75                  80

Glu Asp Ile Ala Asp Tyr Tyr Cys Gln Gln Ser Asn Ser Trp Pro Tyr
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Met Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Arg Asn Gly Ser Pro Arg Leu Leu Ile
        35                  40                  45

```
Lys Tyr Ala Ser Glu Ser Ile Ser Gly Ile Pro Ser Arg Phe Ser Gly
        50                  55                  60

Ser Gly Ser Gly Thr Asp Phe Ile Leu Ser Ile Asn Ser Val Glu Ser
 65                  70                  75                  80

Glu Asp Ile Ala Asp Tyr Tyr Cys Gln Gln Ser Asn Ser Trp Pro Tyr
                 85                  90                  95

Thr Phe Gly Gly Gly Thr Lys Leu Glu Leu Lys
            100                 105

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ala Ser Gln Ser Ile Gly Thr Ser Ile His
 1               5                  10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Ala Ser Glu Ser Ile Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Ser Asn Ser Trp Pro Tyr Thr
 1               5

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
actggagcgt acgctgaagt gaagcttgag gagtct                        36

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aagaccgatg ggcccttggt ggaggctgag gagacggtga ctgaggttc          49
```

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
actggagcgt acgctgaggt gcagcttcag gagtca                36

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
aagaccgatg ggcccttggt ggaggctgag gagactgtga gagtggtgc        49

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gcaactgcaa ccggtgtaca ttcagacatt gtgatgaccc agtct            45

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggtgcagcca cggtccgctt cagctccagc ttggtacc                   38

<210> SEQ ID NO 29
<211> LENGTH: 12
<212> TYPE: PRT
<213> ORGANISM: Cricetulus griseus

<400> SEQUENCE: 29

Ser Val Leu Leu Asp Ala Ala Ser Gly Gln Leu Arg
1               5                   10

<210> SEQ ID NO 30
<211> LENGTH: 9
<212> TYPE: PRT
<213> ORGANISM: Cricetulus griseus

<400> SEQUENCE: 30

Gly Leu Glu Asp Ser Tyr Glu Gly Arg
1               5

<210> SEQ ID NO 31
<211> LENGTH: 12
<212> TYPE: PRT

```
<213> ORGANISM: Cricetulus griseus

<400> SEQUENCE: 31

Ala Phe Ile Pro Asn Gly Pro Ser Pro Gly Ser Arg
1               5                   10

<210> SEQ ID NO 32
<211> LENGTH: 8
<212> TYPE: PRT
<213> ORGANISM: Cricetulus griseus

<400> SEQUENCE: 32

Val Thr Ser Phe Ser Leu Ala Lys
1               5
```

COMPOSITIONS AND METHODS FOR DETECTING AND QUANTIFYING HOST CELL PROTEIN IN CELL LINES AND RECOMBINANT POLYPEPTIDE PRODUCTS

CROSS REFERENCE TO RELATED APPLICATIONS

This application is a divisional of U.S. application Ser. No. 15/065,615, filed Mar. 9, 2016, which is a continuation of International Application No. PCT/US2014/055382 having an international filing date of Sep. 12, 2014, which claims the benefit of priority of provisional U.S. Application No. 61/991,228 filed May 9, 2014 and provisional U.S. Application No. 61/877,503 filed Sep. 13, 2013, each of which is hereby incorporated by reference in its entirety for any purpose.

SEQUENCE LISTING

The instant application contains a Sequence Listing which has been submitted via EFS-Web and is hereby incorporated by reference in its entirety. Said ASCII copy, created on Mar. 6, 2018, is named P05701_US_SequenceListing.txt and is 28,965 bytes in size.

FIELD

Monoclonal and polyclonal antibodies that bind hamster phospholipase B-like 2 are provided. Also provided are methods for detecting and quantifying hamster phospholipase B-like 2, for example, in recombinant polypeptide preparations, as well as kits for carrying out such methods. Methods of screening or selecting host cell lines or recombinant polypeptide-expressing cell lines that express low levels of hamster phospholipase B-like 2 are also provided.

BACKGROUND

For recombinant biopharmaceutical proteins to be acceptable for administration to human patients, it is important that residual impurities resulting from the manufacture and purification process are removed from the final biological product. These process components include culture medium proteins, immunoglobulin affinity ligands, viruses, endotoxin, DNA, and host cell proteins. These host cell impurities include process-specific host cell proteins (HCPs), which are process-related impurities/contaminants in the biologics derived from recombinant DNA technology. While HCPs are typically present in the final drug substance in small quantities (in parts-per-million or nanograms per milligram of the intended recombinant protein), it is recognized that HCPs are undesirable and their quantities should be minimized. For example, the U.S. Food and Drug Administration (FDA) requires that biopharmaceuticals intended for in vivo human use should be as free as possible of extraneous impurities, and requires tests for detection and quantitation of potential contaminants/impurities, such as HCPs. In addition, the International Conference on Harmonization (ICH) provides guidelines on test procedures and acceptance criteria for biotechnological/biological products. The guidelines suggest that for HCPs, a sensitive immunoassay capable of detecting a wide range of protein impurities be utilized. Although we and others have developed assays and reagents to detect immunoglobulins, DNA, endotoxins, viruses, and total HCPs, e.g., total Chinese hamster ovary proteins (CHOP) (reviewed in Chen A B, J Biotechnol in Healthcare 3:70-80 (1996); Krawitz et al., Proteomics 6:94-110 (2006)), there are currently no commercial reagents or analytical methods of sufficient specificity and sensitivity for the detection and quantification of single process-specific HCPs in recombinant protein preparations, such as immunoglobulin products, including those that co-purify with recombinant protein preparations.

In certain instances, significant dilution dependence may be observed when using immunoassays for the detection and quantification of total HCPs, e.g., total CHOP, suggesting such assays are not appropriate test procedures for accurate quantification of HCP impurities in a particular product. Investigation of such dilution dependence is important so as to enable the development of more appropriate test procedures. In certain instances, dilution dependence can be caused by "antigen excess" in which a single HCP species present in excess of the available antibodies accounts for the observed effects on assay performance (Anicetti et al., J. Immunol. Methods 91:213-224 (1986); Chen A B, J Biotechnol in Healthcare 3:70-80 (1996), Wang X, et al., Biotechnol Bioeng. 103(3):446-58 (2009)).

Sensitive analytical methods, such as LC-MS/MS can be used to identify and quantify single HCP species present in excess of available antibodies. Upon identification of such single HCP species, alternative assays of sufficient sensitivity and specificity and that are capable of being validated for approval by regulatory authorities and that can be used as a platform across multiple recombinant protein products, need to be developed.

In certain of our recombinant protein preparations produced in CHO cells, we identified an enzyme, phospholipase B-like 2, as a single CHOP species present in excess of available antibodies in a total CHOP ELISA assay. As used herein, "PLB2" and "PLBL2" and "PLBD2" are used interchangeably and refer to the enzyme "phospholipase B-like 2" or its synonym, "phospholipase B-domain-like 2". Certain scientific publications on PLBL2 include Lakomek, K. et al., BMC Structural Biology 9:56 (2009); Deuschl, et al., FEBS Lett 580:5747-5752 (2006). PLBL2 is synthesized as a pre-pro-enzyme with parent MW of about 66,000. There is an initial leader sequence which is removed and potential 6 mannose-6-phosphate (M-6-P) groups are added during post-translational modification. M-6-P is a targeting modification that directs this enzyme to the lysosome via the M-6-P receptor. PLBL2 contains 6 cysteines, two of which have free sulfhydrals, and four form disulfide bonds. In acidic environments, PLBL2 is further clipped into the N- and C-terminal fragments having 32,000 and 45,000 MW, respectively. By analogy with other lysosomal enzymes, this cleavage is an activating step, allowing and access of the substrate to the active site.

There is about 80% PLBL2 amino acid sequence homology between hamster and human forms of the enzyme. The enzyme activity is thought to be to cleave either fatty acid chain from the phospholipids that make up cell membranes. There are other phospholipases with different substrate cleavage specificities. Similar enzymatic activities exist in microorganisms, where they are often a virulence factor. Although microorganisms have a similar enzymatic activity, the protein generating this activity is different, and there is low sequence homology between microbial and mammalian PLBL2 enzymes. Phospholipases produce free fatty acids (FFA) as one product of the substrate hydrolysis. Free fatty acids are themselves a potential immune-signaling factor. Dehydrogenation converts FFA to arachadonic acid which potentially participates in inflammation cascades involving eicosanoids.

Having identified PLBL2 as a single HCP (CHOP) in certain recombinant protein preparations, it would be highly advantageous and desirable to have reagents, methods, and kits for the specific, sensitive, and quantitative determination of PLBL2 levels in cell lines or in multiple products and at various stages of purification. Such reagents, methods and kits are particularly needed where there are no existing assays of sufficient consistency, sensitivity, specificity or efficiency. The invention described herein meets certain of the above-described needs and provides other benefits.

All references cited herein, including patent applications and publications, are incorporated by reference in their entirety.

SUMMARY

The invention is based, at least in part, on anti-hamster phospholipase B-like 2 (PLBL2) antibodies and the use of such antibodies in immunoassay methods for the detection and quantification of hamsterPLBL2 protein, for example, in samples obtained from recombinant polypeptide preparations or host cell lines.

Accordingly, in one aspect, an antibody that binds hamster phospholipase B-like 2 is provided. In certain embodiments, the antibody is monoclonal. In certain embodiments, the antibody demonstrates specific binding to hamster PLBL2. In certain embodiments, the antibody comprises a variable region comprising a variable heavy chain region comprising CDRH1 comprising the amino acid sequence of SEQ ID NO: 15, CDRH2 comprising the amino acid sequence of SEQ ID NO: 16, and CDRH3 comprising the amino acid sequence of SEQ ID NO: 17. In certain embodiments, the antibody comprises a variable region comprising a variable light chain region comprising CDRL1 comprising the amino acid sequence of SEQ ID NO: 20, CDRL2 comprising the amino acid sequence of SEQ ID NO: 21, and CDRL3 comprising the amino acid sequence of SEQ ID NO: 22. In certain embodiments, the antibody comprises a variable region comprising a variable heavy chain region comprising CDRH1 comprising the amino acid sequence of SEQ ID NO: 15, CDRH2 comprising the amino acid sequence of SEQ ID NO: 16, and CDRH3 comprising the amino acid sequence of SEQ ID NO: 17 and a variable light chain region comprising CDRL1 comprising the amino acid sequence of SEQ ID NO: 20, CDRL2 comprising the amino acid sequence of SEQ ID NO: 21, and CDRL3 comprising the amino acid sequence of SEQ ID NO: 22. In certain embodiments, the antibody comprises a variable heavy chain region comprising the amino acid sequence of SEQ ID NO: 14. In certain embodiments, the antibody comprises a variable light chain region comprising the amino acid sequence of SEQ ID NO: 19. In certain embodiments, the antibody comprises a variable region comprising a variable heavy chain region comprising the amino acid sequence of SEQ ID NO: 14 and a variable light chain region comprising the amino acid sequence of SEQ ID NO: 19. In certain embodiments, the antibody comprises a heavy chain comprising the amino acid sequence of SEQ ID NO: 13 and a light chain comprising the amino acid sequence of SEQ ID NO: 18. In certain embodiments, the antibody is 19C10.

In another aspect, another antibody that binds hamster phospholipase B-like 2 is provided. In certain embodiments, the antibody is monoclonal. In certain embodiments, the antibody demonstrates specific binding to hamster PLBL2. In certain embodiments, the antibody comprises a variable region comprising a variable heavy chain region comprising CDRH1 comprising the amino acid sequence of SEQ ID NO: 5, CDRH2 comprising the amino acid sequence of SEQ ID NO: 6, and CDRH3 comprising the amino acid sequence of SEQ ID NO: 7. In certain embodiments, the antibody comprises a variable region comprising a variable light chain region comprising CDRL1 comprising the amino acid sequence of SEQ ID NO: 10, CDRL2 comprising the amino acid sequence of SEQ ID NO: 11, and CDRL3 comprising the amino acid sequence of SEQ ID NO: 12. In certain embodiments, the antibody comprises a variable region comprising a variable heavy chain region comprising CDRH1 comprising the amino acid sequence of SEQ ID NO: 5, CDRH2 comprising the amino acid sequence of SEQ ID NO: 6, and CDRH3 comprising the amino acid sequence of SEQ ID NO: 7 and a variable light chain region comprising CDRL1 comprising the amino acid sequence of SEQ ID NO: 10, CDRL2 comprising the amino acid sequence of SEQ ID NO: 11, and CDRL3 comprising the amino acid sequence of SEQ ID NO: 12. In certain embodiments, the antibody comprises a variable heavy chain region comprising the amino acid sequence of SEQ ID NO: 4. In certain embodiments, the antibody comprises a variable light chain region comprising the amino acid sequence of SEQ ID NO: 9. In certain embodiments, the antibody comprises a variable region comprising a variable heavy chain region comprising the amino acid sequence of SEQ ID NO: 4 and a variable light chain region comprising the amino acid sequence of SEQ ID NO: 9. In certain embodiments, the antibody comprises a heavy chain comprising the amino acid sequence of SEQ ID NO: 3 and a light chain comprising the amino acid sequence of SEQ ID NO: 8. In some embodiments, the antibody is 15G11.

In still another aspect, polyclonal antibodies that bind hamster phospholipase B-like 2 protein are provided. In certain embodiments, the polyclonal antibody is rabbit.

In yet another aspect, an immunoassay method for detecting hamster phospholipase B-like 2 protein (PLBL2) is provided. In certain embodiments, a sample from a recombinant polypeptide preparation or a host cell line is obtained. In certain embodiments, the method comprises (a) contacting a first capture antibody that binds hamster PLBL2 with the sample thereby generating a sample-capture antibody combination material; (b) contacting a second detection antibody that binds hamster PLBL2 with the sample-capture antibody combination material; and (c) detecting the second antibody bound to the sample-capture antibody combination material. In some embodiments, the capture antibody does not compete for binding with the detection antibody. In some embodiments, the capture antibody binds a different epitope than the detection antibody. In certain embodiments, the level of the second detection antibody bound is quantified using a standard titration curve. In certain embodiments, an amount of hamster PLBL2 present in the sample is calculated based on the level of the second detection antibody bound. In some embodiments, the immunoassay is an electrochemiluminescent (ECL) assay. In some embodiments, the immunoassay is a sandwich assay. In some embodiments, the sandwich assay is an enzyme-linked immunosorbent assay (ELISA). In certain embodiments, the capture antibody comprises a variable region comprising a variable heavy chain region comprising CDRH1 comprising the amino acid sequence of SEQ ID NO: 15, CDRH2 comprising the amino acid sequence of SEQ ID NO: 16, and CDRH3 comprising the amino acid sequence of SEQ ID NO: 17. In certain embodiments, the capture antibody comprises a variable region comprising a variable light chain region comprising CDRL1 comprising the amino acid sequence of SEQ ID NO: 20, CDRL2 comprising the amino acid sequence of SEQ ID NO: 21, and CDRL3 comprising the amino acid sequence of SEQ ID NO: 22. In certain embodiments, the capture antibody comprises a variable region comprising a variable heavy chain region comprising CDRH1 comprising the amino acid sequence of SEQ ID NO: 15, CDRH2 comprising the amino acid sequence of SEQ ID NO: 16, and CDRH3 comprising the amino acid sequence of SEQ ID NO: 17 and a variable light chain region comprising CDRL1 comprising the amino acid sequence of SEQ ID NO: 20, CDRL2 comprising the amino acid sequence of SEQ ID NO: 21, and CDRL3 comprising the amino acid sequence of SEQ ID NO: 22. In certain embodiments, the capture antibody comprises a variable heavy chain region comprising the amino acid sequence of SEQ ID NO: 14. In certain embodiments, the capture antibody comprises a variable light chain region comprising the amino acid sequence of SEQ ID NO: 19. In certain embodiments, the capture antibody comprises a variable region comprising a variable heavy chain region comprising the amino acid sequence of SEQ ID NO: 14 and a variable light chain region comprising the amino acid sequence of SEQ ID NO: 19. In certain embodiments, the capture antibody comprises a heavy chain comprising the amino acid sequence of SEQ ID NO: 13 and a light chain comprising the amino acid sequence of SEQ ID NO: 18. In certain embodiments, the capture antibody is 19C10. In certain embodiments, the capture antibody is polyclonal. In certain embodiments, the polyclonal capture antibody is rabbit. In certain embodiments, the detection antibody comprises a variable region comprising a variable heavy chain region comprising CDRH1 comprising the amino acid sequence of SEQ ID NO: 5, CDRH2 comprising the amino acid sequence of SEQ ID NO: 6, and CDRH3 comprising the amino acid sequence of SEQ ID NO: 7. In certain embodiments, the detection antibody comprises a variable region comprising a variable light chain region comprising CDRL1 comprising the amino acid sequence of SEQ ID NO: 10, CDRL2 comprising the amino acid sequence of SEQ ID NO: 11, and CDRL3 comprising the amino acid sequence of SEQ ID NO: 12. In certain embodiments, the detection antibody comprises a variable region comprising a variable heavy chain region comprising CDRH1 comprising the amino acid sequence of SEQ ID NO: 5, CDRH2 comprising the amino acid sequence of SEQ ID NO: 6, and CDRH3 comprising the amino acid sequence of SEQ ID NO: 7 and a variable light chain region comprising CDRL1 comprising the amino acid sequence of SEQ ID NO: 10, CDRL2 comprising the amino acid sequence of SEQ ID NO: 11, and CDRL3 comprising the amino acid sequence of SEQ ID NO: 12. In certain embodiments, the detection antibody comprises a variable heavy chain region comprising the amino acid sequence of SEQ ID NO: 4. In certain embodiments, the detection antibody comprises a variable light chain region comprising the amino acid sequence of SEQ ID NO: 9. In certain embodiments, the detection antibody comprises a variable region comprising a variable heavy chain region comprising the amino acid sequence of SEQ ID NO: 4 and a variable light chain region comprising the amino acid sequence of SEQ ID NO: 9. In certain embodiments, the detection antibody comprises a heavy chain comprising the amino acid sequence of SEQ ID NO: 3 and a light chain comprising the amino acid sequence of SEQ ID NO: 8. In some embodiments, the detection antibody is 15G11. In certain embodiments, the detection antibody is polyclonal. In certain embodiments, the polyclonal detection antibody is rabbit. In certain embodiments, the detection antibody is conjugated to biotin. In certain embodiments, the detection antibody is conjugated to horse radish peroxidase.

In certain embodiments of the above methods, the recombinant polypeptide preparation or the host cell line is obtained from a Chinese Hamster Ovary (CHO) cell line. In certain embodiments, the recombinant polypeptide preparation is harvested cell culture fluid (HCCF). In certain embodiments, the recombinant polypeptide preparation has been subjected to one or more chromatographic purification steps. In certain embodiments, the recombinant polypeptide preparation is final purified product. In some embodiments, the final purified product is drug substance.

In certain further embodiments of the above methods, the recombinant polypeptide in the recombinant polypeptide preparation is an antibody or an immunoadhesin. In certain embodiments, the antibody is a multispecific antibody, a bispecific antibody, a half antibody, or an antibody fragment. In some embodiments, the recombinant polypeptide is IgG. In some embodiments, the recombinant polypeptide is selected from IgG1, IgG2, IgG3, and IgG4. In some embodiments, the recombinant polypeptide is IgG1. In some embodiments, the recombinant polypeptide is IgG4.

In yet another aspect, immunoassay kits for the detection of hamster PLBL2 are provided. In certain embodiments, the kit comprises a capture antibody according to any of the capture antibodies described above and a detection antibody according to any of the detection antibodies described above. In some embodiments, the immunoassay is an ECL immunoassay. In some embodiments, the immunoassay is an ELISA immunoassay.

In one aspect, methods of screening a host cell line for expression of hamster PLBL2 comprising detecting PLBL2 in a sample obtained from the host cell line are provided. In certain embodiments, PLBL2 is detected in the sample by using any of the immunoassay methods for the detection of hamster PLBL2 described above. In some embodiments, the sample is harvested cell culture fluid. In some embodiments, the sample whole cell culture fluid. In certain embodiments, the methods further comprise calculating the amount of hamster PLBL2 in the sample using the immunoassay and calculation methods described above.

In another aspect, methods of selecting an optimal host cell line expressing a low amount of hamster PLBL2 from a group of two or more host cell lines are provided. In some embodiments, an optimal host cell line is selected from a group of three or more host cell lines, or a group of five or more host cell lines, or a group of 10 or more host cell lines, or a group of 20 or more host cell lines. In certain embodiments, the methods comprise: (i) obtaining a host cell line sample from each of the two or more host cell lines; (ii) calculating the amount of PLBL2 in each of the host cell line samples using the immunoassay and calculation methods described above; (iii) comparing the amount of PLBL2 in each of the host cell line samples to the amount of PLBL2 in each of the host cell line samples of the group; (iv) identifying the host cell line sample having the lowest amount of PLBL2 compared to each of the host cell line samples of the group, thereby generating an identified host cell line from the group having the lowest amount of PLBL2; and selecting the identified host cell line of (iv) as the optimal host cell line. In some embodiments, each of the two or more host cell lines are CHO cell lines. In some embodiments, each of the host cell line samples is harvested cell culture fluid. In some embodiments, each of the host cell line samples is whole cell culture fluid.

In still another aspect, methods of screening a recombinant polypeptide-expressing cell line for expression of hamster PLBL2, wherein the recombinant polypeptide-expressing cell line is a product cell line, comprising detecting PLBL2 in a sample obtained from the product cell line are provided. In certain embodiments, PLBL2 is detected in the sample by using any of the immunoassay methods for the detection of hamster PLBL2 described above. In certain embodiments, the methods further comprise using the immunoassay and calculation methods described above. In some embodiments, the methods further comprise screening for expression of product by detecting product and quantifying an amount of product in the sample. In some embodiments, the detecting of product and the quantifying of the amount of product comprises a spectrophotometric method or an affinity chromatography method.

In yet still another aspect, methods of selecting an optimal recombinant polypeptide-expressing cell line expressing a low amount of hamster PLBL2 and a high amount of product from a group of two or more recombinant polypeptide-expressing cell lines, where each of the two or more recombinant polypeptide-expressing cell lines are product cell lines expressing the same product are provided. In some embodiments, an optimal recombinant polypeptide-expressing cell line is selected from a group of two or more, or a group of three or more, or a group of five or more, or a group of 10 or more, or a group of 20 or more lines, or a group of 40 or more recombinant polypeptide-expressing cell lines. In certain embodiments, the methods comprise: (i) obtaining a product cell line sample from each of the two or more product cell lines; (ii) calculating the amount of PLBL2 in each of the product cell line samples using the immunoassay and calculation methods described above; (iii) detecting product and quantifying an amount of product in each of the product cell line samples; (iv) comparing the amount of PLBL2 in each of the product cell line samples to the amount of PLBL2 in each of the product cell line samples of the group; (v) comparing the amount of product in each of the product cell line samples to the amount of product in each of the product cell line samples of the group; (vi) identifying the product cell line sample having the lowest amount of PLBL2 and the highest amount of product compared to each of the product cell line samples of the group, thereby generating an identified product cell line from the group having the lowest amount of PLBL2 and the highest amount of product; and selecting the identified product cell line of (vi) as the optimal product cell line. In certain embodiments, the methods comprise: (i) obtaining a product cell line sample from each of the two or more product cell lines; (ii) calculating the amount of PLBL2 in each of the product cell line samples using the immunoassay and calculation methods described above; (iii) detecting product and quantifying an amount of product in each of the product cell line samples; (iv) calculating a ratio of the amount of PLBL2 to the amount of product for each of the product cell line samples; (v) comparing the ratio calculated for each of the product cell line samples to each of the product cell line samples of the group; (vi) identifying the product cell line sample having the lowest ratio of the group, thereby generating an identified product cell line from the group having the lowest amount of PLBL2 and the highest amount of product; and selecting the identified product cell line of (vi) as the optimal product cell line. In some embodiments, each of the two or more product cell lines are CHO cell lines. In some embodiments, each of the product cell line samples is harvested cell culture fluid.

In certain further embodiments of the above methods, the product expressed by the recombinant protein-expressing cell line is an antibody or an immunoadhesin. In certain embodiments, the antibody is a multispecific antibody, a bispecific antibody, a half antibody or an antibody fragment. In some embodiments, the product is IgG. In some embodiments, the product is selected from IgG1, IgG2, IgG3, and IgG4. In some embodiments, the product is IgG1. In some embodiments, the product is IgG4.

BRIEF DESCRIPTION OF THE DRAWINGS

(FIG. 1A) standard curve generated using USCN ELISA kit; (FIG. 1B) standard curve generated using CUSABIO ELISA kit.

Each cell line was cultured in a singlicate shake flask. The equations provide the linear regression and the coefficient of determination ($R^2$).

Figure 12A:
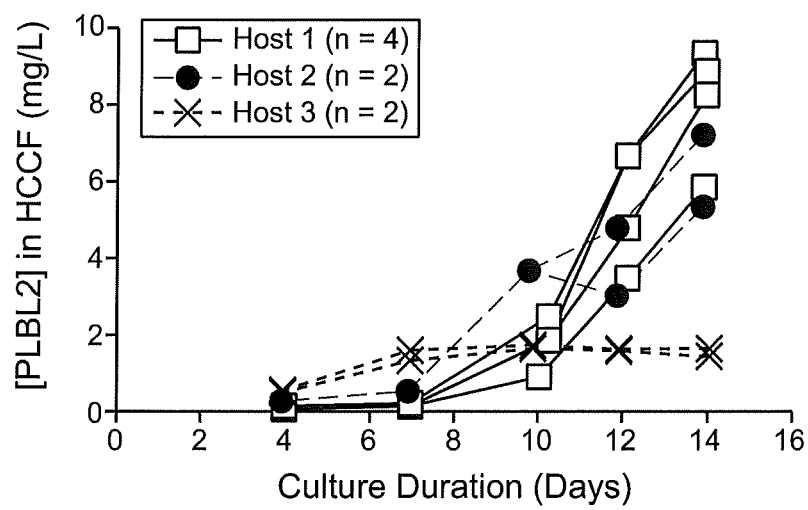
Figure 12B:
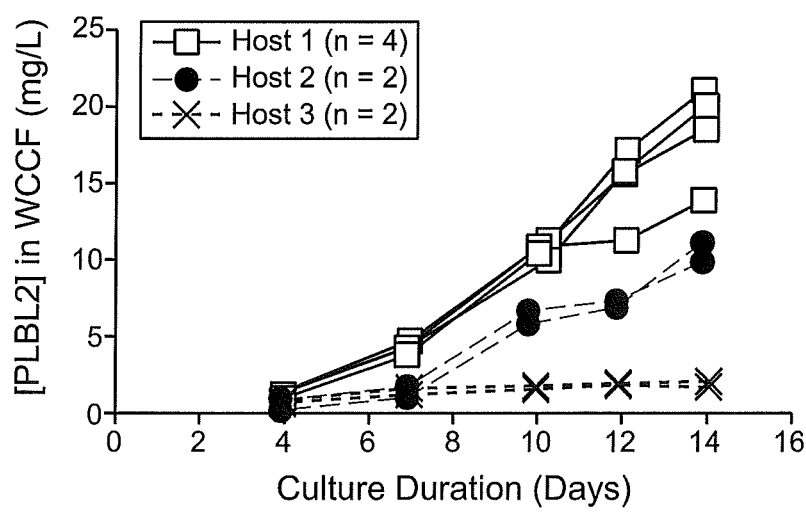

FIGS. 12A and 12B show PLBL2 concentrations in 2 L bioreactor cultures of 3 CHO host cell lines (Host 1, Host 2, and Host 3) that do not express any product genes as described in Example 7. PLBL2 levels were measured in both (FIG. 12A) HCCF and (FIG. 12B) WCCF samples taken from these blank runs.

Figure 13A:
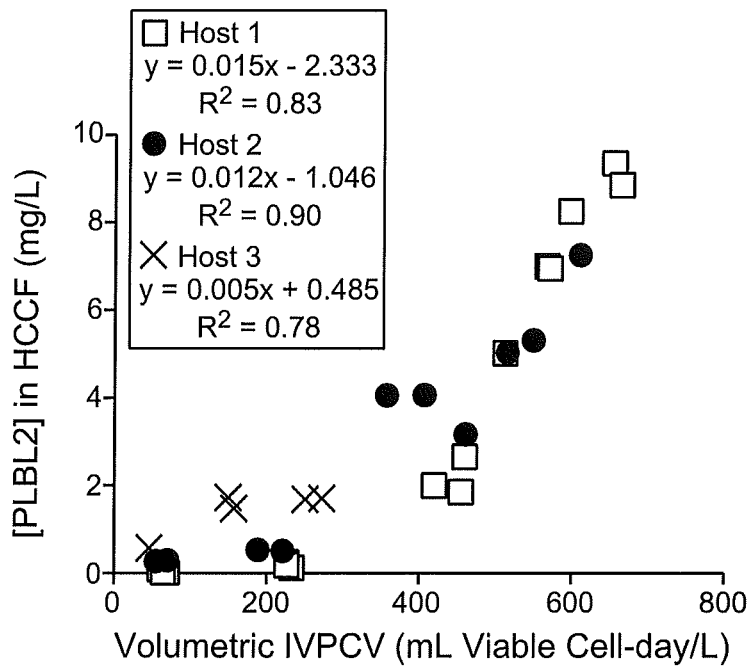
Figure 13B:
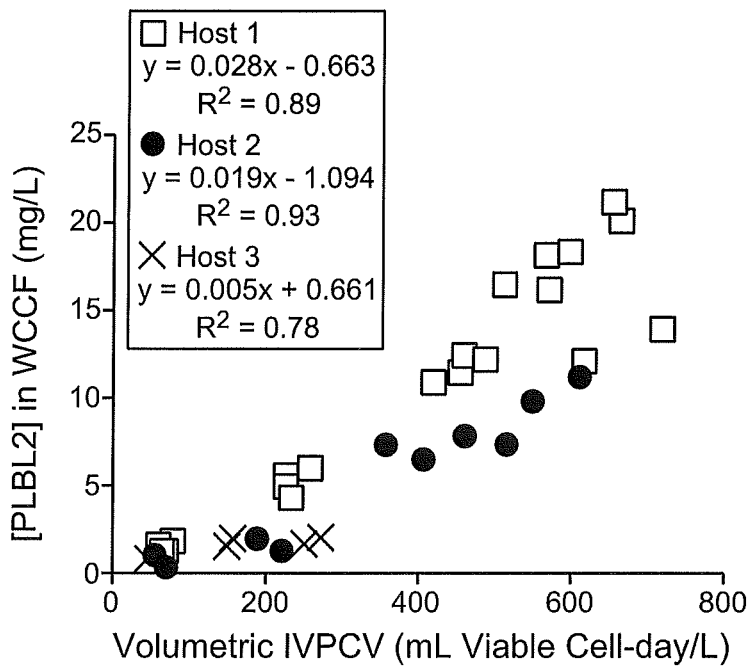

FIGS. 13A and 13B show PLBL2 concentrations in 2 L bioreactor cultures of 3 CHO host cell lines (Host 1, Host 2, and Host 3) as a function of volumetric integrated viable packed cell volume (IVPCV) as described in Example 7. PLBL2 levels were measured in both (FIG. 13A) HCCF and (FIG. 13B) WCCF samples taken from these blank runs. The equations provide the linear regression and the coefficient of determination ($R^2$). The slope of the linear regression provides an estimate of the cell-specific PLBL2 productivity on a per unit viable cell volume per day basis.

DETAILED DESCRIPTION

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" or an "antibody" includes a plurality of proteins or antibodies, respectively; reference to "a cell" includes mixtures of cells, and the like.

The term "detecting" is used herein in the broadest sense to include both qualitative and quantitative measurements of a target molecule. Detecting includes identifying the mere presence of the target molecule in a sample as well as determining whether the target molecule is present in the sample at detectable levels.

A "sample" refers to a small portion of a larger quantity of material. Generally, testing according to the methods described herein is performed on a sample. The sample is typically obtained from a recombinant polypeptide preparation obtained, for example, from cultured recombinant polypeptide-expressing cell lines, also referred to herein as "product cell lines," or from cultured host cells. As used herein, "host cells" do not contain genes for the expression of recombinant polypeptides of interest or products. A sample may be obtained from, for example but not limited to, harvested cell culture fluid, from an in-process pool at a certain step in a purification process, or from the final purified product.

A "capture antibody" refers to an antibody that specifically binds a target molecule in a sample. Under certain conditions, the capture antibody forms a complex with the target molecule such that the antibody-target molecule complex can be separated from the rest of the sample. In certain embodiments, such separation may include washing away substances or material in the sample that did not bind the capture antibody. In certain embodiments, a capture antibody may be attached to a solid support surface, such as, for example but not limited to, a plate or a bead.

A "detection antibody" refers to an antibody that specifically binds a target molecule in a sample or in a sample-capture antibody combination material. Under certain conditions, the detection antibody forms a complex with the target molecule or with a target molecule-capture antibody complex. A detection antibody is capable of being detected either directly through a label, which may be amplified, or indirectly, e.g., through use of another antibody that is labeled and that binds the detection antibody. For direct labeling, the detection antibody is typically conjugated to a moiety that is detectable by some means, for example, including but not limited to, biotin or ruthenium.

The terms "label" or "detectable label" refers to any chemical group or moiety that can be linked to a substance that is to be detected or quantitated, e.g., an antibody. Typically, a label is a detectable label that is suitable for the sensitive detection or quantification of a substance. Examples of detectable labels include, but are not limited to, luminescent labels, e.g., fluorescent, phosphorescent, chemiluminescent, bioluminescent and electrochemiluminescent labels, radioactive labels, enzymes, particles, magnetic substances, electroactive species and the like. Alternatively, a detectable label may signal its presence by participating in specific binding reactions. Examples of such labels include haptens, antibodies, biotin, streptavidin, his-tag, nitrilotriacetic acid, glutathione S-transferase, glutathione and the like.

The term "detection means" refers to a moiety or technique used to detect the presence of the detectable antibody through signal reporting that is then read out in an assay. Typically, detection means employ reagents that amplify an immobilized label such as the label captured onto a microtiter plate, e.g., avidin or streptavidin-HRP.

"Photoluminescence" refers to a process whereby a material luminesces subsequent to the absorption by that material of light (alternatively termed electromagnetic radiation). Fluorescence and phosphorescence are two different types of photoluminescence. "Chemiluminescent" processes involve the creation of the luminescent species by a chemical reaction. "Electro-chemiluminescence" or "ECL" is a process whereby a species, e.g., an antibody, luminesces upon the exposure of that species to electrochemical energy in an appropriate surrounding chemical environment.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

An antibody "which binds" an antigen of interest, e.g. a host cell protein, is one that binds the antigen with sufficient affinity such that the antibody is useful as an assay reagent, e.g., as a capture antibody or as a detection antibody. Typically, such an antibody does not significantly cross-react with other polypeptides.

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a target molecule compared to binding of a control molecule, which generally is a molecule of similar structure that does not have binding activity.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The terms "anti-PLBL2 antibody" and "an antibody that binds to PLBL2" refer to an antibody that is capable of binding PLBL2, e.g., hamster PLBL2 with sufficient affinity such that the antibody is useful as an agent in targeting PLBL2, e.g., as an agent in the assays described herein. In one embodiment, the extent of binding of an anti-PLBL2 antibody to an unrelated, non-PLBL2 protein is less than about 10% of the binding of the antibody to PLBL2 as measured, e.g., by a radioimmunoassay (RIA). In certain embodiments, an antibody that binds to PLBL2 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, and the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the variable or V region. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', F(ab')$_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). In some embodiments, an antigen-binding domain of a multispecific antibody (such as a bispecific antibody) comprises two VH/VL units, wherein a first VH/VL unit specifically binds to a first epitope and a second VH/VL unit specifically binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, antibody fragments such as Fab, Fv, dsFv, scFv, diabodies, bispecific diabodies and triabodies, antibody fragments that have been linked covalently or non-covalently. A VH/VL unit that further comprises at least a portion of a heavy chain constant region and/or at least a portion of a light chain constant region may also be referred to as a "hemimer" or "half antibody." "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

A "bispecific antibody" is a multispecific antibody comprising an antigen-binding domain that is capable of specifically binding to two different epitopes on one biological molecule or is capable of specifically binding to epitopes on two different biological molecules. A bispecific antibody may also be referred to herein as having "dual specificity" or as being "dual specific."

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a detection moiety or label.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "contaminants" and "impurities" are used interchangeably herein and refer to materials or substances that are different from the desired polypeptide product. The contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, such as a Chinese hamster ovary cell, an avian cell, a fungal cell.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-PLBL2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. In certain embodiments, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Assay Methods

Provided herein are immunoassay methods for detection and quantification of hamster PLBL2. Such methods may be used for the detection and quantification of hamster PLBL2 in recombinant polypeptide preparations produced in host cells, for example Chinese hamster ovary cells. In some embodiments, such methods use capture and detection anti-PLBL2 antibodies described herein. In some embodiments, the antibodies are used in any immunoassay method known in the art, including but not limited to, sandwich assay, enzyme-linked immunosorbent assay (ELISA) assay, electrochemical assay (ECL) assay, magnetic immunoassay. In certain embodiments, the method comprises contacting a sample of the recombinant polypeptide preparation with an anti-PLBL2 antibody as described herein under conditions permissive for binding of the anti-PLBL2 antibody to hamster PLBL2, and detecting whether a complex is formed between the anti-PLBL2 antibody and hamster PLBL2.

In certain embodiments, labeled anti-PLBL2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, a capture anti-PLBL2 antibody is immobilized on a solid phase. In some embodiments, the solid phase used for immobilization is any inert support or carrier that is essentially water insoluble and useful in immunometric assays, including supports in the form of, e.g., surfaces, particles, porous matrices, beads and the like. Examples of commonly used supports include small sheets, SEPHADEX®, gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In some embodiments, the immobilized capture reagents are coated on a microtiter plate that can be used to analyze several samples at one time. Exemplary microtiter plates include, but are not limited to, MICROTEST®, MAXISORP®, NUNC MAXISORB®, and IMMULON®. The solid phase is coated with the capture reagents as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for one hour at room temperature. In some embodiments, the plates are stacked and coated long in advance of the assay itself, and then the assay is carried out simultaneously on several samples in a manual, semi-automatic, or automatic fashion, such as by using robotics.

In some embodiments, the coated plates are treated with a blocking agent that binds non-specifically to and saturates the binding sites to prevent unwanted binding of the free ligand to the excess sites on the wells of the plate. Examples of appropriate blocking agents for this purpose include but are not limited to, e.g., gelatin, bovine serum albumin, egg albumin, casein, and non-fat milk. The blocking treatment typically takes place under conditions of ambient temperatures for a period of time, typically about 1-4 hours.

In some embodiments, after coating and blocking, the sample to be analyzed, appropriately diluted, is added to the immobilized phase. Exemplary buffers that may be used for dilution for this purpose include, but are not limited to, (a) phosphate-buffered saline (PBS) containing 0.5% BSA, 0.05% TWEEN 20® detergent (P20), 0.05% PROCLIN® 300 antibiotic, 5 mM EDTA, 0.25% 3-((3-cholamidopropyl) dimethylammonio)-1-propanesulphonate (CHAPS) surfactant, 0.2% beta-gamma globulin, and 0.35M NaCl; (b) PBS containing 0.5% bovine serum albumin (BSA), 0.05% P20, and 0.05% PROCLIN® 300, pH 7; (c) PBS containing 0.5% BSA, 0.05% P20, 0.05% PROCLIN® 300, 5 mM EDTA, and 0.35 M NaCl, pH 6.35; (d) PBS containing 0.5% BSA, 0.05% P20, 0.05% PROCLIN® 300, 5 mM EDTA, 0.2% beta-gamma globulin, and 0.35 M NaCl; and (e) PBS containing 0.5% BSA, 0.05% P20, 0.05% PROCLIN® 300, 5 mM EDTA, 0.25% CHAPS, and 0.35 M NaCl.

The conditions for incubation of sample and immobilized capture reagent are selected to maximize sensitivity of the assay and to minimize dissociation, and to ensure that any analyte of interest present in the sample (such as hamster PLBL2) binds to the immobilized capture reagent. Optionally, the sample is separated (for example, by washing) from the immobilized capture reagents to remove uncaptured material. The solution used for washing is generally a buffer (e.g., "washing buffer"). A cross-linking agent or other suitable agent may also be added at this stage to allow the now-bound material of interest (e.g., hamster PLBL2) to be covalently attached to the capture reagents if there is any concern that the captured material of interest may dissociate to some extent in the subsequent steps.

The immobilized capture reagents with any bound material of interest present are contacted with a detection anti-PLBL2 antibody. In some embodiments, the detection antibody is biotinylated. In some embodiments, the detection means for the biotinylated label is avidin or streptavidin-HRP. In some embodiments, the readout of the detection means is fluorimetric or colorimetric.

The level of any free material of interest from the sample (e.g., hamster PLBL2) that is now bound to the capture reagents is measured or quantified using a detection means for the detection antibody. In some embodiments, the measuring or quantifying comprises comparing the reaction that occurs as a result of the above steps with a standard curve to determine the level of material of interest (e.g., hamster PLBL2) compared to a known amount.

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free material of interest (e.g., hamster PLBL2) to the first or second antibodies. Examples of suitable labels include those known for use in immunoassay, such as those enumerated above.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature 144:945 (1962); David et al., Biochemistry, 13:1014-1021 (1974); Pain et al., J. Immunol. Methods 40:219-230 (1981); and Nygren, J. Histochem. and Cytochem., 30:407-412 (1982). In some embodiments, the label is biotin using streptavidin-HRP for detection means.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Following the addition of last labeled antibody, the amount of bound antibody is determined by removing excess unbound labeled antibody through washing and then measuring or quantifying the amount of the attached label using a detection method appropriate to the label, and correlating the measured amount with the amount of the antibody of interest in the biological sample. For example, in the case of enzymes, the amount of color developed and measured will be a direct measurement allowing quantification of the amount of the antibody of interest present. In one embodiment, HRP is the label and the color is detected using the substrate OPD at 490-nm absorbance.

In one example, after an enzyme-labeled second antibody directed against the first unlabeled antibody is washed from the immobilized phase, color or chemiluminiscence is developed and measured by incubating the immobilized capture reagent with a substrate of the enzyme. Then the concentration of the material of interest (e.g., hamster PLBL2) is calculated by comparing with the color or chemiluminescence generated by the standard run in parallel.

Polypeptides

Exemplary Anti-Hamster PLBL2 Antibodies

Polypeptides for use in any of the assay methods described herein are provided. In one aspect, isolated antibodies that bind hamster PLBL2 are provided. In some embodiments, an anti-PLBL2 antibody comprises at least one, two, three, four, five, or six CDRs selected from (a) CDRH1 comprising the amino acid sequence of SEQ ID NO: 15; (b) CDRH2 comprising the amino acid sequence of SEQ ID NO: 16; (c) CDRH3 comprising the amino acid sequence of SEQ ID NO: 17; (d) CDRL1 comprising the amino acid sequence of SEQ ID NO: 20; (e) CDRL2 comprising the amino acid sequence of SEQ ID NO: 21; and (f) CDRL3 comprising the amino acid sequence of SEQ ID NO: 22. In some embodiments, an anti-PLBL2 antibody comprises a variable heavy chain region comprising the amino acid sequence of SEQ ID NO: 14. In some embodiments, an anti-PLBL2 antibody comprises a variable light chain region comprising the amino acid sequence of SEQ ID NO: 19. In some embodiments, an anti-PLBL2 antibody ("19C10") comprises a heavy chain comprising the amino acid sequence of SEQ ID NO: 13 and a light chain comprising the amino acid sequence of SEQ ID NO: 18. In another embodiment, the antibody comprises the CDR sequences that are 95% or more identical to the CDR sequences of SEQ ID NO: 13 and SEQ ID NO: 18.

In another aspect, an anti-PLBL2 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 14. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PLBL2 antibody comprising that sequence retains the ability to bind to PLBL2. In certain embodiments, a total of 1 to 10 amino acids have been substituted, inserted and/or deleted in SEQ ID NO: 14. In certain embodiments, substitutions, insertions, or deletions occur in regions outside the CDRs (i.e., in the FRs). Optionally, the anti-PLBL2 antibody comprises the VH sequence in SEQ ID NO: 14, including post-translational modifications of that sequence.

In another aspect, an anti-PLBL2 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 19. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PLBL2 antibody comprising that sequence retains the ability to bind to PLBL2. In certain embodiments, a total of 1 to 10 amino acids have been substituted, inserted and/or deleted in SEQ ID NO: 19. In certain embodiments, the substitutions, insertions, or deletions occur in regions outside the CDRs (i.e., in the FRs). Optionally, the anti-PLBL2 antibody comprises the VL sequence in SEQ ID NO: 19, including post-translational modifications of that sequence.

In certain embodiments, an anti-PLBL2 antibody comprises at least one, two three, four, five, or six CDRs selected from (a) CDRH1 comprising the amino acid sequence of SEQ ID NO: 5; (b) CDRH2 comprising the amino acid sequence of SEQ ID NO: 6; (c) CDRH3 comprising the amino acid sequence of SEQ ID NO: 7; (d) CDRL1 comprising the amino acid sequence of SEQ ID NO: 10; (e) CDRL2 comprising the amino acid sequence of SEQ ID NO: 11; and (f) CDRL3 comprising the amino acid sequence of SEQ ID NO: 12. In some embodiments, an anti-PLBL2 antibody comprises a variable heavy chain region comprising the amino acid sequence of SEQ ID NO: 4. In some embodiments, an anti-PLBL2 antibody comprises a variable light chain region comprising the amino acid sequence of SEQ ID NO: 9. In some embodiments, an anti-PLBL2 antibody ("15G11") comprises a heavy chain comprising the amino acid sequence of SEQ ID NO: 3 and a light chain comprising the amino acid sequence of SEQ ID NO: 8. In another embodiment, the antibody comprises the CDR sequences that are 95% or more identical to the CDR sequences of SEQ ID NO: 3 and SEQ ID NO: 8.

In another aspect, an anti-PLBL2 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PLBL2 antibody comprising that sequence retains the ability to bind to PLBL2. In certain embodiments, a total of 1 to 10 amino acids have been substituted, inserted and/or deleted in SEQ ID NO: 4. In certain embodiments, substitutions, insertions, or deletions occur in regions outside the CDRs (i.e., in the FRs). Optionally, the anti-PLBL2 antibody comprises the VH sequence in SEQ ID NO: 4, including post-translational modifications of that sequence.

In another aspect, an anti-PLBL2 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 9. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PLBL2 antibody comprising that sequence retains the ability to bind to PLBL2. In certain embodiments, a total of 1 to 10 amino acids have been substituted, inserted and/or deleted in SEQ ID NO: 9. In certain embodiments, the substitutions, insertions, or deletions occur in regions outside the CDRs (i.e., in the FRs). Optionally, the anti-PLBL2 antibody comprises the VL sequence in SEQ ID NO: 9, including post-translational modifications of that sequence.

In another aspect, an anti-PLBL2 antibody is provided, wherein the antibody comprises a VH as in any of the embodiments provided above, and a VL as in any of the embodiments provided above.

In a further aspect, also provided is an antibody that binds to the same epitope as an anti-PLBL2 antibody described herein. For example, in certain embodiments, an antibody is provided that binds to the same epitope as an anti-PLBL2 antibody comprising a VH sequence of SEQ ID NO: 14 and a VL sequence of SEQ ID NO: 19. For example, in certain embodiments, an antibody is provided that binds to the same epitope as an anti-PLBL2 antibody comprising a VH sequence of SEQ ID NO: 4 and a VL sequence of SEQ ID NO: 9.

In a further aspect of the invention, an anti-PLBL2 antibody according to any of the above embodiments is a monoclonal antibody, including a chimeric, humanized or human antibody. In one embodiment, an anti-PLBL2 antibody is an antibody fragment, e.g., a Fv, Fab, Fab', scFv, diabody, or F(ab')2 fragment. In another embodiment, the antibody is a full length antibody, e.g., an intact IgG1 antibody or other antibody class or isotype as defined herein. In another embodiment, the antibody is a multispecific antibody, a bispecific antibody, a half antibody or an antibody fragment. Exemplary recombinant polypeptides Also provided are recombinant polypeptides and preparations thereof, samples of which may be assayed by the methods described herein. Examples of such recombinant polypeptides include but are not limited to immunoglobulins, immunoadhesins, antibodies, enzymes, hormones, fusion proteins, Fc-containing proteins, immunoconjugates, cytokines and interleukins, mammalian proteins, such as, e.g., renin; a hormone; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; dotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; an enzyme; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins (IGFBPs); a cytokine; CD proteins such as CD3, CD4, CD8, CD19 and CD20; erythropoietin; osteoinductive factors; immunotoxins; a fusion polypeptide, i.e. polypeptide comprised on two or more heterologous polypeptides or fragments thereof and encoded by a recombinant nucleic acid; an Fc-containing polypeptide, for example, a fusion protein comprising an immunoglobulin Fc region, or fragment thereof, fused to a second polypeptide; an immunoconjugate; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

In some embodiments, the polypeptide preparation for use in any of the assay methods described herein contains an antibody of interest, i.e. the recombinant polypeptide produced by a host cell is an antibody.

Molecular targets for such antibodies include CD proteins and their ligands, such as, but not limited to: (i) CD3, CD4, CD8, CD19, CD11a, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac1, p150,95, VLA-4, ICAM-1, VCAM and αv/β3 integrin, including either alpha or beta subunits thereof (e.g., anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; and (v) cell surface and transmembrane tumor-associated antigens (TAA), such as those described in U.S. Pat. No. 7,521,541.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

Polyclonal Antibodies

In some embodiments, antibodies are polyclonal antibodies. Polyclonal antibodies are preferably raised in animals by multiple subcutaneous (sc) or intraperitoneal (ip) injections of the relevant antigen and an adjuvant. It may be useful to conjugate the relevant antigen to a polypeptide that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups.

Animals are immunized against the antigen, immunogenic conjugates, or derivatives by combining, e.g., 100 µg or 5 µg of the polypeptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different polypeptide and/or through a different cross-linking reagent. Conjugates also can be made in recombinant cell culture as polypeptide fusions. Also, aggregating agents such as alum are suitably used to enhance the immune response.

Monoclonal Antibodies

In some embodiments, antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al.,

*Monoclonal Antibody Production Techniques and Applications* pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as *E. coli* cells, simian COS cells, human embryonic kidney (HEK) 293 cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352:624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

Antibody Fragments

In some embodiments, an antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a F(ab')$_2$ fragment, a scFv, a Fv, and a diabody.

Polypeptide Variants and Modifications

Amino acid sequence modification(s) of the polypeptides, including antibodies, described herein may be used in the methods of assaying polypeptide preparations (e.g., antibodies) described herein.

Variant Polypeptides

"Polypeptide variant" means a polypeptide, for example, an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide. Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, *Science* 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 1 below under the heading of "preferred substitutions." If such substitutions result in a change in biological activity, then more substantial changes, denominated "exemplary substitutions" in the Table 1, or as further described below in reference to amino acid classes, may be introduced and the products screened.

TABLE 1

| Original Residue | Exemplary Substitutions | Conservative Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, *Biochemistry* second ed., pp. 73-75, Worth Publishers, New York (1975)):
  (1) non-polar: Ala (A), Val (V), Leu (L), Ile (I), Pro (P), Phe (F), Trp (W), Met (M)
  (2) uncharged polar: Gly (G), Ser (S), Thr (T), Cys (C), Tyr (Y), Asn (N), Gln (Q)
  (3) acidic: Asp (D), Glu (E)
  (4) basic: Lys (K), Arg (R), His(H)
Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.
Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

One example of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains, acetylation of the N-terminal amine, and amidation of any C-terminal carboxyl group.

Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

Obtaining Polypeptides for Use in the Assay Methods

The polypeptides used in the assay methods described herein may be obtained using methods well-known in the art, including the recombination methods. The following sections provide guidance regarding these methods.

(A) Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and F(ab')$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

Suitably, the polynucleotides described herein may be isolated and/or purified. In some embodiments, the polynucleotides are isolated polynucleotides.

The term "isolated polynucleotide" is intended to indicate that the molecule is removed or separated from its normal or natural environment or has been produced in such a way that it is not present in its normal or natural environment. In some embodiments, the polynucleotides are purified polynucleotides. The term purified is intended to indicate that at least some contaminating molecules or substances have been removed.

Suitably, the polynucleotides are substantially purified, such that the relevant polynucleotides constitutes the dominant (i.e., most abundant) polynucleotides present in a composition.

(B) Expression of Polynucleotides

The description below relates primarily to production of polypeptides by culturing cells transformed or transfected with a vector containing polypeptide-encoding polynucleotides. It is, of course, contemplated that alternative methods, which are well known in the art, may be employed to prepare polypeptides. For instance, the appropriate amino acid sequence, or portions thereof, may be produced by direct peptide synthesis using solid-phase techniques (see, e.g., Stewart et al., *Solid-Phase Peptide* Synthesis W. H. Freeman Co., San Francisco, Calif. (1969); Merrifield, *J. Am. Chem. Soc.* 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the polypeptide may be chemically synthesized separately and combined using chemical or enzymatic methods to produce the desired polypeptide.

Polynucleotides as described herein are inserted into an expression vector(s) for production of the polypeptides. The term "control sequences" refers to DNA sequences necessary for the expression of an operably linked coding sequence in a particular host organism. The control sequences include, but are not limited to, promoters (e.g., naturally-associated or heterologous promoters), signal sequences, enhancer elements, and transcription termination sequences.

A polynucleotide is "operably linked" when it is placed into a functional relationship with another polynucleotide sequence. For example, nucleic acids for a presequence or secretory leader is operably linked to nucleic acids for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

For antibodies, the light and heavy chains can be cloned in the same or different expression vectors. The nucleic acid segments encoding immunoglobulin chains are operably linked to control sequences in the expression vector(s) that ensure the expression of immunoglobulin polypeptides.

The vectors containing the polynucleotide sequences (e.g., the variable heavy and/or variable light chain encoding sequences and optional expression control sequences) can be transferred into a host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

(C) Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *Escherichia coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

Vectors may be transformed into a suitable host cell as described below to provide for expression of a polypeptide. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

The vectors may be for example, plasmid, virus or phage vectors provided with an origin of replication, optionally a promoter for the expression of the said polynucleotide and optionally a regulator of the promoter. Vectors may contain one or more selectable marker genes which are well known in the art.

These expression vectors are typically replicable in the host organisms either as episomes or as an integral part of the host chromosomal DNA.

(D) Host Cells

The host cell may be a bacterium, a yeast or other fungal cell, insect cell, a plant cell, or a mammalian cell, for example. Typically, host cells do not contain exogenous nucleic acids encoding recombinant polypeptides of interest or products, although host cells may contain exogenous nucleic acids encoding polypeptides, the expression of which confer desirable traits on the cells under certain conditions, for example, nucleic acids that encode polypeptides conferring antibiotic resistance.

A transgenic multicellular host organism which has been genetically manipulated may be used to produce a polypeptide. The organism may be, for example, a transgenic mammalian organism (e.g., a transgenic goat or mouse line).

Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P), *Pseudomonas* such as *P. aeruginosa*, and *Streptomyces*. These examples are illustrative rather than limiting. Strain W3110 is one particularly preferred host or parent host because it is a common host strain for recombinant polynucleotide product fermentations. Preferably, the host cell secretes minimal amounts of proteolytic enzymes. For example, strain W3110 may be modified to effect a genetic mutation in the genes encoding polypeptides endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan; *E. coli* W3110 strain 37D6, which has the complete genotype tonA ptr3 phoA E15 (argF-lac) 169 degP ompT rbs7 ilvG kan; *E. coli* W3110 strain 40B4, which is strain 37D6 with a non-kanamycin resistant degP deletion mutation; and an *E. coli* strain having mutant periplasmic protease. Alternatively, in vitro methods of cloning, e.g., PCR or other nucleic acid polymerase reactions, are suitable.

In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Eukaryotic microbes may be used for expression. Eukaryotic microbes such as filamentous fungi or yeast are suitable cloning or expression hosts for polypeptide-encoding vectors. *Saccharomyces cerevisiae* is a commonly used lower eukaryotic host microorganism. Others include *Schizosaccharomyces pombe; Kluyveromyces* hosts such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris; Candida; Trichoderma reesia; Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans*, and *A. niger*. Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula. Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides as described herein and in some instances are preferred (See Winnacker, *From Genes to Clones* VCH Publishers, N.Y., N.Y. (1987). For some embodiments, eukaryotic cells may be preferred, because a number of suitable host cell lines capable of secreting heterologous polypeptides (e.g., intact immunoglobulins) have been developed in the art, and include CHO cell lines, various Cos cell lines, HeLa cells, preferably, myeloma cell lines, or transformed B-cells or hybridomas. In some embodiments, the mammalian host cell is a CHO cell.

In some embodiments, the host cell is a vertebrate host cell. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR(CHO or CHO-DP-12 line); mouse sertoli cells; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Recombinant Methods

Recombinant polypeptides of interest, also referred to herein as products, such as antibodies, may be produced using recombinant methods and compositions, e.g., as described in U.S. Pat. No. 4,816,567. In some embodiments, isolated nucleic acid encoding a recombinant polypeptide such as an antibody are provided. Such nucleic acids may encode an amino acid sequence comprising the VL and/or an amino acid sequence comprising the VH of the antibody (e.g., the light and/or heavy chains of the antibody). In some embodiments, one or more vectors (e.g., expression vectors) comprising such nucleic acid are provided. In some embodiments, a host cell is transformed or transfected with such nucleic acid to generate a recombinant polypeptide-expressing cell or product cell. In one such embodiment, a recombinant polypeptide-expressing cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody.

In some embodiments, the host cell is eukaryotic, e.g. a Chinese Hamster Ovary (CHO) cell. In some embodiments, a method of making a recombinant polypeptide is provided, wherein the method comprises culturing a recombinant polypeptide-expressing cell comprising nucleic acid encoding the product, as provided above, under conditions suitable for expression of the product, and optionally recovering the product from the cell (or cell culture medium).

Articles of Manufacture

The polypeptides used in the methods described herein may be contained within an article of manufacture. The article of manufacture may comprise a container containing the polypeptide(s). In some embodiments, the article of manufacture comprises: (a) a container comprising a composition comprising the polypeptide(s) described herein within the container; and (b) a package insert with instructions for using the polypeptide(s) in the assay method.

The article of manufacture comprises a container and a label or package insert on or associated with the container. Suitable containers include, for example, bottles, vials, test tubes etc. The containers may be formed from a variety of materials such as glass or plastic. The container holds or contains a polypeptide composition. At least one active agent in the composition is the polypeptide. The label or package insert indicates that the composition's use in an assay with specific guidance regarding amounts and incubation times. The article of manufacture may further include other materials desirable from a commercial and user standpoint, including other buffers, diluents, filters.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

EXAMPLES

The following are examples of methods and compositions of the invention. It is understood that various other embodiments may be practiced, given the general description provided above.

As used in the Examples below and elsewhere herein, "PLB2" and "PLBL2" and "PLBD2" are used interchangeably and refer to the enzyme "phospholipase B-like 2" or its synonym, "phospholipase B-domain-like 2".

Example 1—General Methods

MAb Feedstocks

MAb feedstocks for all examples were selected from industrial, pilot or small scale cell culture batches at Genentech (South San Francisco, Calif., U.S.A.). After a period of cell culture fermentation, the cells were separated and, in certain instances, the clarified fluid (harvested cell culture fluid, HCCF) was purified by Protein A chromatography and one or more additional chromatography steps and filtration steps as indicated in the Examples below. HCCF or in-process pools at various steps of purification were used to investigate the performance of the ELISA assay described in Examples 3 and 5. The results of using the Example 3 ELISA assay are described in Example 4 and the results of using the Example 5 ELISA assay are described in Example 6.

Spectrophotometric Method for MAb Quantification

The concentration of antibody was determined via absorbance at 280 and 320 nm using a UV-visible spectrophotometer (8453 model G1103A; Agilent Technologies; Santa Clara, Calif.) or NanoDrop 1000 model ND-1000 (Thermo Fisher Scientific; Waltham, Mass., U.S.A.). Species other than antibody (i.e. impurities) were too low in concentration to have an appreciable effect on UV absorbance. As needed, samples were diluted with an appropriate non-interfering diluent in the range of 0.1-1.0 absorbance unit. Sample preparation and UV measurements were performed in duplicate and the average value was recorded. The mAb absorption coefficients ranged from 1.42 to 1.645/mg·ml·cm.

Affinity Chromatographic/HPLC Method for Product Quantification (Product Concentration Assay)

The product concentration assay is an affinity chromatographic method for the measurement of polypeptides that bind to Protein A. The method may use HPLC as a means for carrying out the affinity chromatography. Products that may be measured by this assay include any Fc-containing polypeptide and include for example, but are not limited to, monoclonal antibodies, bispecific or multispecific antibodies, antibody fragments, including half antibodies, and immunoadhesins. An affinity chromatography column (2.1-mm diameter×30-mm length, 20-μm particle size) containing immobilized Protein A (approximately 1 mg) and an approximate volume of 0.1 mL was used in the method. Protein A affinity chromatography columns can be made by methods known in the art and are also available commercially, e.g., from Life Technologies. Samples and four standards of differing IgG concentration were applied to the column (20 uL standard injection volume) in a Phosphate Buffered Saline loading buffer. Typically, the samples were Harvested Cell Culture Fluid (HCCF) and the product was eluted from the column with 2% acetic acid/100 mM glycine (pH 2.5) at a flow rate of 2 mL/min. The peak area of the eluted material was compared to the peak areas of the four point IgG standard curve, using the extinction coefficient of the appropriate product, to calculate the amount of product analyte. The range of the assay was typically 0.025 mg/mL-4.0 mg/mL. Product concentration was determined according to the following formula: mg/mL IgG=HPLC value (mg/mL)×(extinction coefficient of standard material/extinction coefficient of sample material).

Total CHO Host Cell Protein (CHOP) Quantification

An ELISA was used to quantify the levels of the total host cell proteins called CHOP. The ELISAs used to detect CHO proteins in products were based upon a sandwich ELISA format. Affinity-purified polyclonal antibody to CHOP was coated onto a 96-well microtiter plate. Standards, controls, and samples were then loaded in duplicate into separate wells. CHOP, if present in the sample, will bind to the coat antibody (polyclonal anti-CHOP). After an incubation step, anti-CHOP polyclonal antibody-conjugated to horseradish peroxidase (HRP) was added to the plate. After a final wash step, CHOP was quantified by adding a solution of tetramethyl benzidine (TMB), also available as SUREBLUE RESERVE™ from KPL, Kirkegaard & Perry Laboratories, Inc., Gaithersburg, Md., cat no. 53-00-03), which when acted on by the HRP enzyme produces a colorimetric signal. The optical density (OD) at 450 nm was measured in each well. A five-parameter curve-fitting program (SOFTMAX® Pro, Molecular Devices, Sunnyvale, Calif.) was used to generate a standard curve, and sample CHOP concentrations were computed from the standard curve. The assay range for the total CHOP ELISA was from 5 to 320 ng/ml. CHOP concentration, in ng/mL, refers to the amount of CHOP in a sample using the CHOP standard as a calibrator. CHOP ratio (in ng/mg or ppm) refers to the calculated ratio of CHOP concentration to product concentration and, in certain instances, was the reported value for the test methods. The Total CHOP ELISA may be used to quantify total CHOP levels in a sample but does not quantify the concentration of individual proteins.

Commercially Available PLBL2 ELISA Assay Kits

Figure 1A:
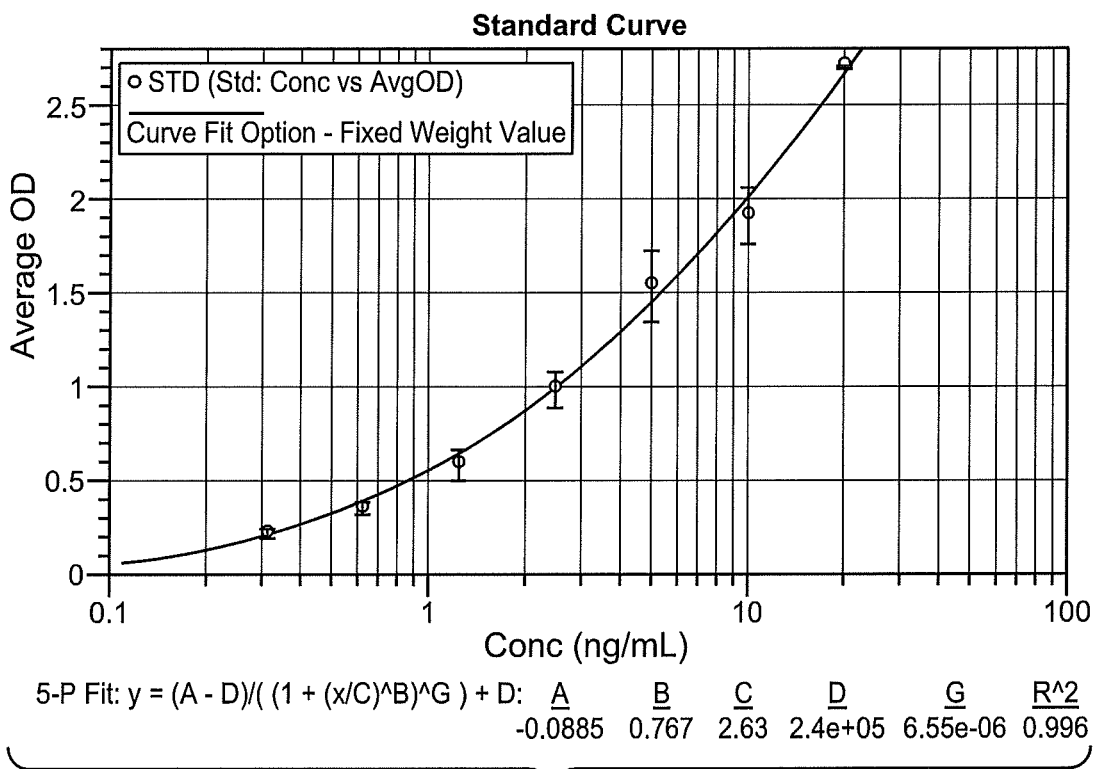
FIGS. 1A and 1B show representative standard curves for commercially available PLBL2 ELISA kits as described in Example 1.

We tested whether either of two commercially available kits marketed for the purpose of detecting PLBL2 would be capable of detecting PLBL2 in recombinant antibody preparations and if so, whether they would provide adequate quantification. The first kit tested was ELISA Assay Kit for human Phospholipase B (PLB) E92048Hu from USCN Life Science Inc. This kit is described as a sandwich ELISA for in vitro quantitative measurement of PLB in human tissue homogenates and other biological fluids. Samples tested in this assay included one known positive source (a recombinant antibody preparation purified from CHO cells) of hamster PLBL2 where the level of PLBL2 impurity had been determined using a mass spectrometry assay (described further below) to be approximately 300 ng/mg. A second recombinant antibody preparation purified from CHO cells and known to have no detectable PLBL2 was also tested. Although a standard curve was generated showing detection of the human PLBL2 standard included in the kit over the range of 0.3-20 ng/ml (FIG. 1A), no reactivity of the test samples was detected. Both antibody preparations were tested at 10 mg/mL (equivalent of about 3,000 ng/mL PLBL2 in the positive sample) and in four 2-fold serial dilutions from 10 mg/mL down to about 1.3 mg/mL (equivalent to 375 ng/mL PLBL2 in the positive sample). Both antibody preparations gave the same result, an OD of about 0.1 AU, e.g. background, at all dilutions. There was no difference between the sample known to contain hamster PLBL2 and the one known not to contain this impurity. There was no difference as a function of sample dilution, indicating no ability to quantify hamster PLBL2 in our sample. We concluded that the antibodies in this kit did not recognize the hamster PLBL2 impurity in our sample.

Figure 1B:
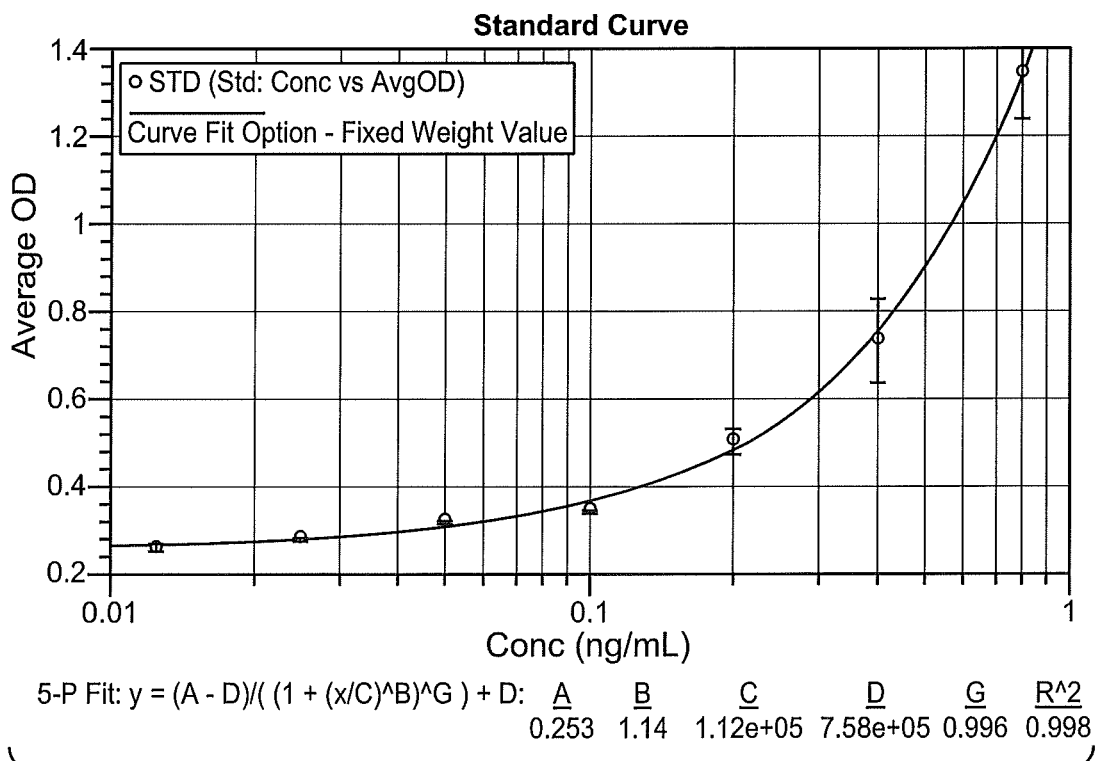

The other kit tested was Hamster putative phospholipase B-like 2 (PLBD2) ELISA kit, catalog CSB-EL018125Ha from CUSABIO. This kit claims to provide quantitative determination of hamster putative phospholipase B-like (PLBD2) concentrations in serum, plasma, tissue homogenates, cell lysates. The same samples as tested in the USCN Life Science Inc. kit were also assayed in this kit. Although a standard curve was generated showing detection of the hamster PLBL2 standard included in the kit over the range of 0.12-8 ng/ml (FIG. 1B), no reactivity of the test samples was detected. As described above, both antibody preparations were tested at 10 mg/mL (equivalent of about 3,000 ng/mL PLBL2 in the positive sample) and in five 2-fold serial dilutions from 10 mg/mL down to about 625 µg/mL (equivalent to 188 ng/mL PLBL2 in the positive sample). Both antibody preparations gave the same result, an OD of about 0.4 AU, e.g. background, at all dilutions. There was no difference between the sample known to contain hamster PLBL2 and the one known not to contain this impurity. There was no difference as a function of sample dilution, indicating no ability to quantify hamster PLBL2 in our sample. We concluded that the antibodies in this kit did not recognize the hamster PLBL2 impurity in our sample.

We therefore concluded that these commercially available assays did not quantify hamster PLBL2 in samples that were known to be positive for hamster PLBL2. One explanation is that the anti-PLBL2 antibodies in these assays are of low affinity for the hamster (CHO)-PLBL2 found in our samples. Another explanation is that the anti-PLBL2 antibodies were unable to detect CHO-PLBL2 when it appeared in the sample matrix that contained high levels of recombinant human IgG, as in our samples. These results indicated a need to develop new anti-PLBL2 antibodies and new assay conditions to enable the detection and accurate quantification of PLBL2 impurity in our recombinant antibody preparations. Those efforts are described in the Examples below.

Example 2—Generation of Antibodies that Bind Hamster PLBL2

Identification of PLBL2 as an impurity in an antibody preparation prompted us to synthesize the gene, and then express and purify hamster PLBL2. The literature on PLBL2 describes it as a lysosomal enzyme of approximately 66 kD molecular weight (F. Deuschl et al., FEBS Lett 580:5747-5752 (2006)). As with other lysosomal enzymes this protein contains multiple post translational modifications with mannose-6-phosphate, and is originally synthesized as a pre-proenzyme. During processing, a leader sequence is clipped off, and a proteolytic clip occurs, resulting in the protein running as three bands on SDS-PAGE gels: intact PLBL2 (MW 66 kD), an N-terminal domain (28 kD) and a C-terminal domain (40 kD). Clipping occurs at acidic pH levels. Although the N-domain and C-domains separate on SDS-PAGE, the fragments probably do not separate in native conditions, since we have observed that strong solvents (e.g., urea, guanidine, or ethanol) were needed to separate the fragments. Additionally, other laboratories that have purified PLBL2 for crystallography studies have also observed this clip and have been unable to separate intact from clipped proteins with chromatographic methods (F. Deuschl et al., FEBS Lett 580:5747-5752 (2006); A. Jensen et al., *Biochem Journal* 402, 449-458 (2007), F. Lakomek et al., *BMC Structural Biology* 9:56 (2009)).

DNA encoding soluble hamster (*Cricetulus griseus*) PLBL2 was synthesized from publicly available sequence information (see Table of Sequences below for exemplary nucleic acid and amino acid sequences) and cloned into a standard mammalian expression vector using typical methods known in the art including the addition of a histidine (his) tag. Soluble PLBL2 was transiently expressed in CHO-K1 cells (ATCC® CRL9618™). Cell culture supernatants were harvested (referred to as HCCF) and PLBL2 was purified using the following methods.

Harvested Cell Culture Fluid (HCCF) was ultrafiltered (UF) 10-fold by Tangential Flow Filtration (TFF), using 10 kDa molecular weight cutoff (MWCO) membranes. The UF HCCF was diafiltered (DF) against 10 volumes of a phosphate-buffered saline (PBS), NaCl buffer. The UF/DF HCCF was applied to a Ni-NTA immobilized metal affinity chromatography (IMAC) column (QIAGEN, Cat. No. 30622) and eluted with an increasing imidazole gradient. The Ni-NTA pool was conditioned with a buffer containing sodium sulfate, and then applied to an Octyl-Sepharose CL-4B hydrophobic interaction chromatography (HIC) column (GE Healthcare Life Sciences, Product No. 17-0790-01). The Octyl-Sepharose column was eluted with a decreasing sodium sulfate gradient. The Octyl-Sepharose pool was re-chromatographed on a Ni-NTA column and step-eluted with a high concentration of imidazole. The Ni-NTA re-chromatography pool was concentrated using centrifugal filtration units equipped with 10 kDa molecular weight cutoff membranes (Millipore). The concentrated Ni-NTA re-chromatography pool was formulated on a Superdex 200 size-exclusion chromatography (SEC) column (GE Healthcare Life Sciences, Product No. 17-1043-02). Fractions from the Superdex 200 column were collected and analyzed by sodium dodecyl sulfate polyacrylamide gel electrophoresis (SDS-PAGE), high pressure liquid chromatography (HPLC) and by Western Blot methods (using antibodies against total Chinese Hamster Ovary Proteins, CHOP (Genentech, Inc.), and commercially available antibodies against Phospholipase B2) to determine purity.

To generate monoclonal antibodies, five Balb/c mice (Charles River Laboratories International, Inc., Hollister, Calif.) were immunized with the purified recombinant soluble PLBL2 at 3-4 day intervals, in each footpad and intraperitoneally, in an adjuvant containing metabolizable squalene (4% v/v), Tween 80 (0.2% v/v), trehalose 6,6-dimycolate (0.05% w/v) and monophosphoryl lipid A (0.05% w/v; all components obtained from Sigma Aldrich, USA). After 6 injections, serum titers were evaluated by standard enzyme-linked immunosorbant assay (ELISA) to identify mice with positive serum titers to PLBL2. B cells from spleens and lymph nodes from two mice, demonstrating the highest titers, were fused with mouse myeloma cells by electrofusion (Hybrimune; Harvard Apparatus, Inc., Holliston, Mass.). After 7 days, approximately 5000 colonies were picked into 96 well tissue culture plates containing hybridoma culture medium by using Clonepix-FL (Molecular Devices, Sunnyvale, Calif.). The hybridoma supernatants were harvested and screened for PLBL2 specific antibody production by direct ELISA. 25 clones showing specific binding to PLBL2 protein by ELISA were further ranked based on their affinity as measured by OCTET® (ForteBio, Inc., Menlo Park, Calif.). Mouse hybridoma supernatants were diluted to 5 µg/ml in kinetics buffer (ForteBio, Inc., Menlo Park, Calif.) or used neat (if concentration was less than 5 mg/ml) and captured on anti-mouse IgG (Fv) sensor tips (ForteBio, Inc., Menlo Park, Calif.), followed by dipping the sensors in PLBL2 protein at 10 µg/ml. The association and dissociation kinetic measurements were determined by using ForteBio data analysis software. All 25 clones were further characterized by Western blot for binding to C terminal, N terminal and whole PLBL2. Hybridoma supernatants for clones 1.26G6, 1.20B5, 1.19C10, 1.15G11, 1.4E2, 1.39C10 and 1.30F3 showing immunobinding to either C or N terminal or intact PLBL2 protein were purified by affinity chromatography (MabSelect SuRe; GE Healthcare Bio-Sciences, Piscataway, N.J.), sterile-filtered, and stored at 4° C. in PBS. Four of the 7 antibodies with high yield were selected for biotinylation. Binding activity for both biotinylated and unbiotinylated antibodies were confirmed by Octet. The purified antibodies were then evaluated for possible use in development of an ELISA assay. Two antibodies, 1.19C10 and 1.15G11 were selected for ELISA assay development.

The antibodies 1.19C10 and 1.15G11 were both identified as IgG1, kappa using Isostrip Mouse mAb Isotyping Kit (Roche Applied Biosciences, Indianapolis, Ind.). DNA encoding each of these antibodies were cloned and expressed transiently in either 293 cells or CHO cells. To obtain antibody variable sequences from clone 1.15G11 and 1.19C10 for transient expression in CHO cells, a 5' rapid amplification of cDNA ends (5'RACE) method was used, which was based on those methods previously described (see, e.g., Nature Methods 2, 629-630 (2005) and "Rapid amplification of 5' cDNA ends," in Molecular Cloning: A Laboratory Manual (eds. Sambrook, J. & Russell, D. W.) Chapter 8 Protocol 9, 8.54-8.60 (Cold Spring Harbor Laboratory Press, Cold Spring Harbor, N.Y., USA, 2001)). Total RNA was extracted from cultured hybridoma cells (at least $10^6$ cells) with RNeasy Plus kit (Qiagen, Valencia, Calif.) and cDNA was prepared with SMARTer RACE cDNA amplification kit (Clontech Inc., Mountain View, Calif.). To amplify the variable regions of heavy and light chain, universal primer A mix targeting to the oligos tagging at the 5' end of cDNA (included in SMARTer RACE cDNA amplification kit) and a reverse primer targeting to the constant region of mouse IgG heavy chain and kappa light chain were used respectively in Polymerase Chain Reaction (PCR). The PCR condition was setup as following: 1 µL cDNA, 5 µL 10× universal primer mix, 1 µL 10 uM reverse primers, 45 µL PCR premix (Life Technologies Inc. Foster City, Calif.); 94° C., 2 min followed by 94° C. 30 sec, 55° C. 30 sec, 72° C. 30 sec for 30 cycles and 72° C. 10 min. The PCR products were resolved on DNA agarose gel and PCR products with expected size (700 bp for heavy chain and 500 bp for light chain) were purified from gel for sequencing analysis to determine the DNA sequences of variable region of heavy and light chain (VH and VK).

To clone the VH/VK regions described above into antibody expression vectors, we used the In-Fusion® cloning method (Clontech Inc.) and the following primers: 1.15G11 heavy chain, forward primer 5'-ACT GGA GCG TAC GCT GAA GTG AAG CTT GAG GAG TCT-3'(SEQ ID NO:23), reverse primer 5'-AAG ACC GAT GGG CCC TTG GTG GAG GCT GAG GAG ACG GTG ACT GAG GTT C-3' (SEQ ID NO:24); 1.19C10 heavy chain, forward primer 5'-ACT GGA GCG TAC GCT GAG GTG CAG CTT CAG GAG TCA-3' (SEQ ID NO:25), reverse primer 5'-AAG ACC GAT GGG CCC TTG GTG GAG GCT GAG GAG ACT GTG AGA GTG GTG C-3'(SEQ ID NO:26). For both 1.15G11 and 1.19C10 light chain, forward primer 5'-GCA ACT GCA ACC GGT GTA CAT TCA GAC ATT GTG ATG ACC CAG TCT-3' (SEQ ID NO:27), reverse primer 5'-GGT GCA GCC ACG GTC CGC TTC AGC TCC AGC TTG GTA CC-3' (SEQ ID NO:28). 1 µL of cDNA was used as template in PCR under the same condition described previously. PCR products were then purified with PCR clean-up kit (Qiagen Inc.) for subcloning into antibody expression vectors. Mouse IgG1 expression vector was linearized with BsiWI and ApaI digestion, and mouse kappa expression vector was digested with AgeI and BssHII. For In-Fusion® cloning reaction, 50 ng linearized vector DNA and 50 ng VH or VK PCR products were mix together with 5× In-Fusion® enzymes and then incubated at 50° C. for 15 min. 3 µL of In-Fusion® reaction was used for transformation and plating on carbenicillin (50 µg/mL) selective LB agar plates. Single colonies were picked and cultured for plasmid DNA purification. Clones with in-frame VH or VK insert were identified with sequencing analysis.

The recombinant antibodies were purified as described above and compared to the purified hybridoma-derived antibodies and found to comparable by both direct ELISA and OCTET® (ForteBio, Inc., Menlo Park, Calif.) (assayed as described above). The recombinant antibodies produced as described above are referred to, respectively, as 19C10 and 5G11. Amino acid sequence information for 19C10 and 5G11 are provided in the Table of Sequences.

To generate polyclonal antibodies, three serum pathogen-free New Zealand white female rabbits (Antibody Solutions, Mountain View, Calif.) were immunized with purified recombinant PLBL2 (as described above) at two-week intervals, subcutaneously in the nape, in an adjuvant containing hydrogel and muramyl dipeptide (MDP). Each injection contained 150 ug of purified recombinant soluble PLBL2. A total of six injections were administered on days 0, 21, 49, 63, 84, and 112. Each rabbit was bled a total of 7 times on days 42, 70, 77, 91, 98, 119 and 126 to test antibody titers. The rabbits were exsanguinated on day 134. As a control, pre-immune serum from each rabbit was collected on day 0 prior to injection.

To determine antibody reactivity to PLBL2, antiserum was used in a solution phase capture method. In the solution phase capture method the pre-immune and anti-sera from the three different rabbits (Rabbit A, B and C) were serially diluted from 1/1000 initial dilution. The diluted sera were incubated with a fixed concentration of biotinylated PLBL2 at 3 ug/mL for 2 hr in a non-binding 96-well plate. The solution was then transferred to Pierce NeutrAvidin Coated Clear 96-Well Plate with Superblock Blocking buffer (Pierce Prod #15129) and incubated for 1 hour to capture the biotinylated PLBL2. After the incubation step, unbound materials were washed away using Wash Buffer (0.05% Polysorbate 20/PBS [Corning Cellgro Cat. No. 99-717-CM]). Peroxidase conjugated AffiniPure goat anti-rabbit IgG (Jackson Immunoresearch Cat. No. 111-035-144) was diluted in Assay Diluent at a dilution factor of 1/20,000 and added to the wells of the microtiter plate. After a 2 hr. incubation step with peroxidase conjugated goat anti-rabbit IgG at room temperature, a final wash step with Wash Buffer (described above) was performed. Subsequently, color was developed by adding a solution of TMB (50 ul/well) (SUREBLUE RESERVE™ from KPL, Kirkegaard & Perry Laboratories, Inc., Gaithersburg, Md., cat no. 53-00-03) followed by incubation at room temperature for 10-20 minutes. Detection was carried out by assessing optical density (OD) at 450 nm in each well using a Molecular Devices Spectra-Max M5e. A five-parameter curve-fitting program (SoftMax Pro v5.2 rev C) was used to process the data.

Based on the solution phase capture experiment described above, the anti-sera from all three rabbits were found to have developed good quality antibodies against PLBL2. The pre-immune serum for all three rabbits did not have affinity for PLBL2. Since all three rabbits had a similar response curve to PLBL2, antisera from exsanguination bleeds from all three rabbits were combined into a single lot for the polyclonal PLBL2 ELISA assay (described below in Example 5).

The pooled rabbit antiserum was initially fractionated with 60% ammonium sulfate, which precipitated all of the antibodies in the serum. Affinity chromatography was used to select for the antibodies produced against PLBL2. PLBL2 was immobilized on Glyceryl-CPG, and the gel was packed into a chromatography column. The 60% ammonium sulfate pellet was dissolved in PBS, pH 7.2, and was loaded to the PLBL2-CPG column. After the loading was complete, the column was washed with PBS+0.02% $NaN_3$, pH 7.2. The antibodies against PLBL2 were eluted from the affinity column with PBS, pH 2.0, collecting the elution pool into a 1.0 M Tris, pH 7.5-8.0 solution. Lastly, the purified anti-PLBL2 antibodies were concentrated and then buffer-exchanged into PBS+0.02% $NaN_3$, pH 7.2, using size-exclusion chromatography. The affinity purified rabbit polyclonal antibodies were used in the polyclonal PLBL2 ELISA described below in Example 5.

Example 3—Murine Monoclonal Anti-Hamster PLBL2 ELISA Assay

An ELISA assay to detect and quantify the CHOP impurity, PLBL2, in recombinant polypeptide samples, such as recombinant antibody or immunoadhesin preparations, was developed. The procedure is as follows. Murine monoclonal antibody 19C10 was coated onto a half area 96-well microtiter plate at a concentration of 0.5 µg/mL in carbonate buffer (0.05M sodium carbonate, pH 9.6), overnight at 2-8° C. After coating, the plate was blocked with Blocking Buffer (0.15M NaCl, 0.1M sodium phosphate, 0.1% fish gelatin, 0.05% polysorbate 20, 0.05% Proclin® 300 [Sigma-Aldrich]; also referred to as Assay Diluent) to prevent non-specific sticking of proteins. Standards, controls, and samples were diluted in Assay Diluent (0.15M NaCl, 0.1M sodium phosphate, 0.1% fish gelatin, 0.05% polysorbate 20, 0.05% Proclin® 300 [Sigma-Aldrich]) then loaded in duplicate into separate wells and incubated for 2 hrs at room temperature (22-27° C.). PLBL2, if present in the sample, would bind to the coat (also referred to herein as capture) antibody. After the incubation step described above, unbound materials were washed away using Wash Buffer (0.05% polysorbate 20/PBS [Corning cellgro Cat. No. 99-717-CM]) and the 15G11 anti-PLBL2 murine monoclonal antibody conjugated to biotin was diluted in Assay Diluent to a concentration of 0.03125 µg/mL and added to the wells of the microtiter plate.

Biotin conjugation was carried out as follows. A biotinylation kit was purchased from Pierce Thermo Scientific, (P/N 20217, E-Z Link NHS-Biotin), and streptavidin-HRP (SA-HRP) from Jackson Immuno Cat. No. 016-030-084. Instructions in the Pierce Kit were followed. Briefly, IgG was dialyzed into PBS, pH 7.4, and biotin was added to the protein and mixed at room temperature for 1 hr. The labeled antibody was then dialyzed against PBS, pH 7.4 to remove excess biotin, filtered, and protein concentration determined by A280.

After a 2 hr. incubation step with biotinylated 15G11 at room temperature, Streptavidin HRP (1:200,000 dilution in Assay Diluent) was added to the microtiter plate wells. After a final wash step with Wash Buffer (described above), color was developed (for PLBL2 quantification) by adding a solution of TMB (50 µl/well) (SUREBLUE RESERVE™ from KPL, Kirkegaard & Perry Laboratories, Inc., Gaithersburg, Md., cat no. 53-00-03) followed by incubation at room temperature for 10-20 minutes. Detection was carried out by assessing optical density (OD) at 450 nm in each well using a Molecular Devices SpectraMax M5e. A four-parameter curve-fitting program (SoftMax Pro v5.2 rev C) was used to generate a standard curve, and sample PLBL2 concentrations were computed from the linear range of the standard curve.

Figure 2:
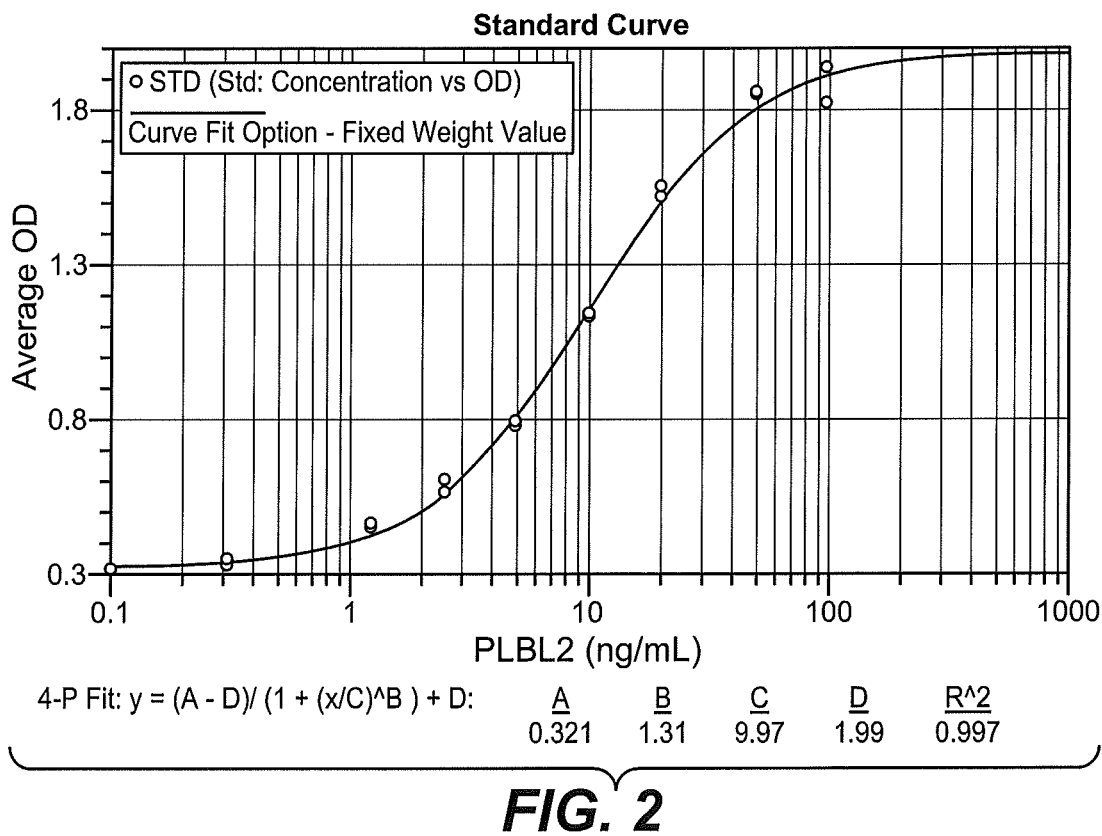
FIG. 2 shows a representative standard curve for the mouse monoclonal PLBL2 ELISA assay as described in Example 3.

As shown in FIG. 2, the PLBL2 assay using the 19C10 and 15G11 monoclonal antibodies had a sigmoidal curve using a 4-pt parameter fit. Values in the linear range of the standard curve were used to calculate nominal PLBL2 (ng/mg or ppm). The linear range was approximately $E_{10}$-$EC_{85}$ or 1.5-40 ng/mL as the range varied slightly from plate to plate. Values obtained for PLBL2 using this ELISA were comparable to estimates made by other methods (e.g., LC-MS/MS, polyclonal PLBL2 ELISA or total CHOP ELISA when diluted to the LOQ of the assay [see Tables 3 an 4]).

Example 4—Results Using Monoclonal PLBL2 ELISA Assay

Using the hamster PLBL2 ELISA assay described above in Example 3, we assessed a variety of monoclonal antibody (mAb) preparations produced in CHO cells to quantify the amount of contaminating PLBL2 under different conditions. We assessed multiple runs of purified preparations as well as harvested cell culture fluid (HCCF), which was not purified. For comparison, in certain cases, we also quantified the amount of PLBL2 peptides by LC-MS/MS. The LC-MS/MS method was performed as follows.

For quantification of PLBL2 by LC-MS/MS, a Waters Acquity H-Class Bio UPLC and AB Sciex TripleTOF 5600+ mass spectrometer were used. Samples and calibration standards (recombinant PLBL2 spiked into a recombinant humanized monoclonal antibody preparation obtained from a mouse NS0 cell line [the NS0 cell line does not contain hamster PLBL2]) were reduced and digested by trypsin. A total of 40 μg digested sample was injected onto the UPLC, using a Waters BEH300 C18 column, particle size 1.7 μm. A linear gradient of acetonitrile was used to elute the peptides, at a flow rate of 300 μl/min and a column temperature of 60° C.

Peptides eluting from the UPLC were introduced to the mass spectrometer by electrospray ionization in positive ionization mode. Ion source temperature was set at 400° C., with an IonSpray voltage of 5500 v. and declustering potential of 76 v. A collision energy setting of 32 was used for the fragmentation of selected peptide ions. The mass spectrometer was operated in multiple reaction monitoring high resolution (MRM$^{HR}$) mode, using four specific PLBL2 peptides and their fragment ion transitions. The parent ions were selected by the quadrupole mass spectrometer with a mass to charge (m/z) selection window of 1.2 amu. Fragment ions of each parent ion were separated by the time-of-flight mass spectrometer and selected for quantification post data acquisition with a selection window of 0.025 amu.

Figure 3:
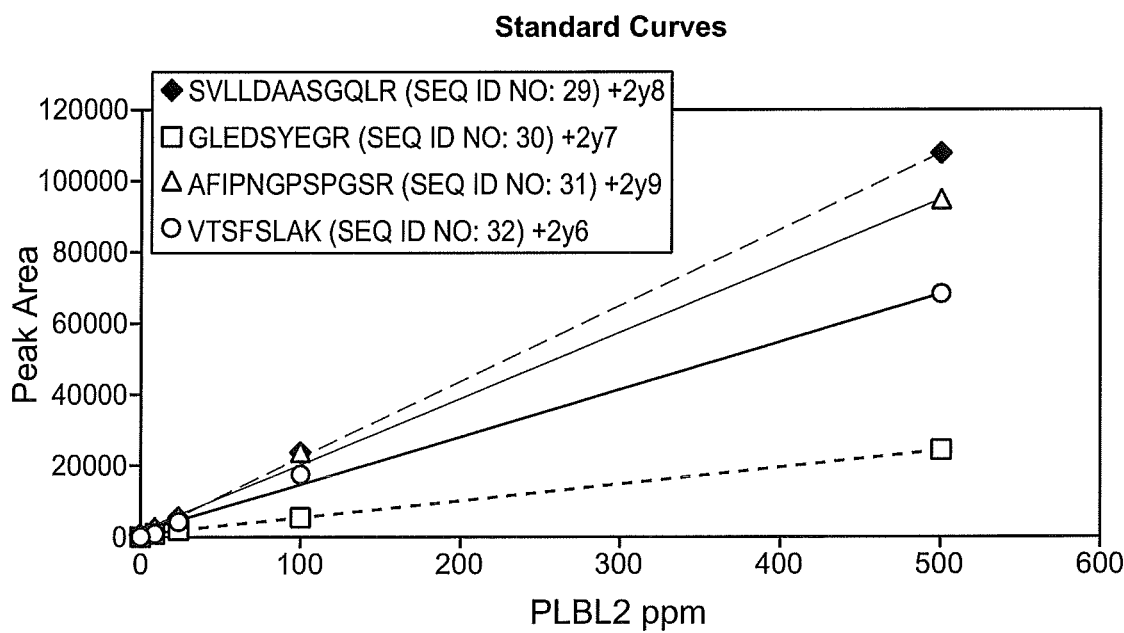
FIG. 3 shows representative standard curves for each of the PLBL2 peptides monitored by LC-MS/MS as described in Example 4. The linearity (R) of each of the standard curves is >0.99.

The concentration of PLBL2 in samples was determined by measuring the specific signal responses of the four transitions, calibrated by those from the standards in the range of 2-500 ppm using a linear fit. Table 2 below shows the list of PLBL2 peptides monitored by LC-MS/MS. Representative standard curves for each of the peptides monitored by LC-MS/MS are shown in FIG. 3.

TABLE 3

PLBL2 Ratio in Various Lots of mAb A

| RUN NUMBER | PLBL2 by ELISA (ng/mg) | PLBL2 by LC-MS/MS (ng/mg) |
|---|---|---|
| 1 | 83 | 87 |
| 2 | 122 | 90 |
| 3 | 34 | 32 |
| 4 | 137 | 103 |
| 5 | 242 | 141 |
| 6 | 328 | 241 |
| 7 | 273 | 154 |
| 8 | 0.2 | <2 |
| 9 | 0.4 | <2 |
| 10 | 0.3 | <2 |
| 11 | 0.2 | <2 |

TABLE 4

PLBL2 Ratio in Various Lots of mAb B

| RUN NUMBER | PLBL2 by ELISA (ng/mg) | PLBL2 by LC-MS/MS (ng/mg) |
|---|---|---|
| 1 | 26 | N/A |
| 2 | 32 | N/A |
| 3 | 41 | 46 |
| 4 | 56 | 61 |
| 5 | 39 | N/A |

Figure 4:
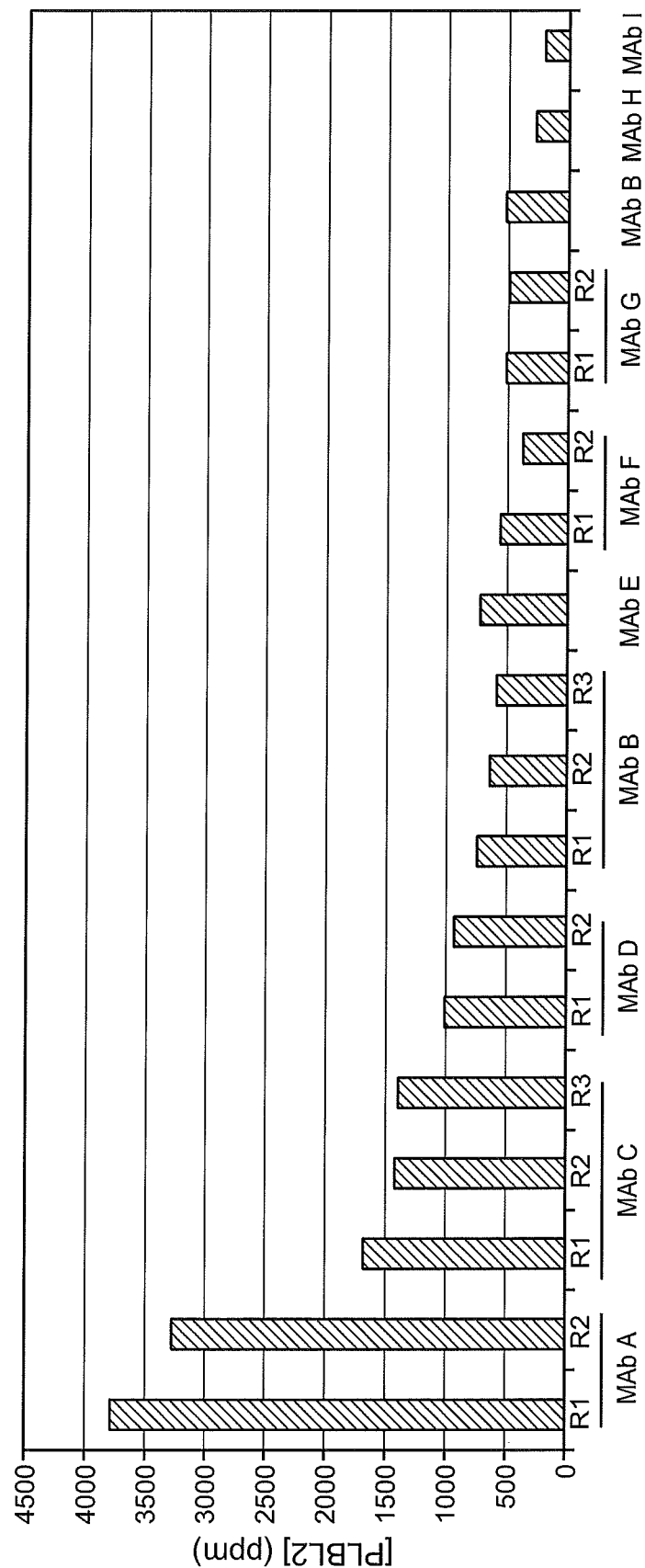
FIG. 4 shows PLBL2 ratio (in ppm) in different mAb HCCF samples as described in Example 4. Replicate runs from the same mAb runs are indicated by R1, R2, R3.

We also assessed the ability of the PLBL2 ELISA assay described in Example 3 to determine levels of contaminating PLBL2 in unpurified HCCF for a wide number of mAb preparations, some of which were IgG1 and some of which were IgG4. Those results are shown in FIG. 4. As can be seen from FIG. 4, the PLBL2 ELISA assay was able to quantify a wide range of PLBL2 in HCCF. While the levels of PLBL2 varied substantially between different mAb

TABLE 2

List of PLBL2 Peptides Monitored by LC-MS/MS TripleTOF 5600+ Scan Cycle

| Scan # | Scan Type | Peptide | SEQ ID NO: | Fragment Ion of Interest | Parent m/z | Fragment m/z |
|---|---|---|---|---|---|---|
| 1 | TOF MS | N/A | | N/A | N/A | N/A |
| 2 | Product Ion | SVLLDAASGQLR | 29 | +2y8 | 615.3461 | 817.4163 |
| 3 | Product Ion | GLEDSYEGR | 30 | +2y7 | 513.2304 | 855.3479 |
| 4 | Product Ion | AFIPNGPSPGSR | 31 | +2y9 | 600.3120 | 868.4272 |
| 5 | Product Ion | VTSFSLAK | 32 | +2y6 | 426.7449 | 652.3665 |

Tables 3 and 4 below show the PLBL2 ratio in various purification runs of two different mAb preparations, mAb A and mAb B, as determined by both LC-MS/MS and by the hamster PLBL2 ELISA assay described in Example 3. Just as for CHOP ratio described above, PLBL2 ratio is provided as ng/mg or parts-per-million (ppm) and refers to the calculated ratio of PLBL2 concentration to product (mAb) concentration. The results shown in Tables 3 and 4 indicate that the PLBL2 ELISA assay was able to quantitate PLBL2 levels in two different mAb preparations over a wide range and under different purification processes (each run number indicates a different purification process).

HCCF samples, reproducibility within replicate HCCF preparations (runs) for any given mAb was good. We did not observe any clear correlation between isotype (IgG1 or IgG4) and level of PLBL2 in HCCF (data not shown).

Figure 5:
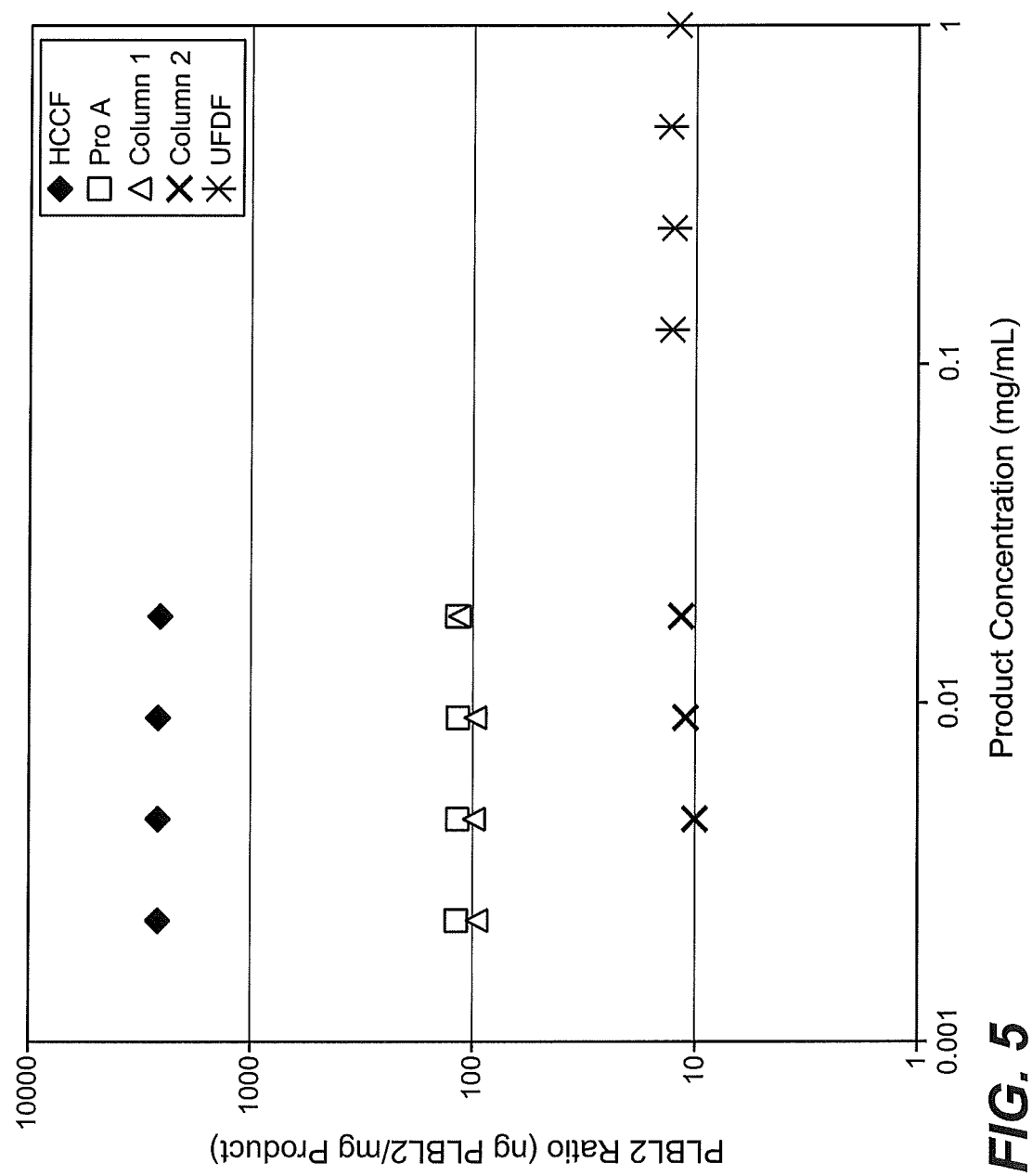
FIG. 5 shows PLBL2 clearance as measured in in-process pool samples of mAb G as described in Example 4.

In addition, we assessed PLBL2 clearance through a three-column chromatography purification process with a final ultrafiltration/diafiltration (UFDF) step of mAb G using the monoclonal PLBL2 ELISA assay described in Example 3. The results are shown in FIG. 5. PLBL2 levels were highest in the HCCF and the purification process was effective for removing PLBL2 from the final mAb G preparation. The monoclonal PLBL2 ELISA assay demonstrated good sensitivity and specificity and was effective for quantifying PLBL2 levels in unpurified HCCF and at each stage of purification. We observed linearity at various product dilutions which indicates that the monoclonal PLBL2 ELISA assay is not subject to the "antigen excess" problem we observed with the total CHOP assay.

Example 5—Rabbit Polyclonal Anti-Hamster PLBL2 ELISA Assay

An ELISA assay to detect and quantify the CHOP impurity, PLBL2, in recombinant polypeptide samples, such as recombinant antibody or immunoadhesin preparations, was developed. The procedure was as follows. Affinity purified rabbit polyclonal antibody was coated onto a half area 96-well microtiter plate at a concentration of 0.5 ug/mL in carbonate buffer (0.05M sodium carbonate, pH 9.6), overnight at 2-8° C. After coating, the plate was blocked with Blocking Buffer (0.15M NaCl, 0.1M sodium phosphate, 0.1% fish gelatin, 0.05% Polysorbate 20, 0.05% Proclin® 300 [Sigma-Aldrich]) to prevent non-specific sticking of proteins. Standards, controls, and samples were diluted in Assay Diluent (0.15M NaCl, 0.1M sodium phosphate, 0.1% fish gelatin, 0.05% Polysorbate 20, 0.05% Proclin® 300 [Sigma-Aldrich]) then loaded in duplicate into separate wells and incubated for 2 hr at room temperature (22-27° C.). PLBL2, if present in the sample, would bind to the coat (also referred to herein as capture) antibody. After the incubation step described above, unbound materials were washed away using Wash Buffer (0.05% Polysorbate 20/PBS [Corning Cellgro Cat. No. 99-717-CM]) and the affinity purified rabbit polyclonal antibody conjugated to horseradish peroxidase (HRP) was diluted in Assay Diluent to a concentration of 40 ng/mL and added to the wells of the microtiter plate.

HRP conjugation was carried out as follows. A HRP conjugation kit was purchased from Pierce Thermo Scientific, (P/N 31489, E-Z Link Plus Activated Peroxidase and Kit). Instructions in the Pierce Kit were followed. Briefly, IgG was dialyzed into Carbonate-Bicarbonate buffer, pH 9.4, and EZ-Link Plus Activated Peroxidase was added to the protein and mixed at room temperature for 1 hr. Sodium cyanoborohydride and Quenching buffer were added subsequently to stabilize the conjugation and quench the reaction. The labeled antibody was then dialyzed against PBS, pH 7.4, filtered, and protein concentration determined by A280.

After a 2 hr. incubation step with HRP conjugated rabbit polyclonal antibody at room temperature, a final wash step with Wash Buffer (described above) was performed. Afterwards, color was developed (for PLBL2 quantification) by adding a solution of TMB (50 ul/well) (SUREBLUE RESERVE™ from KPL, Kirkegaard & Perry Laboratories, Inc., Gaithersburg, Md., cat no. 53-00-03) followed by incubation at room temperature for 10-20 minutes. Detection was carried out by assessing optical density (OD) at 450 nm in each well using a Molecular Devices SpectraMax M5e. A five-parameter curve-fitting program (SoftMax Pro v5.2 rev C) was used to generate a standard curve, and sample PLBL2 concentrations were computed from the linear range of the standard curve.

Figure 6:
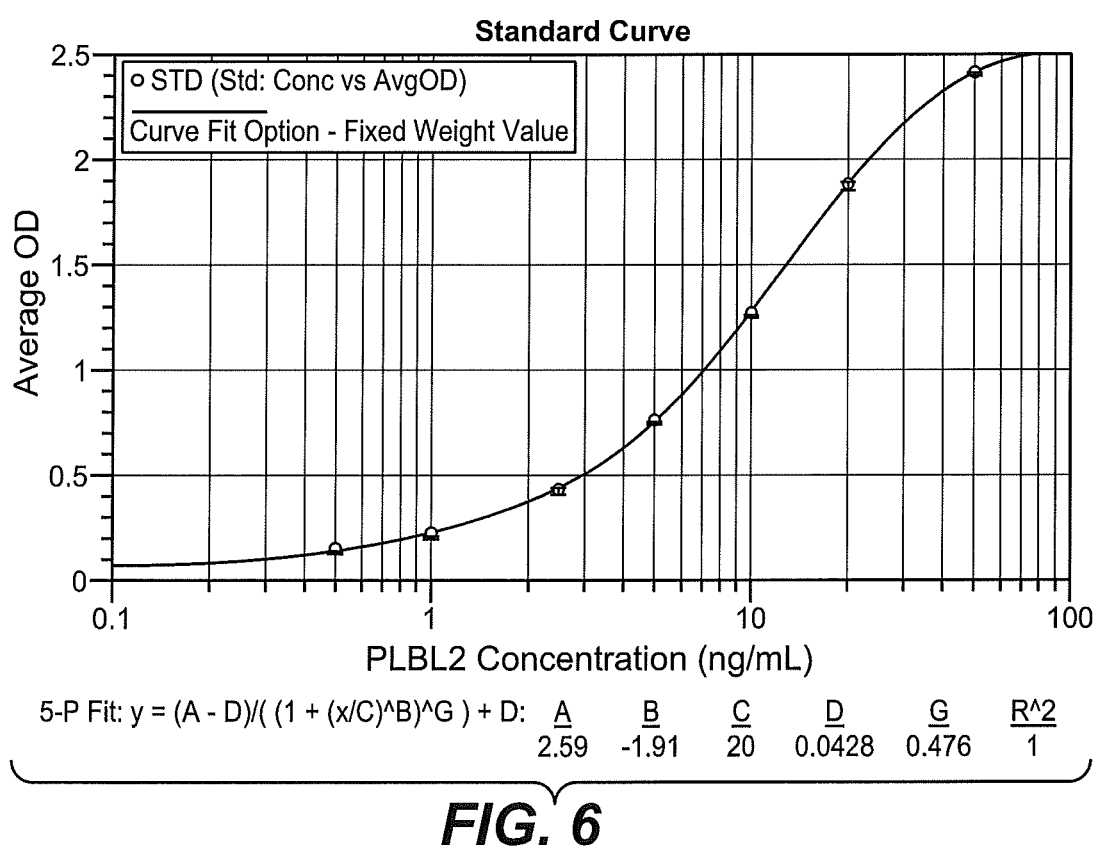
FIG. 6 shows a representative standard curve for the rabbit polyclonal PLBL2 ELISA assay as described in Example 5.

As shown in FIG. 6, the PLBL2 assay using the affinity purified rabbit polyclonal antibodies had a sigmoidal curve using a 5-pt parameter fit. Values in the linear range of the standard curve were used to calculate nominal PLBL2 (ng/mg or ppm). The quantitative range of the assay was 0.5-50 ng/mL. Values obtained for PLBL2 using this ELISA were comparable to estimates made by other methods (e.g., murine monoclonal PLBL2 ELISA, LC-MS/MS or total CHOP ELISA when diluted to the LOQ of the assay).

Example 6—Results Using Polyclonal PLBL2 ELISA Assay

Figure 7:
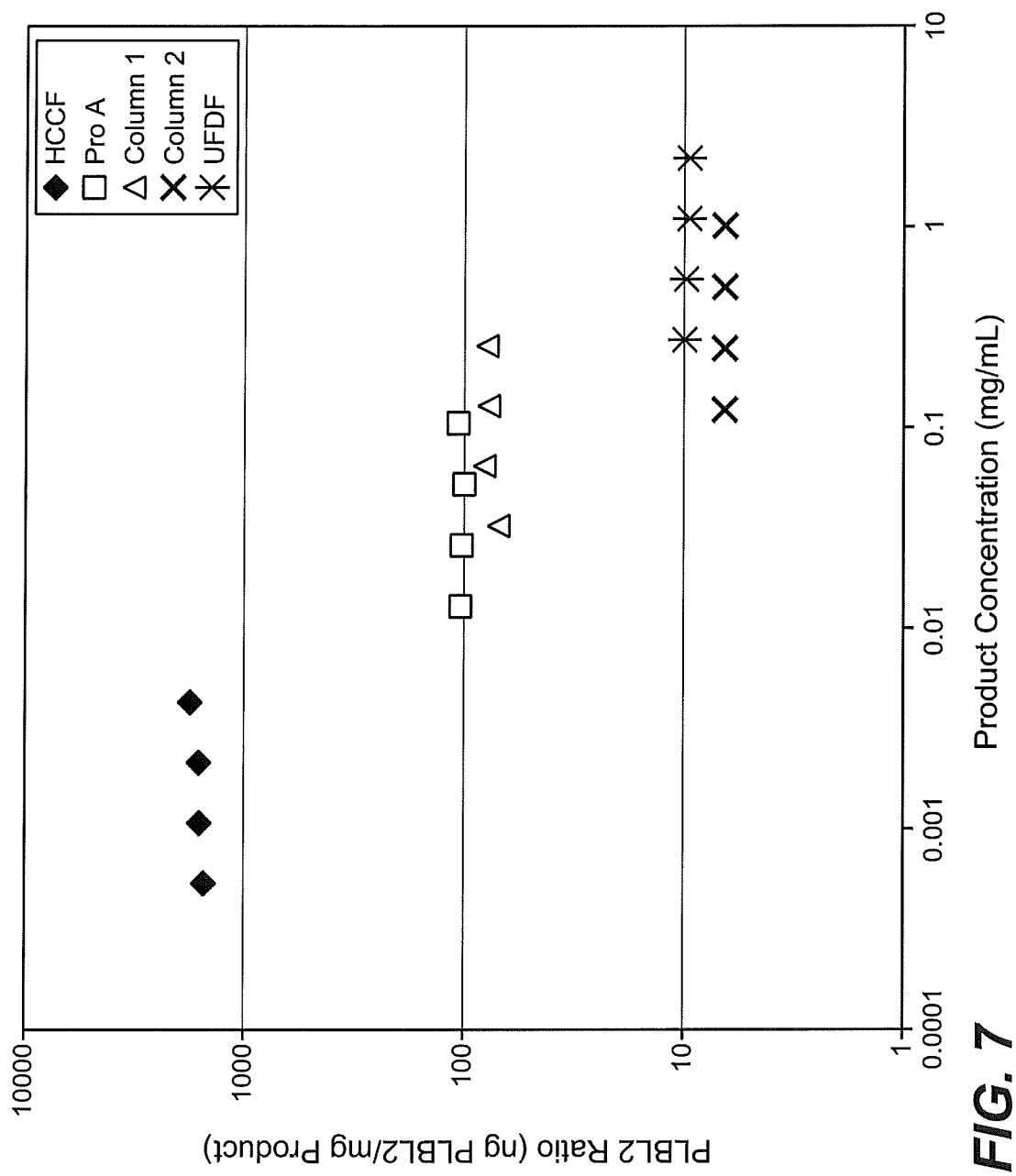
FIG. 7 shows PLBL2 clearance as measured in in-process pool samples of mAb G as described in Example 6.

We assessed PLBL2 clearance through a three-column chromatography purification process with a final ultrafiltration/diafiltration (UFDF) step of mAb G using the polyclonal PLBL2 ELISA assay described in Example 5. The results are shown in FIG. 7. As observed with the monoclonal PLBL2 ELISA assay, PLBL2 levels were highest in the HCCF and the purification process was effective for removing PLBL2 from the final mAb G preparation. The polyclonal PLBL2 ELISA assay demonstrated good sensitivity and specificity and was effective for quantifying PLBL2 levels in unpurified HCCF and at each stage of purification. We observed linearity at various product dilutions which indicates that the PLBL2 ELISA assay is not subject to the "antigen excess" problem we observed with the total CHOP assay.

In addition, we compared the quantities of PLBL2 detected using the monoclonal assay to the quantities of PLBL2 detected using the polyclonal assay in seven different runs of mAb A (including different stages of purification as indicated in Table 5) and one run of mAb B. The results are presented in Table 5. As can be seen, the relative % difference between the results obtained using each assay indicates that the two assays yield comparable results.

TABLE 5

Comparison of monoclonal PLBL2 assay results to polyclonal PLBL2 assay results.

| Sample | PLBL2 value from monoclonal ELISA (ng/mL) | PLBL2 value from polyclonal ELISA (ng/mL) | Relative % difference |
| --- | --- | --- | --- |
| mAb A Run 1 | 4,399 | 3,870 | 13 |
| mAb A Run 2 | 41,984 | 38,528 | 9 |
| mAb A Run 3 (HCCF) | 6,616 | 5,756 | 14 |
| mAb A Run 4 (ProA) | 16,302 | 13,762 | 17 |
| mAb A Run 5 (column 1) | 4,700 | 3,874 | 19 |
| mAb A Run 6 (column 2) | <1.4 | 2.3 | n/a |
| mAb A Run 7 (UFDF) | 28.98 | 27.37 | 17 |
| mAb B Run 1 | 5928 | 7144 | −19 |

Relative % Difference = [(MAb − pAb)/((Mab + pAb)/2)] * 100

Conclusion

Taken together, these data indicate that each of the monoclonal and polyclonal PLBL2 ELISA assays described herein is robust, specific and sensitive. We have shown that each assay is capable of accurately quantitating contaminating hamster PLBL2 CHOP in numerous different MAb preparations representing a wide range of PLBL2 levels and under a variety of purification conditions. We have also shown that the PLBL2 ELISA assay can be used to monitor impurity clearance during each step of the purification process. Therefore, each of the monoclonal and polyclonal PLBL2 ELISA assays described herein is an effective tool for monitoring clearance during development of purification processes as well as for quantitating PLBL2 levels in the final product.

Example 7—Use of PLBL2 ELISA Assays to Screen or Select Cell Lines

As discussed above and as shown in FIG. 4, we observed substantial differences in PLBL2 levels in HCCF between different mAb production cell lines, some of which had as much as 20-fold higher PLBL2 levels compared to others. Such substantial differences suggest that it would be desirable to identify product cell lines, and possibly even host cell lines (i.e. host cells that do not produce any product), that produce low levels of PLBL2 in the HCCF, for example, to reduce the burden on downstream purification processes. With respect to product cell lines, it would be desirable to identify lines that simultaneously produce high amounts of product and low amounts of PLBL2. A key question is whether it is possible or feasible to screen different clones of a product cell line to select a clone producing high amounts of product and low amounts of PLBL2.

Prior to generating the results described below, we did not think such a clone selection strategy would be feasible. This is because we hypothesized that the differences in PLBL2 levels observed between different product lines (see FIG. 4) was a result of the particular features of the product (e.g., MAb) produced. For example, we expected that all clones of the MAb A line would yield approximately equivalent levels of PLBL2 and that those levels would be substantially higher than PLBL2 levels produced by all clones of the MAb G line (see FIG. 4). This hypothesis was consistent with our prior experience with various MAb product lines in which we have observed that certain MAbs product lines produce higher levels of MAb relative to lines producing different MAbs, i.e. MAb production appears dependent on the characteristics of the MAb produced. In addition, we expected that cell lines with high growth and viability profiles would have more efficient protein-production machinery and therefore, would not only be more productive with respect to the particular MAb but also with respect to PLBL2 levels. In short, we thus expected that the ratios of PLBL2 to product across different clones of any particular product cell line would be relatively consistent from one clone to another.

Figure 8A:
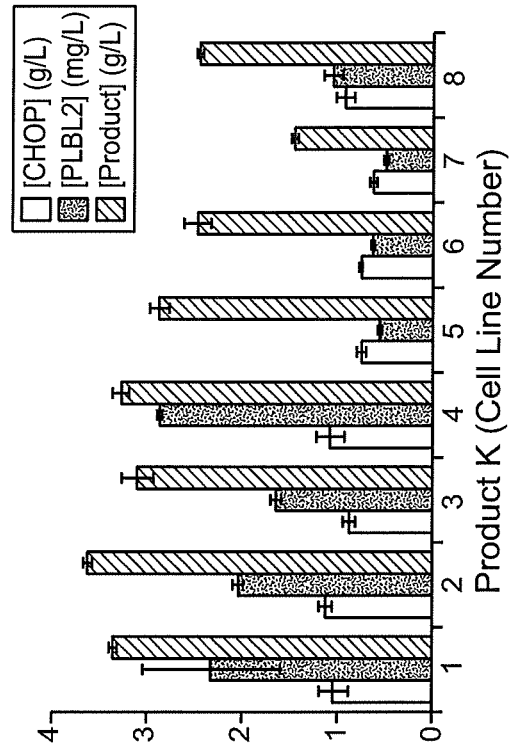
FIGS. 8A-8F show the levels of total CHOP (g/L), PLBL2 (mg/L) and product concentration (g/L) in recombinant CHO cell lines expressing (FIG. 8A) Product J, (FIG. 8B) Product K, (FIG. 8C) Product L, (FIG. 8D) Product M, (FIG. 8E) Product N, and (FIG. 8F) Product O as described in Example 7; clonal cell line numbers are indicated along the horizontal axis. All measurements were taken using day 14 HCCF samples. Error bars represent maximum and minimum measurements obtained from duplicate 2 L bioreactor cultures.
Figure 8B:
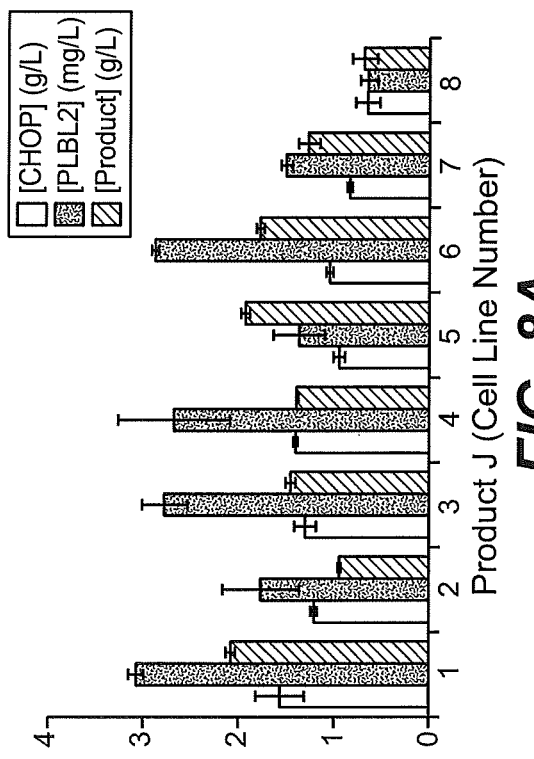
Figure 8C:
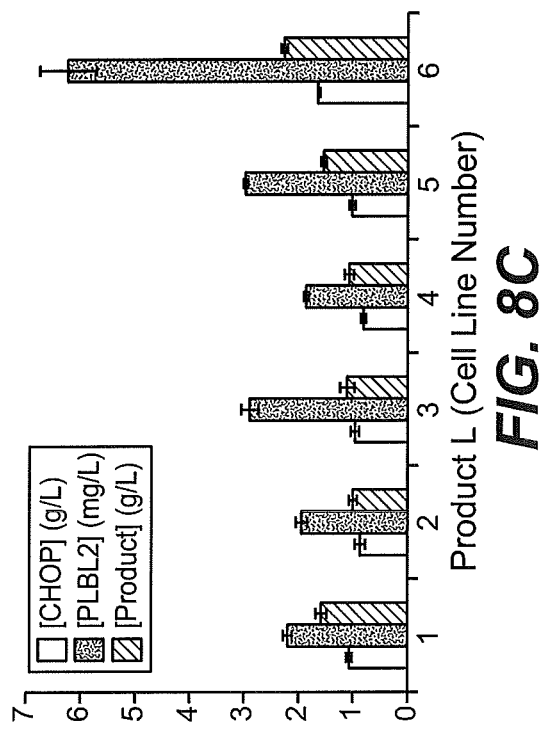
Figure 8D:
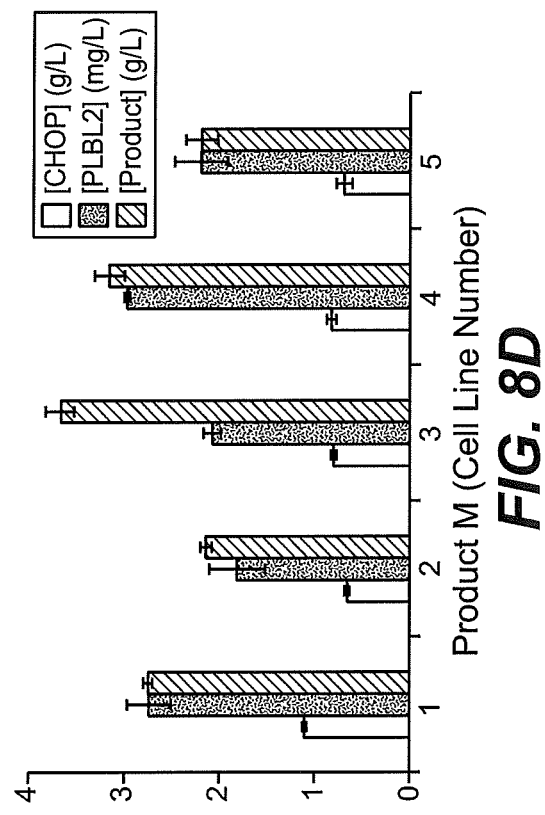
Figure 8F:
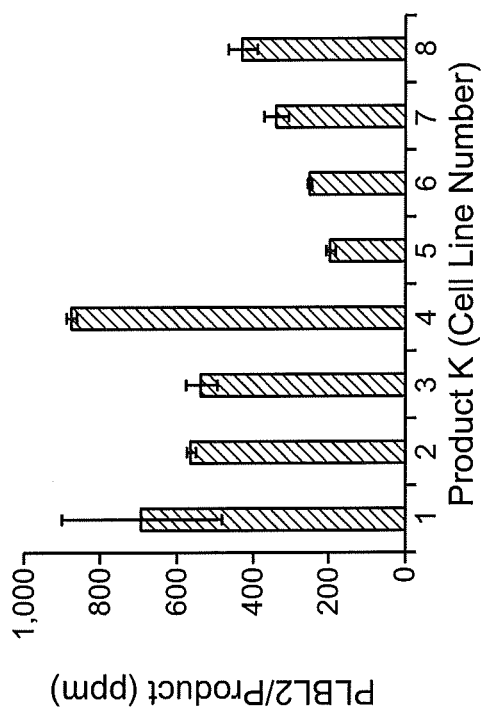

To explore the feasibility of a low PLBL2/high product concentration clone selection strategy, we used methods described above to measure PLBL2 levels, total CHOP levels, and product concentration in day 14 HCCF samples from multiple clonal lines of six different recombinant protein product CHO cell lines (Product J, Product K, Product L, Product M, Product N, and Product O). The results from duplicate 2 L bioreactor cultures for each clonal cell line are shown in FIGS. 8A-8F. As expected, product concentrations across clones of a particular product cell line did not vary substantially from one to another and the average level of product concentration across clones of a particular product cell line appeared to depend on the product produced. For example, the top producer of Product N (FIG. 8E) had a product concentration at least 1.5-fold higher than the top producer of Product L (FIG. 8C).

Figure 8E:
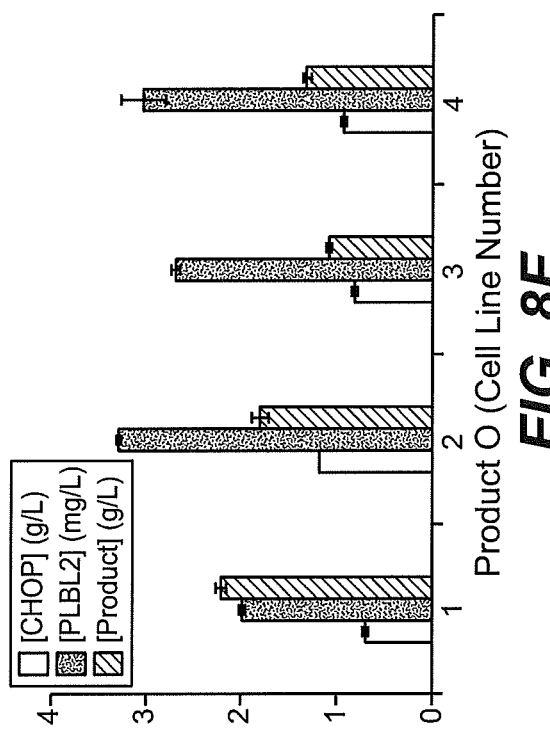
Figure 9B:
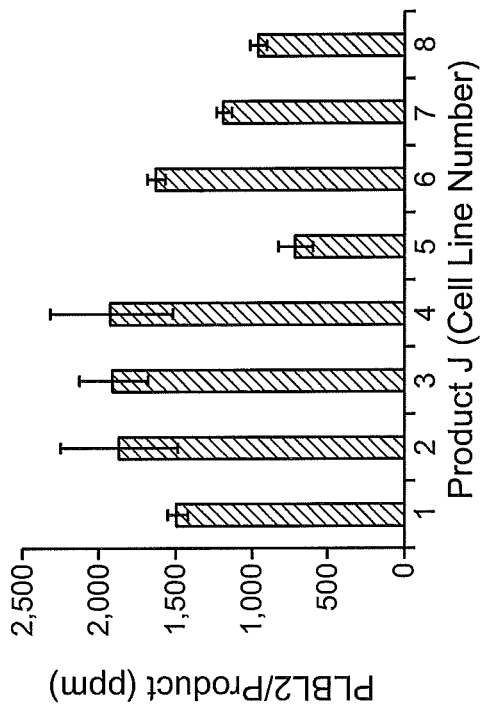
FIGS. 9A-9F show the ratio of PLBL2 (mg/L) to product concentration (g/L) in recombinant CHO cell lines expressing (FIG. 9A) Product J, (FIG. 9B) Product K, (FIG. 9C) Product L, (FIG. 9D) Product M, (FIG. 9E) Product N, and (FIG. 9F) Product O as described in Example 7; clonal cell line numbers are indicated along the horizontal axis. The ratio is reported as parts-per-million (ppm), which is equivalent to ng of PLBL2 to mg of product. Error bars represent maximum and minimum measurements obtained from day 14 HCCF from duplicate 2 L bioreactor cultures.
Figure 9A:
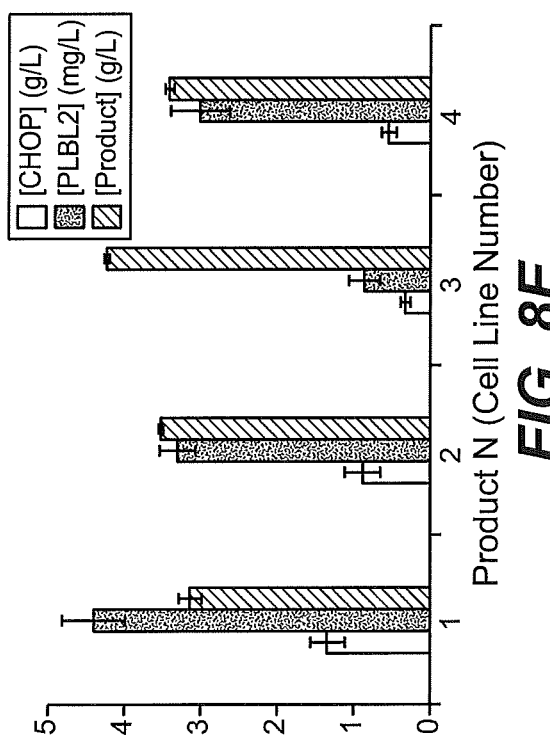
Figure 9C:
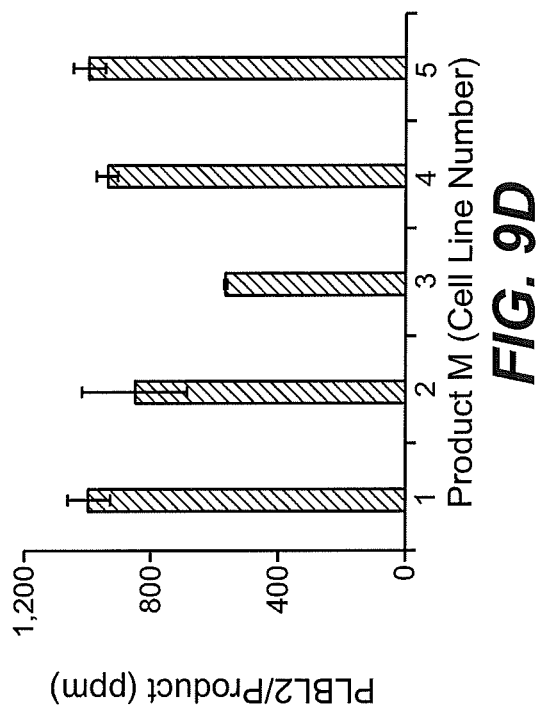
Figure 9D:
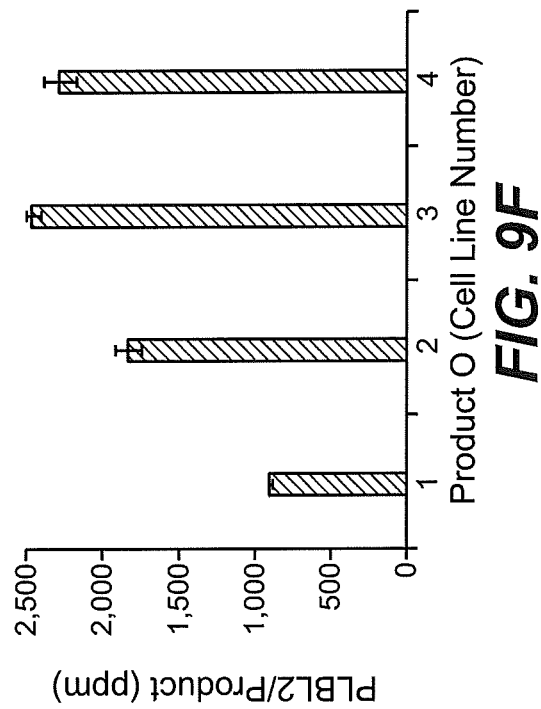
Figure 9E:
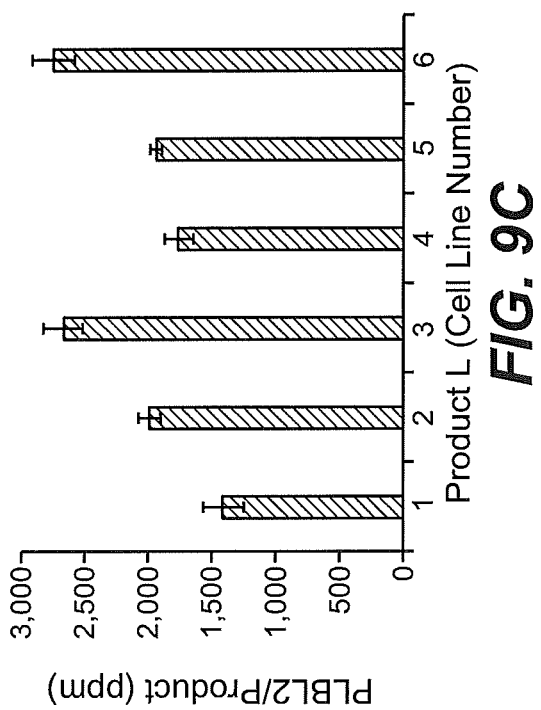
Figure 9F:
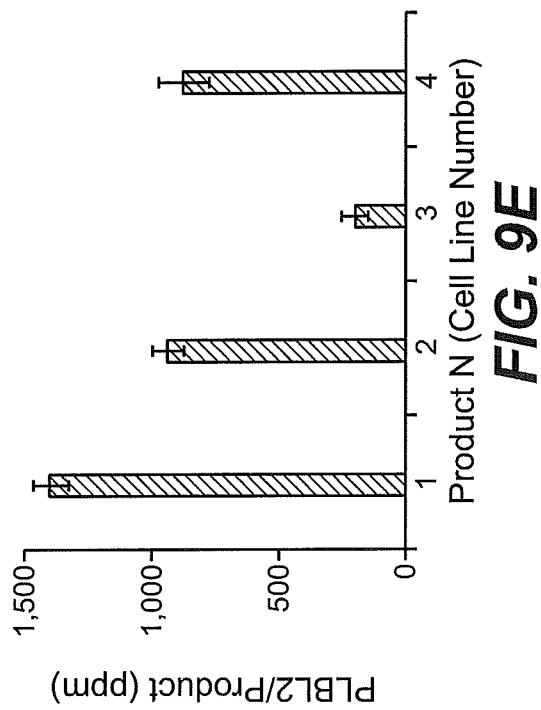

Surprisingly, however, the observation for product concentration described above did not hold true for PLBL2 levels. As can be seen in FIGS. 8A-8F, there was substantial variability in PLBL2 levels between the different clones of a particular product cell line and this clonal variability was seen in each of the six different product cell lines. Stated another way, there was not a strong correlation between product concentration and PLBL2 levels. For example, as shown in FIG. 8E (Product N), each of the clonal lines 1-4 of the Product N cell line yielded similar product concentrations ranging from about 3.5-4.5 g/L but yielded PLBL2 concentrations that differed by over five-fold (ranging from about 0.75 mg/L to about 4.5 mg/L). It is clear from the results shown in FIG. 8E that Product N Cell Line Number 3 yielded the lowest PLBL2 levels and the highest product concentration compared to any of the other Product N Cell Lines indicating the feasibility of selecting product clones with these desirable attributes. Moreover, the results show the general applicability of this selection strategy of assessing PLBL2 and product concentrations and selecting the product clones that yield low PLBL2 levels and high product concentration.

The usefulness of carrying out this selection strategy can be seen, for example, by examining the results for Product L clonal cell lines (FIG. 8C). All of the clonal cell lines were relatively low product producers but there were substantial differences in the PLBL2 levels. If product concentration was the only attribute screened for, one might select Product L Cell Line Number 6 because it yielded the highest product concentration. But Product L Cell Line Number 6 also produced substantially higher PLBL2 than any other clone, in some cases over 3-fold higher levels. In a situation where it is desirable to minimize PLBL2 levels in the Product Cell Line chosen for scale-up and further development work, the additional screening of PLBL2 levels is thus important and enables the selection of a product cell line with the desired combined attributes of low PLBL2 and high product concentration.

Another way to analyze the data presented in FIGS. 8A-8F is to calculate a ratio of the PLBL2 level to the product concentration. We calculated such a ratio for each of the cell lines discussed above with respect to FIGS. 8A-8F and plotted the data as shown in FIGS. 9A-9F. As can be seen by the data shown in FIGS. 9A-9F, clonal cell lines from a particular product cell line generated PLBL2/product concentration ratios that varied by as much as two- to ten-fold.

Such an analysis allows for rapid comparison of the desired attributes across multiple clonal cell lines of a particular product cell line and simple selection of the line with the lowest ratio, i.e. the lowest level of PLBL2 and the highest level of product concentration. For example, for Product L, it was not clear from the data presented in FIG. 8C which cell line number yielded the lowest level of PLBL2 and highest product concentration. But the data shown in FIG. 9C, which presents the ratio of PLBL2/ product concentration, clearly shows that Product L Cell Line Number 1 had the lowest ratio and therefore, the optimal combination of the desired attributes.

Figure 10:
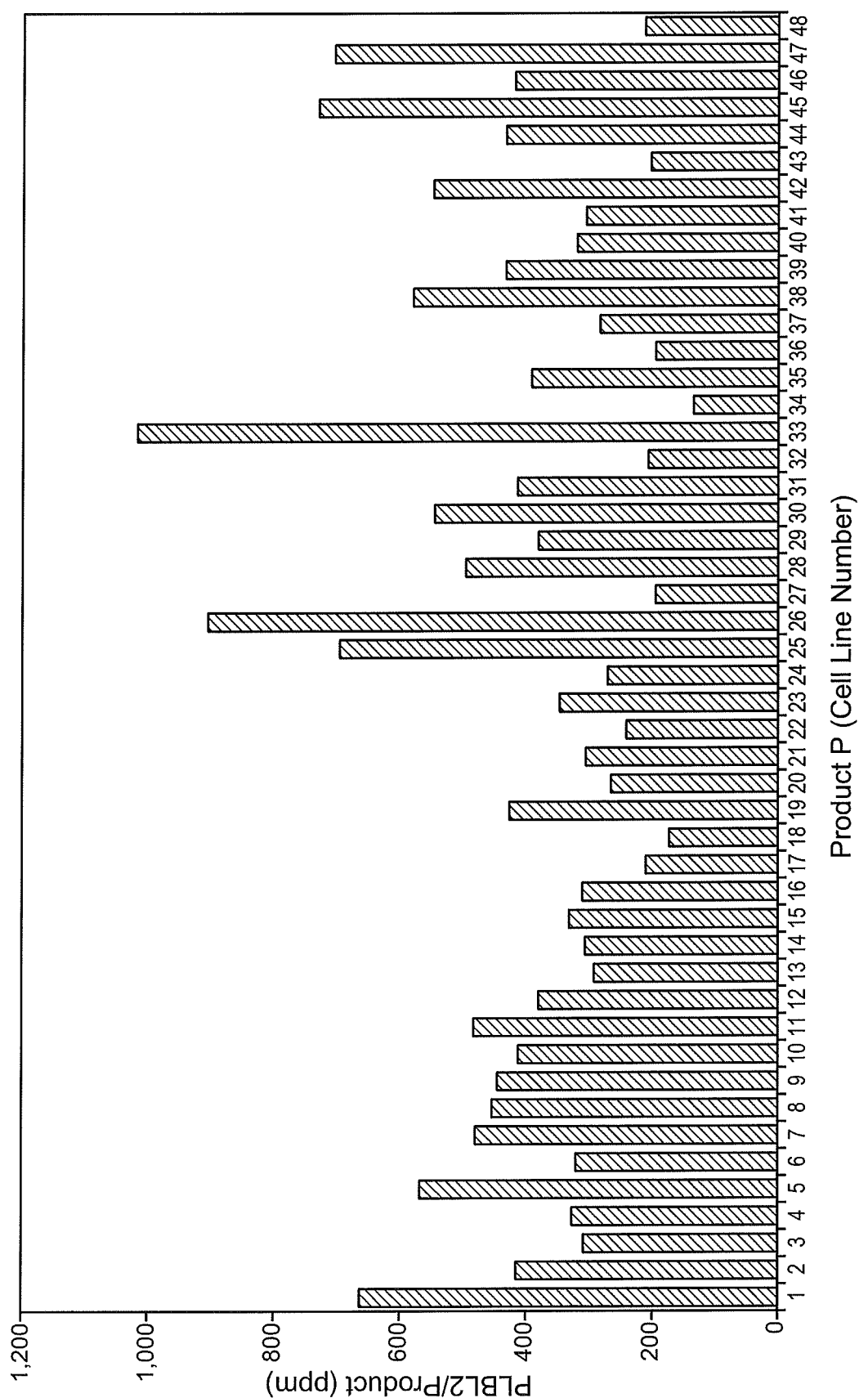
FIG. 10 shows the PLBL2/product ratio (ppm) in singlicate shake flask cultures of 48 cell lines expressing Product P as described in Example 7; clonal cell line numbers are indicated along the horizontal axis. The ratio is reported as parts-per-million (ppm), which is equivalent to ng of PLBL2 to mg of product. All measurements were obtained using day 14 HCCF samples.

To further investigate the extent of variability across multiple clonal cell lines of a particular product cell line, we analyzed 48 different recombinant CHO cell lines expressing Product P. The PLBL2/product ratio of each of the 48 cell lines of Product P is shown in FIG. 10. Across these 48 different Product P cell lines, the PLBL2/product ratio varied by as much as ten-fold. In addition, a quick review of the data shown in FIG. 10 indicates that Product P Cell Line Number 34 had the lowest ratio thereby underscoring the ease with which a product cell line with the desired attributes of low PLBL2 and high product concentration can be selected.

Figure 11A:
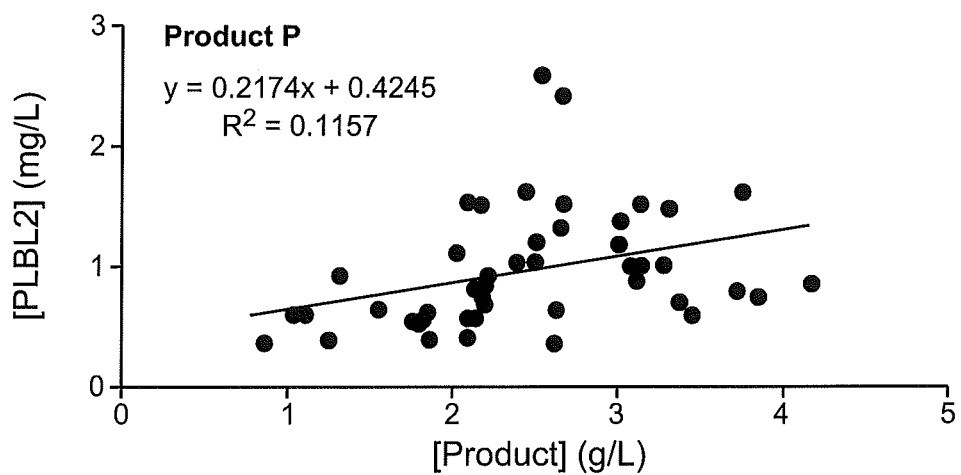
FIGS. 11A-11C show PLBL2 (mg/L), total CHOP (g/L), and product concentrations (g/L) in cultures of 48 cell lines expressing Product P as described in Example 7. Correlations between these three measurements were assessed by plotting (FIG. 11A) PLBL2 versus product concentration, (FIG. 11B) total CHOP versus product concentration, and (FIG. 11C) PLBL2 versus total CHOP concentration. All measurements were obtained using day 14 HCCF samples.
Figure 11B:
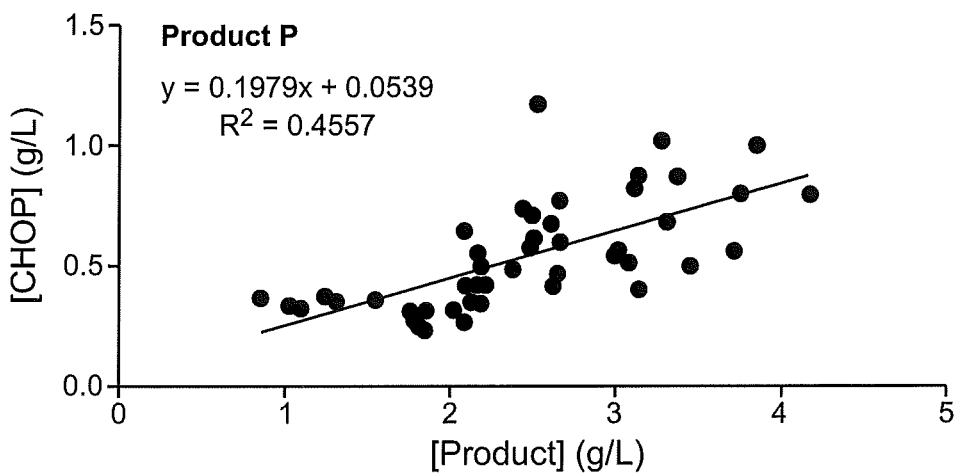
Figure 11C:
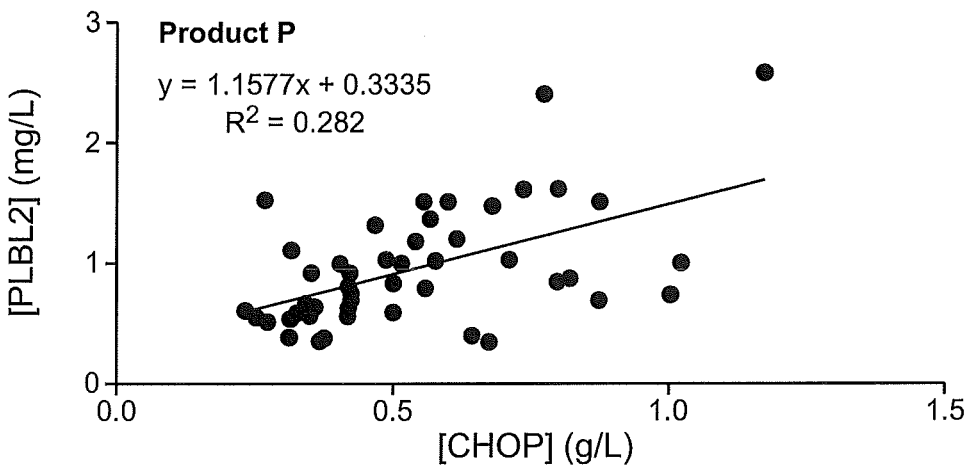

We next investigated the apparent lack of correlation between PLBL2 concentration and product concentration by measuring the levels of total CHOP, PLBL2, and product concentrations in day 14 HCCF samples from shake flask cultures of the 48 Product P cell lines described above. With this substantially larger data set involving a single product, we could more accurately quantify the correlations between these three measurements. FIG. 11A shows that there was a weak linear correlation between PLBL2 concentration and product concentration: the coefficient of determination ($R^2$) associated with the linear regression was low (<0.12). This weak correlation demonstrates the feasibility of selecting for cell lines with the desired traits of high recombinant protein productivity and low PLBL2 levels relative to other cell lines. In contrast, FIG. 11B shows that there was a moderately strong linear correlation between total CHOP concentration and product concentration ($R^2 > 0.45$). This correlation is consistent with our original postulate that cell lines that are highly productive with respect to the desired product are likely to also be highly productive with respect to host cell proteins in general because they are expected to grow well, maintain high viability, and possess strong protein production machinery. The lack of a strong linear correlation between PLBL2 concentration and total CHOP concentration ($R^2 < 0.29$) shown in FIG. 11C is a surprising finding. Because PLBL2 is a single CHOP species, we had expected that cell lines that produce more total CHOP would also produce more PLBL2 such that the ratio of PLBL2 to total CHOP would remain relatively consistent across different cell lines. This unexpected lack of strong positive correlation between PLBL2 and total CHOP levels in the HCCF across 48 cell lines demonstrates that total CHOP measurements cannot be relied on as a surrogate for PLBL2 measurements. Therefore, it cannot be assumed that cell lines with low total CHOP levels would also have low PLBL2 levels. Accordingly, direct measurements of PLBL2 in HCCF are important for the selection of cell lines with low PLBL2 levels.

To determine whether different CHO host cell lines yield different levels of PLBL2 and to distinguish any such differences from the effects of recombinant protein on PLBL2 levels in cell culture, we used the PLBL2 ELISA to measure PLBL2 levels in 2 L bioreactor cultures of three different CHO host cell lines—Host 1, Host 2, and Host 3—that did not express any product genes. These bioreactor cultures, also known as blank runs because no products were generated, were analyzed for viable cell density and viability using the Vi-Cell XR (Catalog No. 731050, Beckman Coulter, Inc., Brea, Calif., USA). Cell growth was also assessed throughout the duration of the cultivation based on packed cell volume (PCV) by centrifuging (820 g, 10 min) culture samples in KIMAX calibrated sedimentation tubes (Catalog no. 45225-10, Kimble Chase, Vineland, N.J., USA). We measured PLBL2 levels in both the HCCF and whole cell culture fluid (WCCF) for these blank runs. The WCCF samples were comprised of both cells and HCCF. Therefore, PLBL2 levels measured in WCCF samples reflects a combination of the total intracellular and extracellular concentration of PLBL2 in the cultures. Using the PLBL2 ELISA assay, we quantified the differences across the three CHO host cell lines with respect to PLBL2 profiles in both HCCF (FIG. 12A) and WCCF (FIG. 12B). In this way, we identified that Host 1 generated the highest levels of PLBL2, both in HCCF and in WCCF. By contrast, we identified Host 3 as the CHO cell line that generated the lowest levels of PLBL2 at the time of harvest (day 14).

Although Host 3 generated the overall lowest levels of PLBL2 in both HCCF and WCCF, all three CHO host cell lines showed different growth profiles (data not shown). Therefore, to negate the impact of differences in cell growth on PLBL2 levels, we further analyzed these three cell lines by normalizing PLBL2 production to the viable cell volume on a per day basis. To calculate the cell-specific PLBL2 productivity in Host 1, Host 2 and Host 3, we plotted PLBL2 concentration against the corresponding volumetric integrated viable packed cell volume (IVPCV). To minimize complications from cell death and PLBL2 release from the associated cell lysis, we limited use of the data to that at which the culture viabilities exceeded 70%. The resulting slope obtained from the linear regression provided an estimate of the cell-specific PLBL2 productivity, in units of mg of PLBL2 per unit viable cell volume per day. As shown in FIGS. 13A-13B, the slope of the linear regression was highest for Host 1 and lowest for Host 3, further demonstrating that Host 3 generated, on average, several-fold less PLBL2 per unit viable cell volume per day, whether the measurements were obtained using HCCF (FIG. 13A) or WCCF (FIG. 13B). Based on these findings, one may preferentially choose a low PLBL2 producing host, such as Host 3, as the CHO parental host for stable transfections to generate production cell lines. Such an approach may lead to stably transfected recombinant cell lines that also show lower PLBL2 levels compared to recombinant cell lines based on other CHO host cells.

The results discussed above show that the PLBL2 ELISA assays described herein can be used to assess PLBL2 levels across multiple recombinant product CHO cell lines as well as multiple CHO host cell lines thus enabling the selection of recombinant lines or host lines with desirable attributes such as low PLBL2 concentrations and, in the case recombinant product CHO cell lines, high product concentration. Such an approach to cell line selection is important for the optimization of recombinant manufacturing processes, for example, to reduce the burden on downstream purification processes.

TABLE OF SEQUENCES

| SEQ ID NO: | Description | Sequence |
|---|---|---|
| 1 | Hamster PLBL2 DNA (GenBank Accession No.: EGW13853) | atggcggccc ccatggaccg gagcccggc ggccgggcgg tccgggcgct gaggctagcg ctggcgctgg cctcgctgac tgaggtgttg ctgaattgcc cggcgggcgc cctccccacg caggggcccg gcaggcggcg ccaaaacctc gacccgccgg tctcccgcgt ccgctcggtg ctgctggacg ccgcgtcggg tcagctgcgc ctggtggacg gcatccatcc ctacgcggtg gcctgggcca acctcaccaa cgccattcgc gagaccgggt gggcctatct ggacttgggt acaaatggaa gctacaatga cagcctgcag gcctatgcag ctggtgtggt ggaggcttct gtgtctgagg agctcatcta catgcactgg atgaacacaa tggtcaacta ctgtggcccc ttcgagtatg aagttggcta ctgtgagaag ctcaagagct cctggagat caacctggag tggatgcaga gggagatgga actcagccag gactctccat attggcacca ggtgcggctg accctcctgc agctgaaagg cctagaggac agctacgaag gccgtttgac cttcccaact gggaggttca ccattaaacc cttggggttc ctcctgctgc agattgccgg agacctgaa gacctagagc aagccctgaa taagaccagc accaagcttt ccctgggctc cggttcctgc |

-continued

| SEQ ID NO: | Description | Sequence |
|---|---|---|
| | | tccgctatca tcaagttgct gccaggcgca cgtgacctcc<br>tggtggcaca caacacatgg aactcctacc agaacatgct<br>acgcatcatc aagaagtacc agctgcagtt ccggcagggg<br>cctcaagagg cgtaccccct gattgctggc aacaatttgg<br>tcttttcgtc ttacccgggc accatcttct ctggcgatga<br>cttctacatc ctgggcagtg ggctggtcac cctggagacc<br>accattggca caagaatcc agccctgtgg aagtacgtgc<br>agccccaggg ctgtgtgctg gagtggattc gaaacatcgt<br>ggccaaccgc ctggccttgg acggggccac ctgggcagac<br>atcttcaagc agttcaatag tggcacgtat aataaccaat<br>ggatgattgt ggactacaag gcattcatcc ccaacgggcc<br>cagccctgga agccgagtgc ttaccatcct agaacagatc<br>ccgggcatgg tggtggtggc cgacaagact gaagatctct<br>acaagacaac ctactgggct agctacaaca tcccgttctt<br>tgagattgtg ttcaacgcca gtgggctgca ggacttggtg<br>gcccaatatg gagattggtt ttcctacact aagaaccctc<br>gagctcagat cttccagagg gaccagtcgc tggtggagga<br>catgaattcc atggtccggc tcataaggta caacaacttc<br>cttcacgacc ctctgtcact gtgtgaagcc tgtatcccga<br>agcccaatgc agagaatgcc atctctgccc gctctgacct<br>caatcctgcc aatggctcct acccatttca agccctgtac<br>cagcgtcccc acggtggcat cgatgtgaag gtgaccagct<br>tttcactggc caagcgcatg agcatgctgg cagccagtgg<br>cccaacgtgg gatcagttgc ccccattcca gtggagttta<br>tcgccgttcc gcagcatgct tcacatgggc agcctgatc<br>tctggacatt ctcacccatc agtgtcccat gggactga |
| 2 | Hamster PLBL2 Protein (GenBank Accession No.: EGW13853) | MAAPMDRSPG GRAVRALRLA LALASLTEVL LNCPAGALPT<br>QGPGRRRQNL DPPVSRVRSV LLDAASGQLR LVDGIHPYAV<br>AWANLTNAIR ETGWAYLDLG TNGSYNDSLQ AYAAGVVEAS<br>VSEELIYMHW MNTMVNYCGP FEYEVGYCEK LKSFLEINLE<br>WMQREMELSQ DSPYWHQVRL TLLQLKGLED SYEGRLTFPT<br>GRFTIKPLGF LLLQIAGDLE DLEQALNKTS TKLSLGSGSC<br>SAIIKLLPGA RDLLVAHNTW NSYQNMLRII KKYQLQFRQG<br>PQEAYPLIAG NNLVFSSYPG TIFSGDDFYI LGSGLVTLET<br>TIGNKNPALW KYVQPQGCVL EWIRNIVANR LALDGATWAD<br>IFKQFNSGTY NNQWMIVDYK AFIPNGPSPG SRVLTILEQI<br>PGMVVVADKT EDLYKTTYWA SYNIPFFEIV FNASGLQDLV<br>AQYGDWFSYT KNPRAQIFQR DQSLVEDMNS MVRLIRYNNF<br>LHDPLSLCEA CIPKPNAENA ISARSDLNPA NGSYPFQALY<br>QRPHGGIDVK VTSFSLAKRM SMLAASGPTW DQLPPFQWSL<br>SPFRSMLHMG QPDLWTFSPI SVPWD |
| 3 | 15G11 heavy chain (mu-IgG1) | EVKLEESGGGLVQPGGSTKLSCAASGFTFSDAWMDWVRQCPEK<br>GLEWVAEISSKANNRATYYAESVKGRFTISRDDSKSCVYLQMN<br>SLRAEDTGIYYCTRRGYTMDYWGQGTSVTVSSASTKGPSVYPL<br>APGSAAQTNSMVTLGCLVKGYFPEPVTVTWNSGSISSGVHTFP<br>AVLQSDLYTLSSSVTVPSSTWPSETVTCNVAHPASSTKVDKKI<br>VPRDCGCKPCICTVPEVSSVFIFPPKPKDVLTITLTPKVTCVV<br>VDISKDDPEVQFSWFVDDVEVHTAQTQPREEQFNSTFRSVSEL<br>PIMHQDWLNGKEFKCRVNSAAFPAPIEKTISKTKGRPKAPQVY<br>TIPPPKEQMAKDKVSLTCMITDFFPEDITVEWQWNGQPAENYK<br>NTQPIMDTDGSYFVYSKLNVQKSNWEAGNTFTCSVLHEGLHNH<br>HTEKSLSHSPGK |
| 4 | 15G11 heavy chain variable region (VH) | EVKLEESGGGLVQPGGSTKLSCAASGFTFSDAWMDWVRQCPEK<br>GLEWVAEISSKANNRATYYAESVKGRFTISRDDSKSCVYLQMN<br>SLRAEDTGIYYCTRRGYTMDYWGQGTSVTVSS |
| 5 | 15G11 CDRH1 | GFTFSDAWMD |
| 6 | 15G11 CDRH2 | EISSKANNRATYYAESVKG |
| 7 | 15G11 CDRH3 | TRRGYTMDY |
| 8 | 15G11 light chain (mu-kappa) | DIVMTQSQKFMSTSVGDRVSVTCKASQNVDTNVAWYQQKPGQS<br>PKALIFSASYRFSGVPDRFTGSGSGTDFTLTISNVQSEDLAEY<br>FCQQYNNFPFTFGSGTKLELKRADAAPTVSIFPPSSEQLTSGG<br>ASVVCFLNNFYPKDINVKWKIDGSERQNGVLNSWTDQDSKDST<br>YSMSSTLTLTKDEYERHNSYTCEATHKTSTSPIVKSFNRNEC |
| 9 | 15G11 light chain variable region (VL) | DIVMTQSQKFMSTSVGDRVSVTCKASQNVDTNVAWYQQKPGQS<br>PKALIFSASYRFSGVPDRFTGSGSGTDFTLTISNVQSEDLAEY<br>FCQQYNNFPFTFGSGTKLELK |

TABLE OF SEQUENCES

| SEQ ID NO: | Description | Sequence |
|---|---|---|
| 10 | 15G11 CDRL1 | KASQNVDTNVA |
| 11 | 15G11 CDRL2 | SASYRFS |
| 12 | 15G11 CDRL3 | QQYNNFPFT |
| 13 | 19C10 heavy chain (mu-IgG1) | EVQLQESGPCLVKPSQTLSLTCSVTGDSITSGYWNWIRKFPGN KLESMGYISYSGSTYYNPSLKSRISITRDTSKNQYYLQLNSVT TEDTATYYCARIASWITTYFDYWGQGTTLTVSSASTKGPSVYP LAPGSAAQTNSMVTLGCLVKGYFPEPVTVTWNSGSLSSGVHTF PAVLQSDLYTLSSSVTVPSSTWPSETVTCNVAHPASSTKVDKK IVPRDCGCKPCICTVPEVSSVFIFPPKPKDVLTITLTPKVTCV VVDISKDDPEVQFSWFVDDVEVHTAQTQPREEQFNSTFRSVSE LPIMHQDWLNGKEFKCRVNSAAFPAPIEKTISKTKGRPKAPQV YTIPPPKEQMAKDKVSLTCMITDFFPEDITVEWQWNGQPAENY KNTQPIMDTDGSYFVYSKLNVQKSNWEAGNTFTCSVLHEGLHN HHTEKSLSHSPGK |
| 14 | 19C10 heavy chain variable region (VH) | EVQLQESGPCLVKPSQTLSLTCSVTGDSITSGYWNWIRKFPGN KLESMGYISYSGSTYYNPSLKSRISITRDTSKNQYYLQLNSVT TEDTATYYCARIASWITTYFDYWGQGTTLTVSS |
| 15 | 19C10 CDRH1 | GDSITSGYWN |
| 16 | 19C10 CDRH2 | YISYSGSTYYNPSLKS |
| 17 | 19C10 CDRH3 | ARIASWITTYFDY |
| 18 | 19C10 light chain (mu-kappa) | DIVMTQSPAILSVSPGERVSFSCRASQSIGTSIHWYQQRRNGS PRLLIKYASESISGIPSRFSGSGSGTDFILSINSVESEDIADY YCQQSNSWPYTFGGGTKLELKRADAAPTVSIFPPSSEQLTSGG ASVVCFLNNFYPKDINVKWKIDGSERQNGVLNSWTDQDSKDST YSMSSTLTLTKDEYERHNSYTCEATHKTSTSPIVKSFNRNEC |
| 19 | 19C10 light chain variable region (VL) | DIVMTQSPAILSVSPGERVSFSCRASQSIGTSIHWYQQRRNGS PRLLIKYASESISGIPSRFSGSGSGTDFILSINSVESEDIADY YCQQSNSWPYTFGGGTKLELK |
| 20 | 19C10 CDRL1 | RASQSIGTSIH |
| 21 | 19C10 CDRL2 | YASESIS |
| 22 | 19C10 CDRL3 | QQSNSWPYT |

What is claimed is:

1. A monoclonal antibody that binds hamster phospholipase B-like 2, wherein the antibody comprises:
   a variable heavy chain region comprising CDRH1 comprising the amino acid sequence of SEQ ID NO.: 15, CDRH2 comprising the amino acid sequence of SEQ ID NO.: 16, and CDRH3 comprising the amino acid sequence of SEQ ID NO.: 17; and
   a variable light chain region comprising COMA comprising the amino acid sequence of SEQ ID NO.: 20, CDRL2 comprising the amino acid sequence of SEQ ID NO.: 21, and CDRL3 comprising the amino acid sequence of SEQ ID NO.: 22.

2. The antibody of claim 1 comprising a variable heavy chain region comprising the amino acid sequence of SEQ ID NO.: 14.

3. The antibody of claim 1 comprising a variable light chain region comprising the amino acid sequence of SEQ ID NO.: 19.

4. The antibody of claim 1 comprising a variable heavy chain region comprising the amino acid sequence of SEQ ID NO.: 14 and a variable light chain region comprising the amino acid sequence of SEQ ID NO.: 19.

5. The antibody of claim 4 comprising a heavy chain comprising the amino acid sequence of SEQ ID NO.: 13 and a light chain comprising the amino acid sequence of SEQ ID NO.: 18.

6. A monoclonal antibody that binds hamster phospholipase B-like 2, wherein the antibody comprises:
   a variable heavy chain region comprising CDRH1 comprising the amino acid sequence of SEQ ID NO.: 5, CDRH2 comprising the amino acid sequence of SEQ ID NO.: 6, and CDRH3 comprising the amino acid sequence of SEQ ID NO.: 7; and
   a variable light chain region comprising CDRL1 comprising the amino acid sequence of SEQ ID NO.: 10, CDRL2 comprising the amino acid sequence of SEQ ID NO.: 11, and CDRL3 comprising the amino acid sequence of SEQ ID NO.: 12.

7. The antibody of claim 6 comprising a variable heavy chain region comprising the amino acid sequence of SEQ ID NO.: 4.

8. The antibody of claim 6 comprising a variable light chain region comprising the amino acid sequence of SEQ ID NO.: 9.

9. The antibody of claim 6 comprising a variable heavy chain region comprising the amino acid sequence of SEQ ID NO.: 4 and a variable light chain region comprising the amino acid sequence of SEQ ID NO.: 9.

10. The antibody of claim 9 comprising a heavy chain comprising the amino acid sequence of SEQ ID NO.: 3 and a light chain comprising the amino acid sequence of SEQ ID NO.: 8.

11. An immunoassay kit tar the detection at hamster phospholipase B-like 2 protein comprising a capture antibody, wherein the capture antibody is the monoclonal antibody of claim 1.

12. The immunoassay kit of claim 11, wherein the immunoassay is an ECL immunoassay.

13. The immunoassay kit of claim 11, wherein the immunoassay is an ELISA immunoassay.

14. The immunoassay kit of claim 11, wherein the kit further comprises a detection antibody that comprises a variable heavy chain region comprising CDRH1 comprising the amino acid sequence of SEQ ID NO.: 5, CDRH2 comprising the amino acid sequence of SEQ ID NO.: 6, and CDRH3 comprising the amino acid sequence of SEQ ID NO.: 7 and a variable light chain region comprising CDRL1 comprising the amino acid sequence of SEQ ID NO.: 10, CDRL2 comprising the amino acid sequence of SEQ ID NO.: 11, and CDRL3 comprising the amino acid sequence of SEQ ID NO.: 12.

15. An immunoassay kit for the detection of hamster phospholipase B-like 2 protein comprising a detection antibody, wherein the detection antibody is the monoclonal antibody of claim 6.

16. The immunoassay kit of claim 15, wherein the immunoassay is an ECL immunoassay.

17. The immunoassay kit of claim 15, wherein the immunoassay is an ELISA immunoassay.

18. The immunoassay kit of claim 11, wherein the capture antibody comprises a variable heavy chain region comprising the amino acid sequence of SEQ ID NO.: 14 and a variable light chain region comprising the amino acid sequence of SEQ ID NO.: 19.

19. The immunoassay kit of claim 14, wherein the detection antibody comprises a variable heavy chain region comprising the amino acid sequence of SEQ ID NO.: 4 and a variable light chain region comprising the amino acid sequence of SEQ ID NO.: 9.

20. An immunoassay kit for the detection of hamster phospholipase B-like 2 protein comprising a capture antibody and a detection antibody, wherein:
   the capture antibody comprises a variable heavy chain region comprising CDRH1 comprising the amino acid sequence of SEQ ID NO.: 15, CDRH2 comprising the amino acid sequence of SEQ ID NO.: 16, and CDRH3 comprising the amino acid sequence of SEQ ID NO.:

17 and a variable light chain region comprising CDRL1 comprising the amino acid sequence of SEQ ID NO.: 20, CDRL2 comprising the amino acid sequence of SEQ ID NO.: 21, and CDRL3 comprising the amino acid sequence of SEQ ID NO.: 22; and the detection antibody comprises a variable heavy chain region comprising CDRH1 comprising the amino acid sequence of SEQ ID NO.: 5, CDRH2 comprising the amino acid sequence of SEQ ID NO.: 6, and CDRH3 comprising the amino acid sequence of SEQ ID NO.: 7 and a variable light chain region comprising CDRL1 comprising the amino acid sequence of SEQ ID NO.: 10, CDRL2 comprising the amino acid sequence of SEQ ID NO.: 11, and CDRL3 comprising the amino acid sequence of SEQ ID NO.: 12.

21. The immunoassay kit of claim 20, wherein the capture antibody comprises a variable heavy chain region comprising the amino acid sequence of SEQ ID NO.: 14 and a variable light chain region comprising the amino acid sequence of SEQ ID NO.: 19; and the detection antibody comprises a variable heavy chain region comprising the amino acid sequence of SEQ ID NO.: 4 and a variable light chain region comprising the amino acid sequence of SEQ ID NO.: 9.

* * * * *

UNITED STATES PATENT AND TRADEMARK OFFICE
CERTIFICATE OF CORRECTION

PATENT NO.       : 10,788,494 B2
APPLICATION NO.  : 15/914094
DATED            : September 29, 2020
INVENTOR(S)      : Feny Gunawan et al.

It is certified that error appears in the above-identified patent and that said Letters Patent is hereby corrected as shown below:

In the Claims

In Claim 1, Column 77, Line 27, "COMA" should read --CDRL1--

In Claim 11, Column 78, Lines 34-35, "An immunoassay kit tar the detection at hamster" should read --An immunoassay kit for the detection of hamster--

Signed and Sealed this
Eighth Day of December, 2020

Andrei Iancu
*Director of the United States Patent and Trademark Office*